United States Patent
Tse et al.

(10) Patent No.: US 7,652,092 B2
(45) Date of Patent: *Jan. 26, 2010

(54) ARTICLES FROM PLASTICIZED THERMOPLASTIC POLYOLEFIN COMPOSITIONS

(75) Inventors: Mun Fu Tse, Seabrook, TX (US); Chon-Yie Lin, Houston, TX (US); Bryan R. Chapman, Annandale, NJ (US); Bruce R. Lundmark, Waller, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/406,654

(22) Filed: Apr. 19, 2006

(65) Prior Publication Data

US 2006/0189744 A1    Aug. 24, 2006

Related U.S. Application Data

(63) Continuation-in-part of application No. 10/640,435, filed on Aug. 12, 2003, and a continuation-in-part of application No. 10/634,351, filed on Aug. 4, 2003.

(60) Provisional application No. 60/402,665, filed on Aug. 12, 2002.

(51) Int. Cl.
*C08K 5/01* (2006.01)
*C08L 23/12* (2006.01)
*C08L 23/14* (2006.01)
*C08J 3/18* (2006.01)

(52) U.S. Cl. .............. 524/491; 524/490; 524/848; 524/348; 524/348.2; 524/348.5; 524/348.6; 524/351; 524/378; 524/376; 524/396

(58) Field of Classification Search ............ 524/490, 524/583, 582, 585, 570, 491, 848, 366, 107; 525/280, 240
See application file for complete search history.

(56) References Cited

U.S. PATENT DOCUMENTS

| | | |
|---|---|---|
| 3,201,364 A | 8/1965 | Salyer et al. |
| 3,318,835 A | 5/1967 | Hagemeyer, Jr. et al. |
| 3,415,925 A | 12/1968 | Marans et al. |
| 3,439,088 A | 4/1969 | Edman et al. |
| 3,590,528 A | 7/1971 | Shepherd |
| 3,686,385 A | 8/1972 | Rohn |
| 3,818,105 A | 6/1974 | Coopersmith et al. |
| 3,828,105 A | 8/1974 | Saurano et al. |
| 3,894,120 A | 7/1975 | Frese et al. |
| 3,957,898 A | 5/1976 | Girotti et al. |
| 4,038,238 A | 7/1977 | Cravens |
| 4,041,002 A | 8/1977 | Aboshi et al. |
| 4,041,103 A | 8/1977 | Davison et al. |
| 4,073,782 A | 2/1978 | Kishi et al. |
| 4,087,505 A | 5/1978 | Sugimoto et al. |
| 4,097,543 A | 6/1978 | Haag et al. |
| 4,110,185 A | 8/1978 | Williams et al. |
| 4,113,802 A | 9/1978 | Matteoli et al. |
| 4,132,698 A | 1/1979 | Gessler et al. |
| 4,154,244 A | 5/1979 | Becker et al. |
| 4,166,057 A | 8/1979 | Takemori |
| 4,170,586 A | 10/1979 | Clampitt et al. |
| 4,210,570 A | 7/1980 | Trotter et al. |
| 4,274,932 A | 6/1981 | Williams et al. |
| 4,304,713 A * | 12/1981 | Perelman ................ 264/45.9 |
| 4,311,628 A | 1/1982 | Abdou-Sabet et al. |
| 4,321,334 A | 3/1982 | Chatterjee |
| 4,325,850 A | 4/1982 | Mueller |
| 4,358,384 A | 11/1982 | Newcomb |
| 4,369,284 A | 1/1983 | Chen |
| 4,430,289 A | 2/1984 | McKinney et al. |
| 4,454,281 A * | 6/1984 | Heitz et al. ................ 524/399 |
| 4,467,010 A | 8/1984 | Shii et al. |
| 4,467,065 A | 8/1984 | Williams et al. |
| 4,483,952 A * | 11/1984 | Uchiyama ................ 524/108 |
| 4,536,537 A | 8/1985 | Klingensmith et al. |
| 4,592,851 A | 6/1986 | Stadtmiller et al. |
| 4,645,791 A | 2/1987 | Theodore et al. |
| 4,663,220 A | 5/1987 | Wisneski et al. |
| 4,693,838 A | 9/1987 | Varma et al. |
| 4,703,078 A | 10/1987 | Maehara et al. |
| 4,726,989 A | 2/1988 | Mrozinski |
| 4,749,734 A | 6/1988 | Williams et al. |
| 4,774,277 A | 9/1988 | Janac et al. |
| 4,824,718 A | 4/1989 | Hwang |
| 4,833,195 A | 5/1989 | Adur et al. |
| 4,845,137 A | 7/1989 | Williams et al. |
| 4,853,428 A | 8/1989 | Theodore et al. |
| 4,857,646 A * | 8/1989 | Jaffe ........................ 546/49 |
| 4,863,785 A | 9/1989 | Berman et al. |
| 4,912,148 A | 3/1990 | Kim et al. |
| 4,948,840 A | 8/1990 | Berta |
| 4,959,402 A | 9/1990 | Williams et al. |
| 4,960,820 A | 10/1990 | Hwo |
| 4,994,552 A | 2/1991 | Williams et al. |
| 4,996,094 A | 2/1991 | Dutt |
| 5,049,605 A * | 9/1991 | Rekers ................... 524/108 |
| 5,076,988 A | 12/1991 | Rifi |
| 5,079,287 A | 1/1992 | Takeshi et al. |
| 5,080,942 A | 1/1992 | Yau |

(Continued)

FOREIGN PATENT DOCUMENTS

CS    215313    8/1982

(Continued)

OTHER PUBLICATIONS

JP 6-1892 (Jan. 1994) abstract in English.*

(Continued)

*Primary Examiner*—David Wu
*Assistant Examiner*—Rip A. Lee
(74) *Attorney, Agent, or Firm*—Catherine L. Bell

(57) ABSTRACT

The present invention relates to articles made from plasticized thermoplastic polyolefin compositions comprising a thermoplastic polyolefin, a nucleating agent, and a non-functionalized hydrocarbon plasticizer.

52 Claims, 2 Drawing Sheets

U.S. PATENT DOCUMENTS

| | | | |
|---|---|---|---|
| 5,105,038 A | 4/1992 | Chen et al. | |
| 5,114,763 A | 5/1992 | Brant et al. | |
| 5,143,978 A | 9/1992 | Berta | |
| 5,162,436 A | 11/1992 | Davis et al. | |
| 5,171,908 A | 12/1992 | Rudnick | |
| 5,180,865 A | 1/1993 | Heilman et al. | |
| 5,230,843 A | 7/1993 | Howard et al. | |
| 5,240,966 A | 8/1993 | Iwasaki et al. | |
| 5,254,378 A | 10/1993 | Krueger et al. | |
| 5,264,277 A | 11/1993 | Frognet et al. | |
| 5,340,848 A | 8/1994 | Asanuma et al. | |
| 5,356,948 A | 10/1994 | Payne, Jr. et al. | |
| 5,360,868 A | 11/1994 | Mosier et al. | |
| 5,412,020 A | 5/1995 | Yamamoto et al. | |
| 5,512,625 A | 4/1996 | Butterbach et al. | |
| 5,548,008 A | 8/1996 | Asanuma et al. | |
| 5,552,482 A | 9/1996 | Berta | |
| 5,569,693 A | 10/1996 | Doshi et al. | |
| 5,591,817 A | 1/1997 | Asanuma et al. | |
| 5,614,297 A | 3/1997 | Velazquez | |
| 5,624,627 A | 4/1997 | Yagi et al. | |
| 5,700,312 A * | 12/1997 | Fausnight et al. | 106/10 |
| 5,776,589 A | 7/1998 | Mace et al. | |
| 5,783,531 A | 7/1998 | Andrew et al. | |
| 5,869,555 A | 2/1999 | Simmons et al. | |
| 5,891,946 A | 4/1999 | Nohara et al. | |
| 5,968,455 A | 10/1999 | Brickley | |
| 5,969,021 A | 10/1999 | Reddy et al. | |
| 6,001,455 A | 12/1999 | Nishio et al. | |
| 6,025,448 A | 2/2000 | Swindoll et al. | |
| 6,037,384 A * | 3/2000 | Kakizawa et al. | 521/182 |
| 6,042,902 A | 3/2000 | Kuder et al. | |
| 6,045,922 A | 4/2000 | Janssen et al. | |
| 6,084,031 A * | 7/2000 | Medsker et al. | 525/192 |
| 6,086,996 A | 7/2000 | Rancich et al. | |
| 6,090,081 A | 7/2000 | Sudo et al. | |
| 6,111,039 A | 8/2000 | Miro et al. | |
| 6,143,818 A | 11/2000 | Wang et al. | |
| 6,191,078 B1 * | 2/2001 | Shlomo et al. | 508/273 |
| 6,197,285 B1 | 3/2001 | Kowalik et al. | |
| 6,303,067 B1 * | 10/2001 | Wong et al. | 264/289.6 |
| 6,329,468 B1 | 12/2001 | Wang | |
| 6,337,364 B1 | 1/2002 | Sakaki et al. | |
| 6,342,565 B1 | 1/2002 | Cheng et al. | |
| 6,403,692 B1 | 6/2002 | Traugott et al. | |
| 6,451,915 B1 | 9/2002 | Ellul et al. | |
| 6,465,109 B2 | 10/2002 | Ohtsuka | |
| 6,498,213 B2 | 12/2002 | Jeong et al. | |
| 6,515,231 B1 | 2/2003 | Strobech et al. | |
| 6,632,974 B1 | 10/2003 | Suzuki et al. | |
| 6,642,316 B1 | 11/2003 | Datta et al. | |
| 6,706,828 B2 | 3/2004 | DiMaio | |
| 6,720,376 B2 | 4/2004 | Itoh et al. | |
| 6,730,739 B2 | 5/2004 | Gipson | |
| 6,753,373 B2 | 6/2004 | Winowiecki | |
| 6,803,415 B1 | 10/2004 | Mikielski et al. | |
| 6,861,143 B2 * | 3/2005 | Castellani et al. | 428/379 |
| 6,867,253 B1 | 3/2005 | Chen | |
| 6,905,760 B1 | 6/2005 | Mukohara et al. | |
| 7,271,209 B2 | 9/2007 | Li et al. | |
| 2002/0160137 A1 | 10/2002 | Varma | |
| 2002/0183429 A1 | 12/2002 | Itoh et al. | |
| 2002/0188057 A1 | 12/2002 | Chen | |
| 2003/0022977 A1 | 1/2003 | Hall | |
| 2003/0036577 A1 | 2/2003 | Hughes et al. | |
| 2003/0181575 A1 | 9/2003 | Schmidt et al. | |
| 2004/0034148 A1 | 2/2004 | Kelly et al. | |
| 2004/0054040 A1 | 3/2004 | Lin et al. | |
| 2004/0063806 A1 | 4/2004 | Kaarnakari | |
| 2004/0091631 A1 | 5/2004 | Belli et al. | |
| 2004/0106723 A1 | 6/2004 | Yang et al. | |
| 2004/0116515 A1 | 6/2004 | Anderson et al. | |
| 2004/0186214 A1 | 9/2004 | Li et al. | |
| 2004/0241309 A1 * | 12/2004 | Garmier | 426/601 |
| 2004/0249046 A1 | 12/2004 | Abhari et al. | |
| 2004/0260001 A1 | 12/2004 | Lin et al. | |
| 2004/0266948 A1 | 12/2004 | Jacob et al. | |
| 2005/0018983 A1 | 1/2005 | Brown et al. | |
| 2005/0106978 A1 | 5/2005 | Cheng et al. | |
| 2005/0148720 A1 | 7/2005 | Li et al. | |
| 2005/0170117 A1 | 8/2005 | Cleveland et al. | |
| 2005/0271851 A1 | 12/2005 | Shibatou et al. | |
| 2005/0277738 A1 | 12/2005 | Hoyweghen et al. | |
| 2006/0008643 A1 | 1/2006 | Lin et al. | |
| 2006/0079617 A1 | 4/2006 | Kappes et al. | |
| 2006/0100347 A1 | 5/2006 | Ouhadi et al. | |
| 2006/0135699 A1 | 6/2006 | Li et al. | |
| 2006/0167184 A1 | 7/2006 | Waddell et al. | |
| 2006/0173123 A1 | 8/2006 | Yang et al. | |
| 2006/0189763 A1 | 8/2006 | Yang et al. | |
| 2006/0205863 A1 | 9/2006 | Lin et al. | |

FOREIGN PATENT DOCUMENTS

| | | | |
|---|---|---|---|
| DE | 1769723 | 10/1972 | |
| DE | 3244499 | 6/1983 | |
| DE | 1961981 | 9/1997 | |
| EP | 0 046 536 | 3/1982 | |
| EP | 0 087 294 | 8/1983 | |
| EP | 0 210 733 | 2/1987 | |
| EP | 0 300 689 | 7/1988 | |
| EP | 0 315 363 | 10/1988 | |
| EP | 0 300 682 | 1/1989 | |
| EP | 0 315 481 | 5/1989 | |
| EP | 0 322 169 | 6/1989 | |
| EP | 0 343 943 | 11/1989 | |
| EP | 0 407 098 | 1/1991 | |
| EP | 0 448 259 | 3/1991 | |
| EP | 0 428 153 | 5/1991 | |
| EP | 0 431 475 | 6/1991 | |
| EP | 0 476 401 | 3/1992 | |
| EP | 0 476 700 | 3/1992 | |
| EP | 0 477 748 | 4/1992 | |
| EP | 0 682 074 | 11/1995 | |
| EP | 0 699 519 | 3/1996 | |
| EP | 0 716 124 | 6/1996 | |
| EP | 0 755 970 | 1/1997 | |
| EP | 0 757 076 | 2/1997 | |
| EP | 0 827 526 | 3/1998 | |
| EP | 0 886 656 | 12/1998 | |
| EP | 0 902 051 | 3/1999 | |
| EP | 1 028 145 | 2/2000 | |
| EP | 1 211 285 | 4/2001 | |
| EP | 1 138 478 | 10/2001 | |
| EP | 1 214 386 | 6/2002 | |
| EP | 1 252 231 | 10/2002 | |
| EP | 1 342 249 | 1/2009 | |
| FR | 2 094 870 | 12/1970 | |
| GB | 0 511 319 | 8/1939 | |
| GB | 0 511 320 | 8/1939 | |
| GB | 964 845 | 7/1964 | |
| GB | 1068783 | 5/1967 | |
| GB | 1 329 915 | 9/1973 | |
| GB | 2 195 642 | 7/1987 | |
| JP | 69-029554 | 1/1968 | |
| JP | 74-041101 | 11/1974 | |
| JP | 56-095938 | 3/1981 | |
| JP | 01-192365 | 8/1989 | |
| JP | 01-282280 | 11/1989 | |
| JP | 04 063 851 | 2/1992 | |
| JP | 04-214709 | 5/1992 | |
| JP | WO 92/14784 | 9/1992 | |
| JP | 05-202339 | 8/1993 | |
| JP | 6-1892 | * 1/1994 | |

| | | |
|---|---|---|
| JP | 07-292167 | 7/1995 |
| JP | 07-292167 | 11/1995 |
| JP | 08 269 417 | 10/1996 |
| JP | 34 74677 | 1/1997 |
| JP | 09-076260 | 3/1997 |
| JP | 09 077901 | 3/1997 |
| JP | 9-208761 * | 8/1997 |
| JP | 09-208761 | 12/1997 |
| JP | 10 036 569 | 2/1998 |
| JP | 10-168252 | 6/1998 |
| JP | 11 049 903 | 2/1999 |
| JP | 2001/106628 | 4/2001 |
| JP | 2002/038114 | 2/2002 |
| SU | 455976 | 5/1975 |
| WO | WO 91/18045 | 11/1991 |
| WO | WO 97/33921 | 9/1997 |
| WO | WO 98/44041 | 10/1998 |
| WO | WO 98/44041 A1 * | 10/1998 |
| WO | WO 98/46694 | 10/1998 |
| WO | WO 99/24501 | 5/1999 |
| WO | WO 00/01745 | 1/2000 |
| WO | WO 01/18109 | 3/2001 |
| WO | WO 02/18487 | 3/2002 |
| WO | WO 02/30194 | 4/2002 |
| WO | WO 02/31044 | 4/2002 |
| WO | WO 02/31044 A1 * | 4/2002 |
| WO | WO 02/100153 | 12/2002 |
| WO | WO 03/048252 | 6/2003 |
| WO | WO 2004/009699 | 1/2004 |
| WO | WO 2004/014997 | 2/2004 |
| WO | WO 2004/014998 | 2/2004 |
| WO | WO 2004/020195 | 3/2004 |
| WO | WO 2005/080495 | 9/2005 |
| WO | WO 2006/006346 | 1/2006 |

OTHER PUBLICATIONS

Parapol 450 technical data sheet, copyright 2000-2004.*
Neste Oil PolyAlphaOlefins, Nexbase 2004, technical data sheet, copyright 2002.*
Renkert Oil Nexbase 2000 series, technical data sheet, copyright 2002.*
Chevron Phillips "Safe Handling and Storage of Polyalphaolefins (PAO)" copyright 2005.*
JP 9-208761 (Aug. 1997) abstract and translation in English.*
Lucant HC-40 material data sheet (available at http://www.matweb.com/search/datasheettext.aspx?matid=53279), copyright 1996-2008.*
U.S. Appl. No. 11/118,925, filed Apr. 29, 2005.
U.S. Appl. No. 60/649,266, filed Feb. 2, 2005, Wang et al.
U.S. Appl. No. 60/699,718, filed Jul. 15, 2005.
Hofmann, W., "Rubber Chemicals and Additives", Rubber Technology Handbook, pp. 294-305, 1989.
Radian Corporation, "Plasticizers", Chemical Additives for the Plastics Industry, Noyes Data Corporation, NJ pp. 107-116, 1987.
Stepek, J et al.; "Additives for Plastics", Springer Verlag, pp. 1-69, 1983.
Rudniek L, et al.; "Synthetic Lubricants and High-Performance Functional Fluids", Second Edition, Revised and Expanded, Marcel Dekker, Inc., pp. 409-411, 1999.
Khungar, S.L.; "Flexible Films of Polypropylene Plasticized with Polybutenes", Amoco Chemicals, pp. 2992-2996, 1996.
Pratt, C.F. et al.; "Control of Phase Separation and Voiding in Oil-Filled Polypropylene", Journal of Applied Polymers Science, Vo. 18, pp. 3621-3631, 1974.
Nitta, K. et al.; "Plasticizing of isotactic polypropylene upon addition of hydrocarbon oils", e-Polymers, vol. 021, pp. 1-11, 2004.
Gedeon, B. et al.; "Use of "Clean" Paraffinic Processing Oils to Improve", Paralux Articles, Presented at TPEs 2000, pp. 1-10, 2000.
Hawley's Condensed Chem. Dic., $14^{th}$ Ed. (2001), p. 835.
Parapol 450: Product information and data sheet, found online at: http://www.infochems.com/chemdb/product_content.asp?product_id=42969, Copyright 2000-2004.
Parapol 950: Product information and data sheet, found online at: http://www.infochems.com/chemdb/product_content.asp?product_id=42981<ype=search&list=all&inx=all&search_option=trade_name&search_keyword=parapol%20950&lorder=regi_d ate&page=1, Copyright 2000-2004.
Dharmarajan et al. "Modifying Polypropylene with a Metallocene Plastomer"; Plastics Engr.; Aug. 1996; pp. 33-35.
Maier, C.; Calafut, T. (1998), Propylene—The Definitive User's Guide and Databook, (pp. 11-25 and 97-106), William Andrew Publishing/Plastics Design Library, Online version available at: http://www.knovel.com/knovel2/Toc.jsp?BookID=54&VerticalID=0.
Jens Stehr, Investigation of the Effects of Poly(α-olefin) Plasticizers on the Properties of Elastomers, KGK, Jan./Feb. 2007, pp. 14-19 (translated from German by McElroy Translation Company.

* cited by examiner

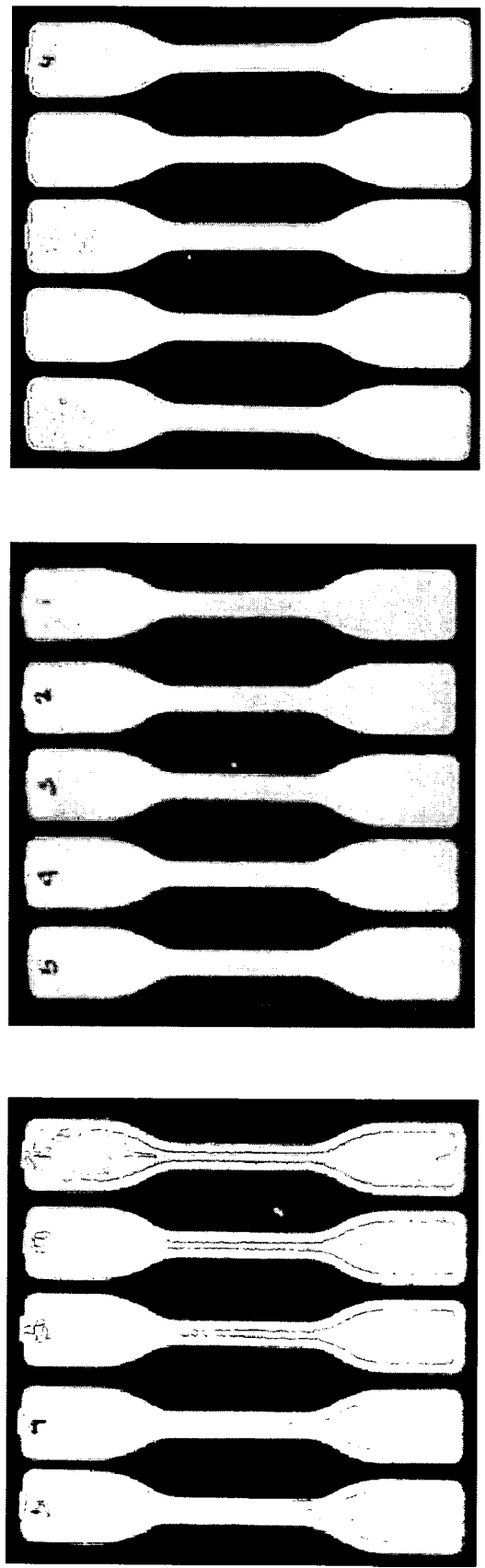

e) with NA-D added (Example 16)

d) with NA-C added (Example 12)

ARTICLES FROM PLASTICIZED THERMOPLASTIC POLYOLEFIN COMPOSITIONS

PRIORITY CLAIM

This application is a continuation in part of U.S. Ser. No. 10/640,435, filed Aug. 12, 2003 which claims the benefit of U.S. Ser. No. 60/402,665 filed on Aug. 12, 2002. This application is also a continuation in part of U.S. Ser. No. 10/634, 351 filed Aug. 4, 2003 which claims the benefit of U.S. Ser. No. 60/402,665 filed on Aug. 12, 2002.

FIELD OF THE INVENTION

The present invention relates to articles produced from plasticized thermoplastic polyolefins comprising a thermoplastic polyolefin, a non-functionalized plasticizer (NFP), and a nucleating agent (NA).

BACKGROUND OF THE INVENTION

Polyolefins, namely polyolefin plastics and elastomers, are useful in any number of everyday articles. Semicrystalline polyolefins, in particular, are used in such applications because they are thermoplastic, meaning, among other things, that they exhibit some useful degree of crystallinity in the solid state. This crystalline nature allows them to form useful articles without crosslinking due to favorable combination of processing characteristics, physical properties, and aesthetics. For example, such materials can be formed into pellets for ease of handling and are processed using standard plastic-industry equipment such as extruders. Thermoplastic polyolefins are fundamentally different from polyolefin thermoset materials, such as ethylene-propylene elastomers or rubbers, including ethylene-propylene-diene monomer (EPDM) versions, which have little to no crystallinity, very high molecular weights, and are typically cross-linked to form useful articles. Such materials are generally not pelletizable and are processed using standard rubber-industry equipment such as roll mills.

However, one drawback to many thermoplastic polyolefins, especially propylene-rich ones, is their relatively high glass transition temperature. This characteristic makes these polyolefins brittle, especially at low temperatures. Many applications of thermoplastic polyolefins benefit from having useful properties over a broad range of temperatures; consequently, there is a need to provide polyolefins that can maintain desirable characteristics such as high or low temperature performance, etc., while maintaining or improving upon the impact strength and toughness at lower temperatures. In particular, it would be advantageous to provide thermoplastic polyolefins possessing improved toughness, flexibility, and or high use temperature without sacrificing their other desirable properties, including optical properties such as high clarity and low haze. Preferably, the thermoplastic polyolefin will also exhibit high crystallization temperature and high crystallization rate, to allow fast processing. Furthermore, articles fabricated from the thermoplastic polyolefin should have high clarity, low haze, and good surface aesthetics, particularly without oily or sticky substances on the surface.

Specifically, there is a need for thermoplastic polyolefin compositions, especially polypropylene and polyethylene compositions, that can be used in such applications as food containers, health care products, durable household and office goods, squeeze bottles, clear flexible film and sheet, automotive interior trim and fascia, wire, cable, pipe, and toys. Even more specifically, a thermoplastic polyolefin composition with clear, homogenous appearance after molding is needed. A plasticized polyolefin according to this invention can fulfill these needs.

Addition of a low molecular weight, amorphous substance to a polyolefin is one way to modify its properties and processing characteristics. Some patent disclosures directed to such an end are U.S. Pat. Nos. 3,201,364; 3,415,925; 4,073, 782; 4,110,185; 4,132,698; 4,210,570; 4,325,850; 4,960,820; 4,774,277; 5,869,555; 6,465,109; EP 0448259, FR 2094870, and JP 09-208761. These disclosures are directed to polyolefins blended with materials such as mineral oils which often contain substantial concentrations of unsaturation, aromatic groups, naphthenic groups, and/or other functional groups. Addition of mineral oils in polyolefin elastomers, which have little to no crystallinity and very high molecular weights, is also well known; see e.g., RUBBER TECHNOLOGY HANDBOOK, Werner Hoffman (Hanser, N.Y., 1989), p. 294-305.

Addition of mineral oil tends to improve the flexibility of a polyolefin, which identifies such compounds as "plasticizers" under the commonly accepted definition; that is, a substance that improves the flexibility, workability, or distensibility of a plastic or elastomer. Mineral oils are also added to polyolefins as extender oils or processing oils, as well as for other purposes. However, use of these additive compounds often does not preserve the optical properties (e.g., color and/or transparency), or low odor, or upper (lower) use temperature ranges of the polyolefin, among other things. In addition, such additive compounds typically have high pour points (greater than $-20°$ C., or even greater than $-10°$ C.), resulting in little or no improvement in low temperature properties of the polyolefin. Another drawback is that all or some of the mineral oil can migrate to a surface and evaporate at an unacceptably high rate, which results in deterioration of properties over time, among other things. If the flash point is sufficiently low (e.g., less than 200° C.), the compound can cause smoking and be lost to the atmosphere during melt processing. It can also leach out of the polyolefin and impair food, clothing, and other articles that are in contact with the final article made from the polyolefin composition. It can also cause problems with tackiness or other surface properties of the final article. What is needed is a compound which imparts superior low temperature properties while also exhibiting low bloom, migration, leaching, and/or evaporation behaviors.

Yet another shortcoming of mineral oils is that they often contain a high (greater than 5 wt %) degree of functionality due to carbon unsaturation and/or heteroatoms, which tends to make them reactive, thermally unstable, and/or incompatible with polyolefins, among other things. Mineral oils may in fact contain thousands of different compounds, many of which are undesirable for use in polyolefins due to molecular weight or chemical composition. Under moderate to high temperatures these compounds can volatilize and oxidize, even with the addition of oxidation inhibitors. They can also lead to problems during melt processing and fabrication steps, including degradation of molecular weight, cross-linking, or discoloration. They may also impart an undesirable odor.

These attributes of common additive compounds like mineral oils limit the performance of the final polyolefin composition, and therefore its usefulness in many applications. As a result, they are not highly desirable for use as modifiers for thermoplastic polyolefins. What is needed is a modifier that does not suffer from these deficiencies. Preferably, what is needed is a modifier that allows the formulation of thermoplastic polyolefin compositions with improved softness, flexibility (lower flexural modulus), and impact toughness especially at low temperatures (below 0° C.), while not materially degrading the thermal resistance and with minimal migration of low molecular weight substances to the surface of fabricated articles. Ideally, the modifier would have a low pour point, while still of sufficient molecular weight to avoid unacceptable exudation and extraction. It would also not contribute to deterioration of performance attributes such as optical properties, color, smell, thermal stability, and/or oxidative stability. Preferably, the glass transition temperature of the modified polyolefin composition would be lower than that of the unmodified polyolefin. A plasticized composition according to this invention can fulfill these needs.

It would be particularly desirable to modify thermoplastic polyolefins by addition of a simple, non-reactive compound such as paraffin liquid. However, it has been taught that addition of aliphatic or paraffinic compounds impairs the properties of polyolefins, and is thus not recommended; see, e.g., CHEMICAL ADDITIVES FOR PLASTICS INDUSTRY (1987, Radian Corp., Noyes Data Corporation, NJ), p. 107-116. Other background references of interest include U.S. Pat. No. 6,639,020 and ADDITIVES FOR PLASTICS, J. Stepek, H. Daoust (Springer Verlag, New York, 1983), p. 6-69.

Certain mineral oils, distinguished by their viscosity indices and the amount of saturates and sulfur they contain, have been classified as Hydrocarbon Basestock Group I, II or III by the American Petroleum Institute (API). Group I basestocks are solvent refined mineral oils. They contain the most unsaturates and sulfur and have the lowest viscosity indices. They define the bottom tier of lubricant performance. Group I basestocks are the least expensive to produce, and they currently account for abut 75 percent of all basestocks. These comprise the bulk of the "conventional" basestocks. Groups II and III are the High Viscosity Index and Very High Viscosity Index basestocks. They are hydroprocessed mineral oils. The Group III oils contain less unsaturates and sulfur than the Group I oils and have higher viscosity indices than the Group II oils do. Additional basestocks, named Groups IV and V, are also used in the basestock industry. The five basestock groups are described, for example in SYNTHETIC LUBRICANTS AND HIGH-PERFORMANCE FUNCTIONAL FLUIDS (Leslie R. Rudnick & Ronald L. Shubkin, ed. Marcel Dekker, Inc. 1999; p. 409) as being:

Group I—mineral oils refined using solvent extraction of aromatics, solvent dewaxing, hydrofining to reduce sulfur content; produces mineral oils with sulfur levels typically greater than 0.1%, saturates levels of 60-80%, and viscosity index (VI) of about 90;

Group II—mildly hydrocracked mineral oils with conventional solvent extraction of aromatics, solvent dewaxing, and more severe hydrofining to reduce sulfur levels to less than or equal to 0.1% (typically 0.03%) as well as removing double bonds from some of the olefinic and aromatic compounds; saturate levels are greater than 95-98%, and VI is approximately 90-100;

Group III—severely hydrotreated mineral oils with saturates levels of some oils virtually 100%; sulfur contents are between 0.001 and 0.01%, and VI is in excess of 120;

Group IV—poly(alpha-olefin)s—synthetic fluids most commonly manufactured by catalytic oligomerization of linear olefins having 6 or more carbon atoms, but more generally meaning saturated olefin oligomers produced by oligomerizing $C_4$ and greater alphaolefins; and Group V—esters, polyethers, polyalkylene glycols, etc.—generally, all other synthetic basestocks not included in Groups I, II, III and IV.

Prior attempts of adding mineral oils to polyolefins to modify properties involve for the most part addition of Group I and Group II mineral oils. Even in cases where the mineral oil is not identified by an API Group classification, such as the case for so-called "process oils," "technical white oils," "food grade oils," etc., such mineral oils are still readily categorized into two classes based on VI alone: those with VI less than 120 (similar to Group I and Group II mineral oils), and those with VI of 120 or greater. Certain aspects of the present invention ideally pertain to substances with a VI of 120 or greater, which excludes Group I and Group II mineral oils and any other mineral oils with VI less than 120.

Examples of thermoplastic polyolefins combined with paraffinic liquid plasticizers for non-adhesive applications include the following:

U.S. Pat. No. 4,536,537 discloses polypropylene compositions that comprise LLDPE having a density of 0.912 to 0.935 g/cm$^3$ or polybutene and poly-α-olefin liquid having a kinematic viscosity of about 2 cSt to about 6 cSt at 100° F./38° C.; those with viscosity greater than about 2 cSt are reported to "not work" (col 3, ln 12).

WO 98/44041 discloses blend compositions that comprise a chlorine-free polyolefin and poly-α-olefin oligomers having a kinematic viscosity at 100° C. of about 4 cSt to about 8 cSt for a sheet-like structure, especially a floor covering.

WO 2002/18487 and WO 2003/48252 disclose polypropylene compositions that comprise 10 to 30 wt % of vulcanized or unvulcanized polyolefin elastomers, especially EPDM or styrene-ethylene-butene-styrene (SEBS) block-copolymers, and poly-α-olefin oligomers having a kinematic viscosity at 100° C. of about 4 cSt to about 8 cSt.

U.S. Pat. No. 4,645,791, JP 07292167, EP 0315363, and WO 2002/31044 all disclose poly-α-olefin type materials in EPDM compositions.

JP 56095938 discloses polypropylene compositions that comprise olefin oligomer plasticizers mixed with polyolefin granules.

WO 2004/14998 discloses propylene-based polymer compositions that comprise various plasticizers, including poly-alpha-olefins. Some compositions contain a nucleating agent.

In another area, paraffins and traditional lubricant basestocks have recently been used as polymer modifiers. WO 2004/014997, US 2004/054040 (U.S. Ser. No. 10/634,351), WO 2004/014998 (also noted above), and US 2004/106723 (U.S. Ser. No. 10/640,435) disclose blends of polyolefins such as polypropylene and or polybutene with various liquids (such as isoparaffins, n-paraffins, polyalphaolefins, highly refined Group III basestocks, polybutenes, Gas-To-Liquid type molecules, and others) used as non-functional plasticizers (NFP's). These compositions are reported to have superior properties, such as good flex and stiffness combinations as well as low exudation of the NFP. Other examples of NFP materials used as plasticizers in many applications include WO 2005/080495; US 2005/148720 (U.S. Ser. No. 11/054, 247); US 2004/0260001 (U.S. Ser. No. 10/782,228); US 2004/0186214 (U.S. Ser. No. 10/782,306); U.S. Ser. No. 60/649,266 filed Feb. 2, 2005; U.S. Ser. Nos. 11/118,925, 11/119,072, and 11/119,193, all filed Apr. 29, 2005; U.S. Ser. No. 60/649,107 filed Jun. 24, 2005; GB 0511319.6 and GB 0511320.4, both filed Jun. 3, 2005; and U.S. Ser. No. 60/699, 718 filed Jul. 15, 2005.

Other references of interest include: GB 1329915; JP 01282280, JP 69029554, WO 2001/18109; EP 0300689; and EP 1028145.

The above examples show that certain paraffinic liquid plasticizers modify the properties (e.g., flexibility and low-temperature impact strength) of polyolefins, in particular polypropylene. However, it has been found that, under certain conditions, plasticization causes certain types of thermoplastic polyolefins, especially polypropylene, to exhibit undesirable optical and/or tactile properties. For example, isotactic polypropylene can develop a distinct hazy region in the interior of injection-molded specimens after aging (seconds to minutes); and random copolymer polypropylene can develop an oily feel on the surface of compression-molded specimens after aging (hours to days). Under an optical microscope, a hazy region contains an inhomogeneous and irregular distribution of amorphous domains, likely rich in the liquid plasticizer, that are large enough to scatter light. Similarly, an oily feel is likely due to a plasticizer-rich layer on the surface. The conditions required for the onset of undesirable optical and/or tactile behavior depend on the nature of the molding process, the type of polyolefin, the type of plasticizer, and the concentration of plasticizer (typically, a concentration higher than some critical level). What is needed is a means to modify the plasticized composition so as to ensure satisfactory aesthetics in a molded article.

Addition of a nucleating agent to the thermoplastic polyolefin/plasticizer blend, as demonstrated in the present invention, satisfies this need. Specifically, appropriate selection and use of a nucleating agent increases the robustness of the plasticization process, which allows for increased plasticizer concentrations (and therefore greater modification of mechanical properties and processing characteristics) without the appearance of internal haze or surface oiliness, thereby retaining acceptable optical and tactile properties.

SUMMARY OF THE INVENTION

This invention relates to articles comprising plasticized thermoplastic polyolefin compositions comprising one or more thermoplastic polyolefins, one or more non-functionalized plasticizers ("NFP"), and one or more a nucleating agents.

DEFINITIONS

Figure 1:
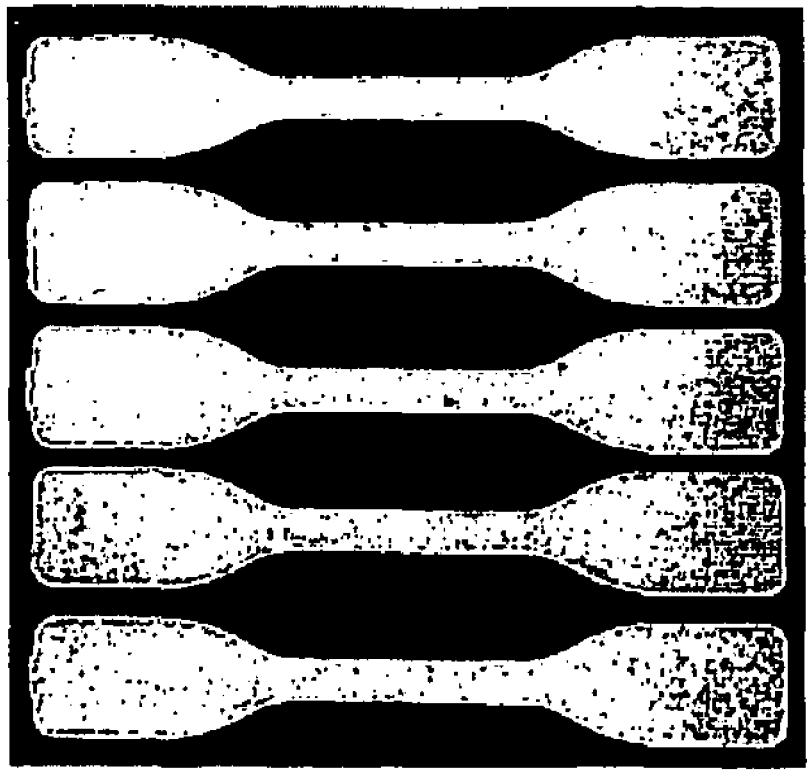
FIG. 1 is a series of photographs demonstrating the effect of nucleating agent (NA) on the haziness of injection molded specimens with 10 wt % of a particular NFP.
Figure 1:
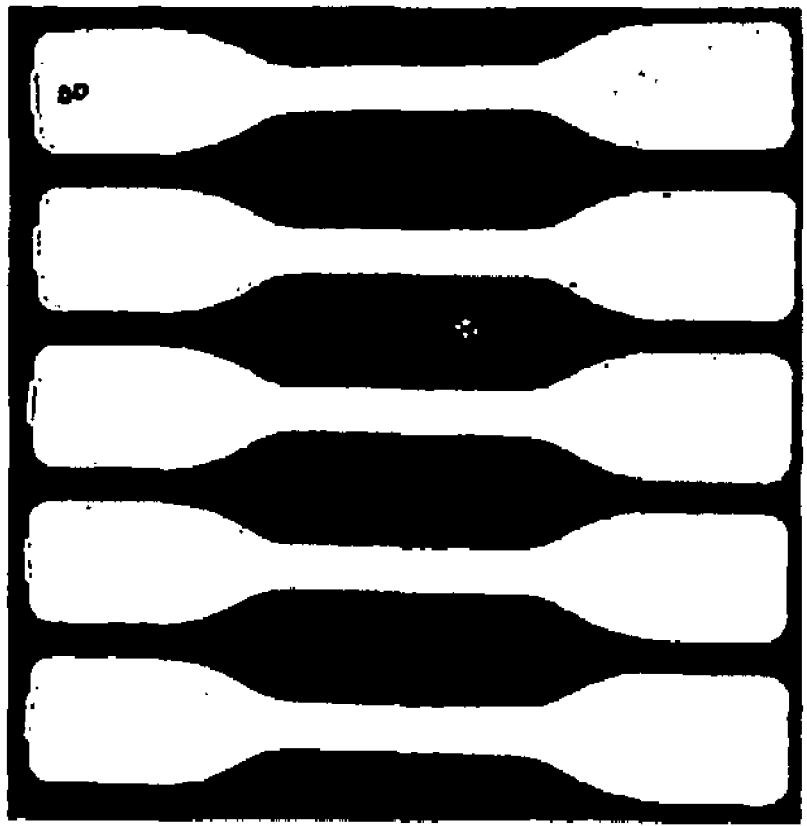

For purposes of this invention and the claims thereto when a polymer or oligomer is referred to as comprising an olefin, the olefin present in the polymer or oligomer is the polymerized or oligomerized form of the olefin, respectively. Likewise the use of the term polymer is meant to encompass homopolymers and copolymers. In addition the term copolymer includes any polymer having 2 or more chemically distinct monomers, and encompasses interpolymers and block copolymers of 2 or more chemically distinct monomer types.

For purposes of this invention and the claims thereto, a polyolefin is defined to be a polymer with at least 50 mol % (preferably at least 60 mol %, preferably at least 70 mol %, preferably at least 80 mol %, preferably at least 90 mol %, preferably at least 95 mol %, preferably 100 mol %) of one or more olefin monomers, preferably 1-olefins, having carbon numbers of 2 to 20 (preferably 2 to 16, preferably 2 to 10, preferably 2 to 8, preferably 2 to 6) and have a number-average molecular weight ($M_n$) of 20 kg/mol or more (preferably 25 kg/mol or more, preferably 30 kg/mol or more, preferably 40 kg/mol or more, preferably 50 kg/mol or more, preferably 80 kg/mol or more, preferably 100 kg/mol or more).

Thus, as used herein, the terms "polypropylene" and "propylene polymer" mean a polymer made of at least 50 mole % (preferably at least 60 mole %, more preferably at least 70 mole %, more preferably at least 80 mole %, even more preferably at least 90 mole %, even more preferably at least 95 mole % or preferably 100 mole %) propylene units; and having less than 35 wt % ethylene units. Thus, a propylene polymer as it is defined here can not be an EP Rubber as defined below. The comonomers in a propylene copolymer are preferably chosen from among ethylene and $C_4$ to $C_{24}$ olefins. As used herein, the term "polypropylene" encompasses so-called random copolymer polypropylene (RCP), isotactic polypropylene (iPP), syndiotactic polypropylene (sPP), and homopolypropylene (hPP). As used herein, the term "polypropylene blend" means a blend of two or more polymers comprising at least one polypropylene component, where the overall propylene content of the blend is at least 50 wt % (preferably at least 60 wt %, preferably at least 70 wt %, preferably at least 80 wt %, preferably at least 90 wt %), based on the total weight of the blend. Thus, as used herein, "polypropylene blend" encompasses impact copolymers, preferably in-situ (also known as in-reactor) blended impact copolymers, as well as blends with other synthetic polymers, preferably other polyolefins, preferably other ethylene or propylene or butene polymers including optionally polyolefin elastomers.

Also, as used herein, the terms "polyethylene" and "ethylene polymer" mean a polymer made of at least 50 mole % (preferably at least 60 mole %, more preferably at least 70 mole %, more preferably at least 80 mole %, even more preferably at least 90 mole %, even more preferably at least 95 mole % or preferably 100 mole %) ethylene units; and having less than 20 wt % propylene units. Thus, an ethylene polymer as it is defined here can not be an EP Rubber as defined below. The comonomers in an ethylene copolymer are preferably chosen from among $C_3$ to $C_{24}$ olefins. As used herein, the term "polyethylene blend" means a blend with at least one polyethylene component, where the overall ethylene content of the blend is at least 50 wt % (preferably at least 60 wt %, preferably at least 70 wt %, preferably at least 80 wt %, preferably at least 90 wt %), based on the total weight of the blend. Thus, as used herein, "polyethylene blend" encompasses blends with other synthetic polymers, preferably other polyolefins, preferably other ethylene or propylene or butene polymers, including optionally polyolefin elastomers.

For purposes of this invention and the claims thereto, an ethylene polymer having a density of less than 0.86 g/cm³ is referred to as an ethylene elastomer; an ethylene polymer having a density of 0.86 to 0.910 g/cm³ is referred to as an ethylene plastomer or simply a plastomer; an ethylene polymer having a density of greater than 0.910 to 0.940 g/cm³ is referred to as a low density polyethylene (LDPE), which includes linear low density polyethylene (LLDPE) and other ethylene polymers in this density range made using a heterogeneous catalysis process or made in a high-pressure/free radical catalysis process; and an ethylene polymer having a density of more than 0.940 g/cm³ is referred to as a high density polyethylene (HDPE).

Also, as used herein, the terms "polybutene" and "butene polymer" mean a polymer made of at least 50 mole % (preferably at least 60 mole %, more preferably at least 70 mole %, more preferably at least 80 mole %, even more preferably at least 90 mole %, even more preferably at least 95 mole % or preferably 100 mole %) butene-1 units. The comonomers in a butene copolymer are preferably chosen from among ethylene, propylene, and $C_5$ to $C_{24}$ olefins. As used herein, the term "polybutene blend" means a blend with at least one polybutene component, where the overall polybutene content of the blend is at least 50 wt % (preferably at least 60 wt %, preferably at least 70 wt %, preferably at least 80 wt %, preferably at least 90 wt %), based on the total weight of the blend. Thus, as used herein, "polybutene blend" encompasses blends with other synthetic polymers, preferably other polyolefins, preferably other ethylene or propylene or butene polymers, including optionally polyolefin elastomers.

For purposes of this invention and the claims thereto, an EP Rubber is defined to be a copolymer of ethylene and propylene, and optionally diene monomer(s), where the ethylene content is from 35 to 80 wt %, the diene content is 0 to 15 wt %, and the balance is propylene with a minimum propylene content of 20 wt %; and where the copolymer has a Mooney viscosity, ML(1+4) @ 125° C. (measured according to ASTM D1646) of 15 to 100.

For purposes of this invention and the claims thereto, an oligomer is defined to have a number-average molecular weight ($M_n$) of less than 20 kg/mol (preferably less than 15 kg/mol, preferably less than 13 kg/mol, preferably less than 10 kg/mol, preferably less than 5 kg/mol, preferably less than 4 kg/mol, preferably less than 3 kg/mol, preferably less than 2 kg/mol, preferably less than 1 kg/mol).

For purposes of this invention and the claims thereto, a liquid is defined to be a material that flows at room temperature (23° C.), having a pour point of less than 25° C. with no melting point above 0° C. and a kinematic viscosity at 25° C. of 30,000 cSt or less.

For purposes of this invention and the claims thereto, the term paraffin includes all isomers such as normal paraffins (n-paraffins), branched paraffins, isoparaffins, cycloparaffins, and may include cyclic aliphatic species, and blends thereof, and may be derived synthetically by means known in the art, or from refined crude oil in such a way as to meet the requirements described for desirable modifiers described herein. The term isoparaffin means that the paraffin chains possess $C_1$ to $C_{18}$ (more commonly $C_1$ to $C_{10}$) alkyl branching along at least a portion of each paraffin chain. More particularly, isoparaffins are saturated aliphatic hydrocarbons whose molecules have at least one carbon atom bonded to at least three other carbon atoms or at least one side chain (i.e., a molecule having one or more tertiary or quaternary carbon atoms); various isomers of each carbon number (i.e., structural isomers) will typically be present. Isoparaffins with multiple alkyl branches may include any combination of regio and stereo placement of those branches.

For purposes of this invention and the claims thereto Group I, II, and III basestocks (i.e., lubricant basestocks refined from crude oil) are defined to be mineral oils having the following properties:

|  | Saturates (wt %) |  | Sulfur (wt %) |  | Viscosity Index |
|---|---|---|---|---|---|
| Group I | <90 | and/or | >0.03% | and | 80-119.9 |
| Group II | ≧90 | and | ≦0.03% | and | 80-119.9 |
| Group III | ≧90 | and | ≦0.03% | and | ≧120 |

Saturates content, sulfur content, and Viscosity Index are measured following ASTM D 2007, ASTM D 2622, and ASTM D 2270, respectively. Even if a mineral oil is not specifically or historically identified by a Group classification, it is still possible to categorize it into one of two classes based on Viscosity Index: Group III mineral oils which have VI of 120 or more, or not Group III (i.e., Group I or II) mineral oils which have VI less than 120.

For purposes of this invention and the claims thereto, a Group IV basestock (i.e., lubricant basestock) is defined to be a polyalphaolefin liquid (or simply a PAO), which is further defined to be a liquid comprising hydrocarbon oligomers manufactured by the catalytic oligomerization of alpha-olefins, preferably linear alpha-olefins, having 5 to 24 carbon atoms, preferably 5 to 20 carbon atoms, more preferably 6 to 18 carbon atoms. A PAO may be characterized by any type of tacticity, including isotactic or syndiotactic and/or atactic, and by any degree of tacticity, including isotactic-rich or syndiotactic-rich or fully atactic; that is, the ratio of meso to racemic diads ([m]/[r]) determined by $^{13}$C-NMR can be 1, greater than 1, or less than 1.

For purposes of the present invention and the claims thereto, the term mineral oil includes any petroleum-based oil; derived from petroleum crude oil that has been subjected to refining steps (such as distillation, solvent processing, hydroprocessing, and/or dewaxing) to achieve the final oil. This also includes petroleum-based oils that are extensively purified and/or modified through severe processing treatments. It excludes synthetic oils, which have been manufactured by combining monomer units using catalysts and/or heat. In the polymer processing art, mineral oils are often called process oils. Characteristics of some commercially available mineral oils (so-called "paraffinic" mineral oils) used as process oils in polymers are listed in Table A; all these fluids have a viscosity index less than 120, most have a viscosity index less than 110, and many have a viscosity index of 100 or less; therefore these materials can not be classified as Group III mineral oils. Furthermore, all have less than 80% carbons in paraffinic chain-like structures (denoted $C_P$ in the art), meaning they also all have more than 20% carbons in aromatic and/or naphthenic ring-like structures ($C_A+C_N$).

TABLE A

Commercial Examples of Paraffinic Mineral Oils

|  | KV @ 100° C. cSt | KV @ 40° C. cSt | VI | Pour Point ° C. | Specific gravity | Flash Point ° C. | APHA Color | $C_P$% |
|---|---|---|---|---|---|---|---|---|
| Drakeol 34[1] | 9 | 76 | 99 | −12 | 0.872 | 254 | 10 | 68 |
| Paralux 1001R[2] | 4 | 20 | 99 | −17 | 0.849 | 212 | 25 | 68 |
| Paralux 2401R[2] | 6 | 43 | 101 | −12 | 0.863 | 234 | 45 | 66 |
| Paralux 6001R[2] | 12 | 118 | 102 | −21 | 0.871 | 274 | 45 | 69 |
| Sunpar 120[3] | 6 | 41 | 106 | −15 | 0.872 | 228 |  | 68 |
| Sunpar 150[3] | 11 | 94 | 97 | −9 | 0.881 | 245 | >300 | 65 |
| Sunpar 2280[3] | 31 | 475 | 95 | −9 | 0.899 | 305 | >300 | 67 |
| Plastol 135[4] | 5 | 24 | 104 | −9 | 0.865 | 210 | 10 | 67 |
| Plastol 537[4] | 11 | 103 | 97 | −3 | 0.880 | 240 | 10 | 66 |

TABLE A-continued

Commercial Examples of Paraffinic Mineral Oils

| | KV @ 100° C. cSt | KV @ 40° C. cSt | VI | Pour Point ° C. | Specific gravity | Flash Point ° C. | APHA Color | $C_P$ % |
|---|---|---|---|---|---|---|---|---|
| Plastol 2105[4] | 30 | 380 | 110 | −15 | 0.885 | 270 | 10 | |
| Flexon 843[4] | 5 | 30 | 91 | −12 | 0.869 | 218 | >250 | 65 |
| Flexon 865[4] | 11 | 106 | 93 | −3 | 0.879 | 252 | >250 | 69 |
| Flexon 815[4] | 32 | 457 | 101 | −9 | 0.895 | 310 | >300 | 67 |
| Shellflex 210[5] | 4 | 19 | 95 | −18 | 0.860 | 216 | >200 | 66 |
| Shellflex 330[5] | 9 | 70 | 95 | −10 | 0.875 | 256 | >250 | 68 |
| Shellflex 810[5] | 33 | 501 | 95 | −9 | 0.896 | 324 | >300 | 69 |
| Diana PW32[6] | 5 | 31 | 104 | −18 | 0.862 | 226 | 10 | 67 |
| Diana PW90[6] | 11 | 90 | 105 | −15 | 0.870 | 272 | 10 | 71 |
| Diana PW150[6] | | 145 | | −15 | 0.872 | 270 | 10 | 72 |
| Diana PW380[6] | 29 | 384 | 106 | −10 | 0.880 | 296 | 10 | 73 |

[1]Available from Penreco (USA).
[2]Available from Chevron (USA).
[3]Available from Sunoco (USA).
[4]Available from ExxonMobil (USA).
[5]Available from Royal Dutch Shell (UK/Netherlands).
[6]Available from Idemitsu (Japan).

For purposes of this invention and the claims thereto, a nucleating agent is defined as an organic or inorganic substance that, when added to a thermoplastic polyolefin (preferably chosen from among polypropylene and polypropylene blends) at a concentration in a range of 0.01 to 10 wt %, increases the crystallization temperature by at least 5° C. as determined by differential scanning calorimetry at a cooling rate of 10° C./min.

For purposes of this invention and the claims thereto, "thermoplastic polyolefin" means that the polyolefin has a melting temperature of 30° C. or more (preferably 40° C. or more, preferably 50° C. or more, preferably 60° C. or more, preferably 80° C. or more, preferably 100° C. or more), and a heat of fusion as measured by DSC of 5 J/g or more (preferably 10 J/g or more, preferably 20 J/g or more, preferably 30 J/g or more, preferably 50 J/g or more).

For purposes of this invention and the claims thereto, by elastomers is meant all natural and synthetic rubbers, including those defined in ASTM D1566.

For purposes of this invention and the claims thereto, the nomenclature "$C_z$" where z is an integer means there are "z carbons" in the compound; for example, a "$C_5$ paraffin" is a paraffin with 5 carbon atoms.

For purpose of this invention and the claims thereto, unless otherwise noted, the following tests shall be used for the indicated property:

TABLE B1

Polyolefin Characterization Test Methods

| | |
|---|---|
| Melt Index (MI) | ASTM D 1238 (190° C./2.16 kg) |
| Melt Flow Rate (MFR) | ASTM D 1238 (230° C./2.16 kg) |
| Density | ASTM D 1505 |
| Glass Transition Temperature ($T_g$) | DMTA (see Experimental Methods) |
| Melting Point ($T_m$) | DSC (see Experimental Methods) |
| Crystallization Point ($T_c$) | DSC (see Experimental Methods) |
| Heat of Fusion ($H_f$) | DSC (see Experimental Methods) |
| % Crystallinity | DSC (see Experimental Methods) |
| $M_n$ and $M_w$ | SEC-3D (see Experimental Methods) |
| Branching Index (g') | SEC-3D (see Experimental Methods) |
| Intrinsic Viscosity | ASTM D 1601 (135° C. in decalin) |

TABLE B2

Mechanical Property Test Methods

| | |
|---|---|
| Tensile Properties | ASTM D 638 |
| Heat Deflection Temperature | ASTM D 648 (66 psi) |
| Vicat Softening Temperature | ASTM D 1525 (200 g) |
| Gardner Impact Strength | ASTM D 5420 |
| Izod Impact Strength | ASTM D 256 (A) |
| 1% Secant Flexural Modulus | ASTM D 790 (A) |
| Rockwell Hardness | ASTM D 785 (R scale) |

TABLE B3

NFP Property Test Methods

| | |
|---|---|
| Kinematic Viscosity (KV) | ASTM D 445 |
| Viscosity Index (VI) | ASTM D 2270 |
| Pour Point | ASTM D 97 |
| Specific Gravity and Density | ASTM D 4052 (15.6/15.6° C.) |
| Flash Point | ASTM D 92 |
| $M_n$ | GC (if KV100 of 10 cSt or less) or GPC (if KV100 is more than 10 cSt) (see Experimental Methods) |
| Glass Transition Temperature ($T_g$) | ASTM 1356 |
| Branch Paraffin: N-paraffin ratio | $^{13}$C-NMR (see Experimental Methods) |
| Wt % mono-methyl species | $^{13}$C-NMR (see Experimental Methods) |
| % side chains with X number of carbons | $^{13}$C-NMR (see Experimental Methods) |
| Boiling/Distillation Range | ASTM D 1160 |
| Carbon Type Composition ($C_A$, $C_N$, $C_P$) | ASTM D 2140 (see Experimental Methods) |

TABLE B3-continued

| NFP Property Test Methods | |
|---|---|
| Saturates Content | ASTM D 2007 |
| Sulfur Content | ASTM D 2622 |
| Nitrogen Content | ASTM D 4629 |
| Bromine Number | ASTM D 1159 (or ASTM D 2710 if so directed by ASTM D 1159) |
| Aniline Point | ASTM D 611 |
| Color | ASTM D 1209 (APHA Color) |

DETAILED DESCRIPTION OF THE INVENTION

This invention relates to articles formed from plasticized thermoplastic polyolefin compositions comprising one or more thermoplastic polyolefins, one or more non-functionalized plasticizers, and one or more nucleating agents.

Composition

Polyolefin(s) are preferably present in the compositions of the present invention at from 40 to 99.9 wt % in one embodiment, and from 50 to 99 wt % in another embodiment, and from 60 to 98 wt % in yet another embodiment, and from 70 to 97 wt % in yet another embodiment, and from 80 to 97 wt % in yet another embodiment, and from 90 to 98 wt % in yet another embodiment, based upon the weight of the polyolefin(s) and the NFP, wherein a desirable range may be any combination of any upper wt % limit with any lower wt % limit described herein.

Polyolefin(s) are preferably present in the compositions of the present invention at from 40 to 99.9 wt % in one embodiment, and from 50 to 99 wt % in another embodiment, and from 60 to 98 wt % in yet another embodiment, and from 70 to 97 wt % in yet another embodiment, and from 80 to 97 wt % in yet another embodiment, and from 90 to 98 wt % in yet another embodiment, based upon the total weight of composition, wherein a desirable range may be any combination of any upper wt % limit with any lower wt % limit described herein.

NFP(s) are preferably present in the compositions of the present invention at from 60 to 0.1 wt % in one embodiment, and from 50 to 1 wt % in another embodiment, and from 40 to 2 wt % in yet another embodiment, and from 30 to 3 wt % in yet another embodiment, and from 20 to 4 wt % in yet another embodiment, and from 10 to 5 wt % in yet another embodiment, and at 5 wt % or less in yet another embodiment, and at 4 to 0.1 wt % in yet another embodiment, based upon the weight of the NFP(s) and polyolefin(s), wherein a desirable range may be any combination of any upper wt % limit with any lower wt % limit described herein.

NFP(s) are preferably present in the compositions of the present invention at from 60 to 0.1 wt % in one embodiment, and from 50 to 1 wt % in another embodiment, and from 40 to 2 wt % in yet another embodiment, and from 30 to 3 wt % in yet another embodiment, and from 20 to 4 wt % in yet another embodiment, and from 10 to 5 wt % in yet another embodiment, and at 5 wt % or less in yet another embodiment, and at 4 to 0.1 wt % in yet another embodiment, based upon the total weight of composition, wherein a desirable range may be any combination of any upper wt % limit with any lower wt % limit described herein.

In another embodiment, the plasticized polyolefin comprises polypropylene present at 40 to 99.99 wt %, alternately 50 to 99 wt %, alternately 60 to 99 wt %, alternately 70 to 98 wt %, alternately 80 to 97 wt %, alternately 90 to 96 wt %, and the NFP is present at 60 to 0.01 wt %, alternately 50 to 1 wt %, alternately 40 to 1 wt %, alternately 30 to 2 wt %, alternately 20 to 3 wt %, alternately 10 to 4 wt %, alternatively 5 to 0.1 wt %, based upon the weight of the polypropylene and the NFP, wherein a desirable range may be any combination of any upper wt % limit with any lower wt % limit described herein.

In another embodiment, the plasticized polyolefin comprises polypropylene present at 40 to 99.99 wt %, alternately 50 to 99 wt %, alternately 60 to 99 wt %, alternately 70 to 98 wt %, alternately 80 to 97 wt %, alternately 90 to 96 wt %, and the NFP is present at 60 to 0.01 wt %, alternately 50 to 1 wt %, alternately 40 to 1 wt %, alternately 30 to 2 wt %, alternately 20 to 3 wt %, alternately 10 to 4 wt %, alternatively 5 to 0.1 wt %, based upon the total weight of the composition, wherein a desirable range may be any combination of any upper wt % limit with any lower wt % limit described herein.

In another embodiment, the plasticized polyolefin comprises a polypropylene blend present at 40 to 99.99 wt %, alternately 50 to 99 wt %, alternately 60 to 99 wt %, alternately 70 to 98 wt %, alternately 80 to 97 wt %, alternately 90 to 96 wt %, and the NFP is present at 60 to 0.01 wt %, alternately 50 to 1 wt %, alternately 40 to 1 wt %, alternately 30 to 2 wt %, alternately 20 to 3 wt %, alternately 10 to 4 wt %, alternatively 5 to 0.1 wt %, based upon the total weight of the polypropylene blend and the NFP, wherein a desirable range may be any combination of any upper wt % limit with any lower wt % limit described herein.

In another embodiment, the plasticized polyolefin comprises polypropylene present at 20 to 95.99 wt %, alternately 40 to 93 wt %, alternately 55 to 90 wt %, based upon the total weight of the polypropylene blend and the NFP, wherein a desirable range may be any combination of any upper wt % limit with any lower wt % limit described herein.

In another embodiment, the plasticized polyolefin comprises EP rubber present at 4 to 50 wt %, alternately 6 to 40 wt %, alternately 8 to 30 wt %, based upon the total weight of the polypropylene blend and the NFP, wherein a desirable range may be any combination of any upper wt % limit with any lower wt % limit described herein.

In another embodiment, the plasticized polyolefin comprises polyethylene present at 50 to 99.99 wt %, alternately 60 to 99 wt %, alternately 70 to 98 wt %, alternately 80 to 97 wt %, alternately 90 to 96 wt %, and the NFP is present at 50 to 0.01 wt %, alternately 40 to 1 wt %, alternately 30 to 2 wt %, alternately 20 to 3 wt %, alternately 10 to 4 wt %, alternatively 5 to 0.1 wt %, based upon the weight of the polyethylene and the NFP, wherein a desirable range may be any combination of any upper wt % limit with any lower wt % limit described herein.

In another embodiment, the plasticized polyolefin comprises polyethylene present at 50 to 99.99 wt %, alternately 60 to 99 wt %, alternately 70 to 98 wt %, alternately 80 to 97 wt %, alternately 90 to 96 wt %, and the NFP is present at 50 to 0.01 wt %, alternately 40 to 1 wt %, alternately 30 to 2 wt %, alternately 20 to 3 wt %, alternately 10 to 4 wt %, alternatively 5 to 0.1 wt %, based upon the total weight of the composition, wherein a desirable range may be any combination of any upper wt % limit with any lower wt % limit described herein.

In another embodiment, the plasticized polyolefin comprises a polyethylene blend present at 40 to 99.99 wt %, alternately 50 to 99 wt %, alternately 60 to 99 wt %, alternately 70 to 98 wt %, alternately 80 to 97 wt %, alternately 90 to 96 wt %, and the NFP is present at 60 to 0.01 wt %, alternately 50 to 1 wt %, alternately 40 to 1 wt %, alternately 30 to 2 wt %, alternately 20 to 3 wt %, alternately 10 to 4 wt %, alternatively 5 to 0.1 wt %, based upon the total weight of the polyethylene blend and the NFP, wherein a desirable range may be any combination of any upper wt % limit with any lower wt % limit described herein.

In another embodiment, the plasticized polyolefin comprises polybutene present at 50 to 99.99 wt %, alternately 60 to 99 wt %, alternately 70 to 98 wt %, alternately 80 to 97 wt %, alternately 90 to 96 wt %, and the NFP is present at 50 to 0.01 wt %, alternately 40 to 1 wt %, alternately 30 to 2 wt %, alternately 20 to 3 wt %, alternately 10 to 4 wt %, alternatively 5 to 0.1 wt %, based upon the weight of the polybutene and the NFP, wherein a desirable range may be any combination of any upper wt % limit with any lower wt % limit described herein.

In another embodiment, the plasticized polyolefin comprises polybutene present at 50 to 99.99 wt %, alternately 60 to 99 wt %, alternately 70 to 98 wt %, alternately 80 to 97 wt %, alternately 90 to 96 wt %, and the NFP is present at 50 to 0.01 wt %, alternately 40 to 1 wt %, alternately 30 to 2 wt %, alternately 20 to 3 wt %, alternately 10 to 4 wt %, alternatively 5 to 0.1 wt %, based upon the total weight of the composition, wherein a desirable range may be any combination of any upper wt % limit with any lower wt % limit described herein.

In another embodiment, the plasticized polyolefin comprises a polybutene blend present at 40 to 99.99 wt %, alternately 50 to 99 wt %, alternately 60 to 99 wt %, alternately 70 to 98 wt %, alternately 80 to 97 wt %, alternately 90 to 96 wt %, and the NFP is present at 60 to 0.01 wt %, alternately 50 to 1 wt %, alternately 40 to 1 wt %, alternately 30 to 2 wt %, alternately 20 to 3 wt %, alternately 10 to 4 wt %, alternatively 5 to 0.1 wt %, based upon the total weight of the polybutene blend and the NFP, wherein a desirable range may be any combination of any upper wt % limit with any lower wt % limit described herein.

In another embodiment, the polyolefin comprises polypropylene, polyethylene, and or polybutene, and NFP is present at 0.01 to 50 wt %, more preferably 0.05 to 45 wt %, more preferably 0.5 to 40 wt %, more preferably 1 to 35 wt %, more preferably 2 to 30 wt %, more preferably 3 to 25 wt %, more preferably 4 to 20 wt %, more preferably 5 to 15 wt %, more preferably 0.1 to 5 wt %, based upon the weight of the composition. In yet another embodiment, the NFP is present at 1 to 15 wt %, preferably 1 to 10 wt %, based upon the weight of the polypropylene, polyethylene, and or polybutene and the NFP. In another embodiment, the NFP is present at 1 to 15 wt %, preferably 1 to 10 wt %, based on the total weight of the composition.

In another embodiment, the NFP is present at more than 3 wt %, based upon the weight of the polyolefin and the NFP. In another embodiment, the NFP is present at more than 3 wt % based on the total weight of the composition.

In another embodiment, the compositions comprise less than 50 wt % (preferably less than 45 wt %, preferably less than 40 wt %, preferably less than 35 wt %, preferably less than 30 wt %, preferably less than 25 wt %, preferably less than 20 wt %, preferably less than 15 wt %, preferably less than 10 wt %, more preferably less than 5 wt %, more preferably less than 3 wt %, more preferably less than 1 wt %) of EP Rubber, based upon the total weight of the composition.

In another embodiment, the compositions comprise less than 50 wt % (preferably less than 45 wt %, preferably less than 40 wt %, preferably less than 35 wt %, preferably less than 30 wt %, preferably less than 25 wt %, preferably less than 20 wt %, preferably less than 15 wt %, preferably less than 10 wt %, preferably less than 5 wt %, preferably less than 3 wt %, preferably less than 2 wt %, preferably less than 1 wt %, more preferably less than 0.5 wt %, more preferably less than 0.1 wt %) of an elastomer, based upon the total weight of the composition. "Elastomer" in this embodiment includes olefin-based and diene-based elastomers and thermoplastic elastomers, such as dynamically vulcanized alloys and styrenic block copolymers.

In another embodiment, the ethylene, propylene, and or butene polymers in the present invention comprise 0% diene. In another embodiment, the total diene content of all polyolefins present in the composition is 0%. In another embodiment, any polyolefin present in the composition contains less than 30 wt % (preferably less than 20 wt %, preferably less than 10 wt %, preferably less than 5 wt %, preferably less than 2.5 wt %, preferably less than 1 wt %) diene, based upon the weight of the polyolefin.

In another embodiment, the compositions may further comprise a copolymer or co-oligomer of ethylene and one or more alpha-olefin(s), such as those disclosed in U.S. Pat. Nos. 6,639,020 and 6,916,882.

In a another embodiment, the compositions comprise less than 40 wt % (preferably less than 30 wt %, preferably less than 20 wt %, preferably less than 10 wt %, preferably less than 5 wt %, preferably less than 1 wt %, preferably 0%), based upon the weight of the composition, of ethylene/α-olefin copolymer(s), where the α-olefin(s) are chosen from propylene, 1-butene, 1-hexene, and 1-octene, and the ethylene/α-olefin copolymer is a liquid.

In another embodiment, the compositions comprise less than 20 wt % (preferably less than 10 wt %, preferably less than 1 wt %), based upon the weight of the composition, of a liquid homopolymer or copolymer of isoprene and or butadiene having a kinematic viscosity at 40° C. of 10,000 cSt or less. In another embodiment, the compositions comprise less than 20 wt % (preferably less than 10 wt %, preferably less than 1 wt %), based upon the weight of the composition, of a liquid homopolymer or copolymer of isoprene and or butadiene having a kinematic viscosity at 40° C. between 2,000 cSt and 20 cSt.

In another embodiment, conventional plasticizers such as is commonly used for poly(vinyl chloride) are substantially absent. In particular, plasticizers such as phthalates, adipates, trimellitate esters, polyesters, and other functionalized plasticizers as disclosed in, for example, U.S. Pat. Nos. 3,318,835; 4,409,345; WO 02/31044; and PLASTICS ADDITIVES 499-504 (Geoffrey Pritchard, ed., Chapman & Hall 1998) are substantially absent. By "substantially absent", it is meant that these compounds are not added deliberately to the compositions and if present at all, are present at less than 0.5 wt %, based upon the weight of the composition.

In another embodiment, "naphthenic" and "aromatic" mineral oils and Group I and II basestocks are substantially absent; i.e., present at less than 0.5 wt % of the total composition. In another embodiment, if such mineral oils and/or basestocks are present in the composition, the aggregate of such mineral oils and/or basestocks is at most 20 wt % (preferably at most 15 wt %, more preferably at most 10 wt %, most preferably at most 5 wt %) of the amount of NFP in the composition, based upon the weight of the NFP.

In another embodiment, an oligomer of $C_4$ olefin(s) (where, for the purposes of this invention, "$C_4$ olefin(s)" is defined to include 1-butene, 2-butene, isobutylene, butadiene, and mixtures thereof) may be present in the composition. In a preferred embodiment, the composition comprises less than 50 wt % (preferably less than 40%, preferably less than 30 wt %, preferably less than 20 wt %, preferably less than 10 wt %, preferably less than 5 wt %, preferably less than 1 wt %, preferably 0 wt %) polymer or oligomer of $C_4$ olefin(s), based upon the weight of the composition.

In a preferred embodiment, the NFP contains less than 50 wt % (preferably less than 40 wt %, preferably less than 30 wt %, preferably less than 20 wt %, preferably less than 10 wt %, preferably 5 wt %, preferably less than 2%, preferably less than 1 wt %, preferably 0 wt %) of $C_4$ olefin(s) including polyisobutylene, based upon the weight of the NFP.

In one embodiment of the invention, the polyolefin suitable for the composition excludes physical blends of polypropylene with other polyolefins, and in particular, excludes physical blends of polypropylene with low molecular weight (500 to 10,000 g/mol) polyethylene or polyethylene copolymers, meaning that, low molecular weight polyethylene or polyethylene copolymers are not purposefully added in any amount to the polyolefin (e.g., polypropylene) compositions of the invention, such as is the case in, for example, WO 01/18109 A1.

Non-Functionalized Plasticizer

The polyolefin compositions of the present invention include at least one non-functionalized plasticizer ("NFP"). The classes of materials described herein that are useful as non-functionalized plasticizers can be utilized alone or admixed with other NFP's described herein in order to obtain desired properties. Any NFP useful in the present invention may also be described by any number of, or any combination of, parameters described herein, and it the classes of materials described herein that are useful as NFPs can be utilized alone or admixed with other NFPs described herein in order to obtain desired properties.

A NFP is a hydrocarbon liquid, that is a liquid compound comprising carbon and hydrogen, which does not include to an appreciable extent functional groups selected from hydroxide, aryls and substituted aryls, halogens, alkoxys, carboxylates, esters, carbon unsaturation, acrylates, oxygen, nitrogen, and carboxyl. By "appreciable extent", it is meant that these groups and compounds comprising these groups are not deliberately added to the NFP, and if present at all, are present at less than 5 wt % by weight of the NFP in one embodiment, more preferably less than 4 wt %, more preferably less than 3 wt %, more preferably less than 2 wt %, more preferably less than 1 wt %, more preferably less than 0.7 wt %, more preferably less than 0.5 wt %, more preferably less than 0.3 wt %, more preferably less than 0.1 wt %, more preferably less than 0.05 wt %, more preferably less than 0.01 wt %, more preferably less than 0.001 wt %, based upon the weight of the NFP.

In one embodiment, aromatic moieties (including any compound whose molecules have the ring structure characteristic of benzene, naphthalene, phenanthrene, anthracene, etc.) are substantially absent from the NFP. By "substantially absent", it is meant that these compounds are not added deliberately to the compositions and if present at all, are present at less than 0.5 wt %, preferably less than 0.1 wt %.

In another embodiment, naphthenic moieties (including any compound whose molecules have a saturated ring structure such as would be produced by hydrogenating benzene, naphthalene, phenanthrene, anthracene, etc.) are substantially absent from the NFP. By "substantially absent", it is meant that these compounds are not added deliberately to the compositions and if present at all, are present at less than 0.5 wt %, preferably less than 0.1 wt %.

In another embodiment, the NFP is a hydrocarbon that does not contain olefinic unsaturation to an appreciable extent. By "appreciable extent of olefinic unsaturation" it is meant that the carbons involved in olefinic bonds account for less than 10% (preferably less than 8%, more preferably less than 6%, more preferably less than 4%, more preferably less than 2%, more preferably less than 1%, more preferably less than 0.7%, more preferably less than 0.5%, more preferably less than 0.3%, more preferably less than 0.1%, more preferably less than 0.05%, more preferably less than 0.01%, more preferably less than 0.001%) of the total number of carbons. In some embodiments, the percent of carbons of the NFP involved in olefinic bonds is between 0.001 and 10% of the total number of carbon atoms in the NFP, preferably between 0.01 and 5%, preferably between 0.1 and 2%, more preferably less than 1%.

Particularly preferred NFPs include isoparaffins, PAOs, Group III basestocks or mineral oils, high purity hydrocarbon fluids derived from a so-called Gas-To-Liquids processes, and mineral oils with a viscosity index greater than 100, pour point less than –20° C., specific gravity less than 0.86, and flash point greater than 200° C.

In another embodiment, the NFP comprises $C_6$ to $C_{200}$ paraffins, and $C_8$ to $C_{100}$ paraffins in another embodiment. In another embodiment, the NFP consists essentially of $C_6$ to $C_{200}$ paraffins, or essentially of $C_8$ to $C_{100}$ paraffins in another embodiment. In yet another embodiment, the NFP comprises $C_{20}$ to $C_{1500}$ paraffins, preferably $C_{25}$ to $C_{500}$ paraffins, preferably $C_{25}$ to $C_{500}$ paraffins, preferably $C_{30}$ to $C_{500}$ paraffins, preferably $C_{40}$ to $C_{500}$ paraffins, preferably $C_{40}$ to $C_{250}$ paraffins, preferably $C_{30}$ to $C_{150}$ paraffins, preferably $C_{20}$ to $C_{100}$ paraffins. In a preferred embodiment, the NFP comprises oligomers of $C_5$ to $C_{24}$ olefins.

Isoparaffins

In one embodiment of the present invention, the NFP is an isoparaffin-rich hydrocarbon liquid with a pour point of –50° C. or less (preferably –60° C. or less) and a specific gravity of 0.84 or less (preferably 0.83 or less). By isoparaffin-rich is meant that the NFP comprises at least 50 wt % (preferably at least 60 wt %, preferably at least 70 wt %, preferably at least 80 wt %, preferably at least 90 wt %, preferably 100 wt %) of $C_6$ to $C_{150}$ (preferably $C_6$ to $C_{100}$, preferably $C_6$ to $C_{25}$, preferably $C_8$ to $C_{20}$) isoparaffins. Preferably the paraffin chains possess $C_1$ to $C_{10}$ alkyl branching along at least a portion of each paraffin chain. More preferably, the isoparaffins are saturated aliphatic hydrocarbons whose molecules have at least one carbon atom bonded to at least three other carbon atoms or at least one side chain (i.e., a molecule having one or more tertiary or quaternary carbon atoms), wherein the number-average molecular weight is in the range of 100 to 1000 (preferably 120 to 500, preferably 150 to 300) g/mol.

In another embodiment, the isoparaffin-rich NFP has a kinematic viscosity at 25° C. of 30 cSt or less (preferably 25 cSt or less, preferably 20 cSt or less, preferably 15 cSt or less) and a glass transition temperature ($T_g$) that cannot be determined by ASTM E 1356 or if it can be determined then the $T_g$ according to ASTM E 1356 is preferably less than 0° C., more preferably less than –10° C., more preferably less than –20° C., more preferably less than –30° C. Preferably the number-average molecular weight of the isoparaffin-rich NFP is in the range of 100 to 300 g/mol.

In another embodiment, the isoparaffin-rich NFP is a mixture of branched and normal paraffins having from 6 to 50 carbon atoms, and from 10 to 24 carbon atoms in another embodiment, in the molecule. The isoparaffin composition has a ratio of branch paraffin to n-paraffin ratio (branch paraffin:n-paraffin) ranging from 0.5:1 to 9:1 in one embodiment, and from 1:1 to 4:1 in another embodiment. The isoparaffins of the mixture in this embodiment contain greater than 50 wt % (by total weight of the isoparaffin composition) mono-methyl species, for example, 2-methyl, 3-methyl, 4-methyl, 5-methyl or the like, with minimum formation of branches with substituent groups of carbon number greater than 1, such as, for example, ethyl, propyl, butyl or the like, based on the total weight of isoparaffins in the mixture. In one embodiment, the isoparaffins of the mixture contain greater than 70 wt % of the mono-methyl species, based on the total weight of the isoparaffins in the mixture. The isoparaffinic mixture boils within a range of from 100° C. to 350° C. in one embodiment, and within a range of from 110° C. to 320° C. in another embodiment. In preparing the different grades, the paraffinic mixture is generally fractionated into cuts having narrow boiling ranges, for example, 35° C. boiling ranges. These branch paraffin/n-paraffin blends are described in, for example, U.S. Pat. No. 5,906,727.

Suitable isoparaffin-rich hydrocarbon liquids are described in, for example, U.S. Pat. Nos. 6,197,285, 3,818,105 and 3,439,088, and are commercially available under the tradename ISOPAR™ (ExxonMobil Chemical), some of which are summarized in Table B. Other suitable isoparaffin-rich hydrocarbon liquids are commercial available under the trade names SHELLSOL™ (Royal Dutch/Shell), SOLTROL™ (Chevron Phillips) and SASOL™ (Sasol Limited). The percentage of carbons in chain-type paraffinic structures ($C_P$) in such liquids is close to 100% (95% or more).

TABLE C

ISOPAR ™ Series Isoparaffins

| | KV @ 25° C. (cSt) | pour point (° C.) | specific gravity | flash point (° C.) | distillation range (° C.) |
|---|---|---|---|---|---|
| ISOPAR G | 1.5 | −57 | 0.75 | 106 | 161-176 |
| ISOPAR H | 1.8 | −63 | 0.76 | 127 | 178-188 |
| ISOPAR K | 1.9 | −60 | 0.76 | 131 | 179-196 |
| ISOPAR L | 2.0 | −57 | 0.77 | 144 | 188-207 |
| ISOPAR M | 3.8 | −57 | 0.79 | 198 | 223-254 |
| ISOPAR V | 14.8 | −63 | 0.82 | 266 | 272-311 |

In another embodiment the isoparaffin-rich NFP has one or more of the following properties:

1. a distillation range (as determined by ASTM D 86) having a difference between the upper temperature and the lower temperature of 40° C. or less, preferably 30° C. or less, preferably 20° C. or less, preferably 10° C. or less, preferably between 6 and 40° C.; and or
2. a glass transition temperature ($T_g$) determined by ASTM E1356 of less than 0° C., preferably less than −10° C., more preferably less than −20° C., more preferably less than −30° C., more preferably less than −50° C., or most preferably a Tg that can not be determined by ASTM E1356; and or
3. a pour point (as determined by ASTM D 97) of −40° C. or less, preferably −50° C. or less, preferably −60° C. or less; and or
4. a specific gravity (as determined by ASTM D 4052, 15.6/15.6° C.) of less than 0.85, preferably less than 0.84, preferably less than 0.83, preferably from 0.65 to 0.85, preferably from 0.70 to 0.84, preferably from 0.75 to 0.83, preferably from 0.800 to 0.840; and or
5. a final boiling point (as determined by ASTM D 1160) of from 115 to 500° C., preferably from 200 to 450° C., preferably from 250 to 400° C.; and or
6. a number average molecular weight (Mn) between 2,000 and 100 g/mol, preferably between 1500 and 150, more preferably between 1000 and 200; and or
7. a flash point as measured by ASTM D 56 of 0 to 150° C., and or
8. a density (ASTM D4052, 15.6° C.) of from 0.70 to 0.83 g/cm$^3$; and or
9. a kinematic viscosity (ASTM D445) of from 0.5 to 20 cSt at 25° C.

Polyalphaolefins

In another embodiment of the present invention, the NFP comprises a polyalphaolefin (PAO) liquid with a pour point (as measured by ASTM D 97) of −10° C. or less and a kinematic viscosity at 100° C. (measured by ASTM D 445) of 3 cSt or more. PAO liquids are described in, for example, U.S. Pat. Nos. 3,149,178; 4,827,064; 4,827,073; 5,171,908; and 5,783,531 and in SYNTHETIC LUBRICANTS AND HIGH-PERFORMANCE FUNCTIONAL FLUIDS (Leslie R. Rudnick & Ronald L. Shubkin, ed. Marcel Dekker, Inc. 1999), p. 3-52.

PAO liquids may be conveniently prepared by the oligomerization of an α-olefin in the presence of a polymerization catalyst, such as a Friedel-Crafts catalyst (including, for example, $AlCl_3$, $BF_3$, and complexes of $BF_3$ with water, alcohols, carboxylic acids, or esters), a coordination complex catalyst (including, for example, the ethylaluminum sesquichloride+$TiCl_4$ system), or a homogeneous or heterogeneous (supported) catalyst more commonly used to make polyethylene and/or polypropylene (including, for example, Ziegler-Natta catalysts, metallocene or other single-site catalysts, and chromium catalysts).

In one embodiment, the PAO comprises $C_{20}$ to $C_{1500}$ (preferably $C_{30}$ to $C_{800}$, more preferably $C_{35}$ to $C_{400}$, most preferably $C_{40}$ to $C_{250}$) oligomers of α-olefins. These oligomers are dimers, trimers, tetramers, pentamers, etc. of $C_3$ to $C_{24}$ (preferably $C_5$ to $C_{18}$, more preferably $C_6$ to $C_{14}$, more preferably $C_8$ to $C_{12}$, even more preferably $C_{10}$) branched or linear α-olefins. In another embodiment, the PAO comprises $C_3$ to $C_{24}$ (preferably $C_5$ to $C_{18}$, more preferably $C_6$ to $C_{14}$, most preferably $C_8$ to $C_{12}$) linear α-olefins (LAOs). Suitable olefins include propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and blends thereof. Oligomers of 1-olefinsLAOs with only even carbon numbers between 6 and 18 (inclusive) are preferred.

In one embodiment, a single LAO is used to prepare the oligomers. In this case, a preferred embodiment involves the oligomerization of 1-decene, and the PAO is a mixture of oligomers (including, for example, dimers, trimers, tetramers, pentamers, and higher) of 1-decene. In another embodiment, the PAO comprises oligomers of two or more $C_3$ to $C_{16}$ LAOs, to make 'bipolymer' or 'terpolymer' or higher-order copolymer combinations. In this case, a preferred embodiment involves the oligomerization of a mixture of 1-octene, 1-decene, and 1-dodecene, and the PAO is a mixture of oligomers (for example, dimers, trimers, tetramers, pentamers, and higher) of 1-octene/1-decene/1-dodecene 'terpolymer'.

In another embodiment, the PAO comprises oligomers of a single alpha-olefin species having a carbon number of 5 to 24 (preferably 6 to 18, more preferably 8 to 12, most preferably 10). In another embodiment, the NFP comprises oligomers of mixed alpha-olefins (i.e., involving two or more alpha-olefin species), each alpha-olefin having a carbon number of 3 to 24 (preferably 5 to 24, more preferably 6 to 18, most preferably 8 to 12), provided that alpha-olefins having a carbon number or 3 or 4 are present at less than 10 weight %. In a particularly preferred embodiment, the PAO comprises oligomers of mixed alpha-olefins (i.e., involving two or more alpha-olefin species) where the weighted average carbon number for the alpha-olefin mixture is 6 to 14 (preferably 8 to 12, preferably 9 to 11).

In another embodiment, the PAO comprises oligomers of one or more α-olefin with repeat unit formulas of

—[CHR—CH$_2$]

where R is a C$_3$ to C$_{18}$ saturated hydrocarbon branch. In a preferred embodiment, R is constant for all oligomers. In another embodiment, there is a range of R substituents covering carbon numbers from 3 to 18. Preferably, R is linear, i.e., R is (CH$_2$)$_n$CH$_3$, where n is 3 to 17, preferably 4 to 11, and preferably 5 to 9. Optionally, R may contain one methyl or ethyl branch, i.e., R is (CH$_2$)$_m$[CH(CH$_3$)](CH$_2$)$_z$CH$_3$ or R is (CH$_2$)$_x$[CH(CH$_2$CH$_3$)](CH$_2$)$_y$CH$_3$, where (m+z) is 1 to 15, preferably 1 to 9, preferably 3 to 7, and (x+y) is 1 to 14, preferably 1 to 8, preferably 2 to 6. Preferably m>z; more preferably m is 0 to 15, more preferably 2 to 15, more preferably 3 to 12, more preferably 4 to 9; and n is 0 to 10, preferably 1 to 8, preferably 1 to 6, preferably 1 to 4. Preferably x>y; more preferably x is 0 to 14, more preferably 1 to 14, more preferably 2 to 11, more preferably 3 to 8; and y is 0 to 10, preferably 1 to 8, preferably 1 to 6, preferably 1 to 4. Preferably, the repeat units are arranged in a head-to-tail fashion with minimal heat-to-head connections.

The PAO may be atactic, isotactic, or syndiotactic. In one embodiment, the PAO has essentially the same population of meso and racemic dyads, on average, making it atactic. In another embodiment, the PAO has more than 50% (preferably more than 60%, preferably more than 70%, preferably more than 80%, preferably more than 90%) meso dyads (i.e., [m]) as measured by $^{13}$C-NMR. In another embodiment, the PAO has more than 50% (preferably more than 60%, preferably more than 70%, preferably more than 80%, preferably more than 90%) racemic dyads (i.e., [r]) as measured by $^{13}$C-NMR. In one embodiment, [m]/[r] determined by $^{13}$C-NMR is between 0.9 and 1.1 in one embodiment, [m]/[r] is greater than 1 in another embodiment, and [m]/[r] is less than 1 in yet another embodiment.

The PAO liquid may be comprised of one or more distinct PAO components. In one embodiment, the NFP is a blend of one or more PAOs with different compositions (e.g., different α-olefin(s) were used to make the oligomers) and/or different physical properties (e.g., kinematic viscosity, pour point, viscosity index, and/or glass transition temperature).

In one embodiment of the present invention, the PAO or blend of PAOs has a number average molecular weight of from 100 to 20,000 g/mol (preferably 300 to 15,000 g/mol, preferably 400 to 10,000 g/mol, preferably 500 to 5,000 g/mol, preferably 600 to 3,000 g/mol, preferably 600 to 1,500 g/mol).

In a preferred embodiment, the PAO or blend of PAOs has a kinematic viscosity at 100° C. of 3 cSt or more (preferably 5 cSt or more, preferably 6 cSt or more, preferably 8 cSt or more, preferably 10 cSt or more, preferably 20 cSt or more, preferably 30 cSt or more, preferably 40 cSt or more, preferably 100 or more, preferably 150 cSt or more). In another embodiment, the PAO or blend of PAOs has a kinematic viscosity at 100° C. of 300 cSt or less (preferably 100 cSt or less). In another embodiment, the PAO has a kinematic viscosity at 100° C. of 3 to 3,000 cSt (preferably 4 to 1,000 cSt, preferably 6 to 300 cSt, preferably 8 to 150 cSt, preferably 8 to 100 cSt, preferably 8 to 40 cSt). In another embodiment, the PAO or blend of PAOs has a kinematic viscosity at 100° C. of 10 to 1000 cSt (preferably 10 to 300 cSt, preferably 10 to 100 cSt). In yet another embodiment, the PAO or blend of PAOs has a kinematic viscosity at 100° C. of about 4 to 8 cSt.

In another preferred embodiment, the PAO or blend of PAOs has a Viscosity Index of 120 or more (preferably 130 or more, preferably 140 or more, preferably 150 or more, preferably 170 or more, preferably 190 or more, preferably 200 or more, preferably 250 or more, preferably 300 or more). In another embodiment, the PAO or blend of PAOs has a viscosity Index of 120 to 350 (preferably 130 to 250).

In yet another preferred embodiment, the PAO or blend of PAOs has a pour point of −10° C. or less (preferably −20° C. or less, preferably −25° C. or less, preferably −30° C. or less, preferably −35° C. or less, preferably −40° C. or less, preferably −50° C. or less). In another embodiment, the PAO or blend of PAOs has a pour point of −15 to −70° C. (preferably −25 to −60° C.).

In yet another preferred embodiment, the PAO or blend of PAOs has a glass transition temperature (T$_g$) of −40° C. or less (preferably −50° C. or less, preferably −60° C. or less, preferably −70° C. or less, preferably −80° C. or less). In another embodiment, the PAO or blend of PAOs has a T$_g$ of −50 to −120° C. (preferably −60 to −100° C., preferably −70 to −90° C.).

In yet another preferred embodiment, the PAO or blend of PAOs has a flash point of 200° C. or more (preferably 210° C. or more, preferably 220° C. or more, preferably 230° C. or more), preferably between 240° C. and 290° C.

In yet another preferred embodiment, the PAO or blend of PAOs has a specific gravity (15.6/15.6° C.) of 0.86 or less (preferably 0.855 or less, preferably 0.85 or less, preferably 0.84 or less).

Particularly preferred PAOs and blends of PAOs are those having A) a flash point of 200° C. or more (preferably 210° C. or more, preferably 220° C. or more, preferably 230° C. or more); and B) a pour point less than −20° C. (preferably less than −25° C., preferably less than −30° C., preferably less than −35°, preferably less than −40° C.) and/or a kinematic viscosity at 100° C. of 10 cSt or more (preferably 35 cSt or more, preferably 40 cSt or more, preferably 50 cSt or more).

Further preferred PAOs or blends of PAOs have a kinematic viscosity at 100° C. of at least 3 cSt (preferably at least 6 cSt, more preferably at least 8 cSt, most preferably at least 10 cSt, as measured by ASTM D445); a viscosity index of at least 120 (preferably at least 130, more preferably at least 140, most preferably at least 150, as determined by ASTM D2270); a pour point of −10° C. or less (preferably −20° C. or less, more preferably −30° C. or less, most preferably −40° C. or less, as determined by ASTM D97); and a specific gravity (15.6/15.6° C.) of 0.86 or less (preferably 0.855 or less, more preferably 0.85 or less, most preferably 0.84 or less, as determined by ASTM D 4052).

Desirable PAOs are commercially available as SpectraSyn™ and SpectraSyn Ultra™ from ExxonMobil Chemical in Houston, Tex. (previously sold under the SHF and SuperSyn™ tradenames by ExxonMobil Chemical Company), some of which are summarized in Table D. Other useful PAOs include those sold under the tradenames Synfluid™ available from ChevronPhillips Chemical Company (Pasadena, Tex.), Durasyn™ available from Innovene (Chicago, Ill.), Nexbase™ available from Neste Oil (Keilaniemi, Finland), and Synton™ available from Chemtura Corporation (Middlebury, Conn.). For PAOs, the percentage of carbons in chain-type paraffinic structures ($C_P$) is close to 100% (typically greater than 98% or even 99%).

from $C_4$ olefin(s) are summarized in Table E. In general, grades with a flash point of 200° C. or more also have a pour point greater than −10° C. and/or a VI less than 120.

TABLE E

Commercial Examples of Oligomers of $C_4$ olefin(s)

| Grade | KV @ 100° C., cSt | VI | Pour Point, ° C. | Specific gravity | Flash Point, ° C. |
|---|---|---|---|---|---|
| TPC 137 (PIB) | 6 | 132 | −51 | 0.843 | 120 |
| TPC 1105 (PIB) | 220 | 145 | −6 | 0.893 | 200 |
| TPC 1160 (PIB) | 660 | 190 | +3 | 0.903 | 230 |
| Innovene Indopol H-25 | 52 | 87 | −23 | 0.869 | ~150 |
| Innovene Indopol H-50 | 108 | 90 | −13 | 0.884 | ~190 |
| Innovene Indopol H-100 | 218 | 121 | −7 | 0.893 | ~210 |
| Infineum C9945 | 11 | 74* | −34 | 0.854 | 170 |
| Infineum C9907 | 78 | 103* | −15 | 0.878 | 204 |
| Infineum C9995 | 230 | 131* | −7 | 0.888 | 212 |
| Infineum C9913 | 630 | 174* | +10 | 0.888 | 240 |

*Estimated based on the kinematic viscosity at 100° C. and 38° C.

TABLE D

SpectraSyn ™ Series Polyalphaolefins

| | KV @ 100° C., cSt | KV @ 40° C., cSt | VI | Pour Point, ° C. | Specific gravity | Flash Point, ° C. | APHA Color |
|---|---|---|---|---|---|---|---|
| SpectraSyn 4 | 4 | 19 | 126 | −66 | 0.820 | 220 | 10 |
| SpectraSyn Plus 4 | 4 | 17 | 122 | −60 | 0.820 | 228 | 10 |
| SpectraSyn 6 | 6 | 31 | 138 | −57 | 0.827 | 246 | 10 |
| SpectraSyn Plus 6 | 6 | 30 | 140 | −54 | 0.827 | 246 | 10 |
| SpectraSyn 8 | 8 | 48 | 139 | −48 | 0.833 | 260 | 10 |
| SpectraSyn 10 | 10 | 66 | 137 | −48 | 0.835 | 266 | 10 |
| SpectraSyn 40 | 39 | 396 | 147 | −36 | 0.850 | 281 | 10 |
| SpectraSyn 100 | 100 | 1240 | 170 | −30 | 0.853 | 283 | 60 |
| SpectraSyn Ultra 150 | 150 | 1,500 | 218 | −33 | 0.850 | >265 | 10 |
| SpectraSyn Ultra 300 | 300 | 3,100 | 241 | −27 | 0.852 | >265 | 20 |
| SpectraSyn Ultra 1000 | 1,000 | 10,000 | 307 | −18 | 0.855 | >265 | 30 |

In another embodiment, the PAO comprises oligomers of $C_4$ olefins (including n-butene, 2-butene, isobutylene, and butadiene, and mixtures thereof) with a kinematic viscosity at 100° C. of 5 to 4000 cSt and a pour point of 10 to −60° C. Such a material is referred to as a "polybutenes" liquid when the oligomers comprise isobutylene and/or 1-butene and/or 2-butene. It is commonly used as an additive for polyolefins; e.g. to introduce tack or as a processing aid. The ratio of $C_4$ olefin isomers can vary by manufacturer and by grade, and the material may or may not be hydrogenated after synthesis. In some cases, the polybutenes liquid is a polymer of a $C_4$ raffinate stream. In other cases, it consists essentially of polyisobutylene or poly(n-butene) oligomers. Typically, the polybutenes liquid has a number-average molecular weight of less than 15,000 g/mol, and commonly less than 5,000 g/mol or even less than 1,000 g/mol. They are described in, for example, SYNTHETIC LUBRICANTS AND HIGH-PERFORMANCE FUNCTIONAL FLUIDS (Leslie R. Rudnick & Ronald L. Shubkin, ed., Marcel Dekker 1999), p. 357-392.

Desirable polybutenes liquids are commercially available from a variety of sources including Innovene (Indopol grades) and Infineum (C-Series grades). When the $C_4$ olefin is exclusively isobutylene, the material is referred to as "polyisobutylene" or PIB. Commercial sources of PIB include Texas Petrochemical (TPC Enhanced PIB grades). When the $C_4$ olefin is exclusively 1-butene, the material is referred to as "poly-n-butene" or PNB. Properties of some liquids made This invention also relates to plasticized polyolefin compositions comprising one or more polyolefins, preferably polypropylene, and one or more non-functionalized plasticizers where the non-functionalized plasticizer comprises a polyalphaolefin comprising oligomers of $C_5$ to $C_{18}$ olefins (preferably $C_6$ to $C_{14}$, more preferably $C_8$ to $C_{12}$, more preferably $C_{10}$); having a kinematic viscosity of 5 cSt or more at 100° C. (preferably 8 cSt or more, preferably 10 cSt or more at 100° C.); a viscosity index of 120 or more (preferably 130 or more); and a pour point of −10° C. or less (preferably −20° C. or less, preferably −30° C. or less).

This invention also relates to plasticized polypropylene compositions comprising polypropylene and one or more non-functionalized plasticizers where the non-functionalized plasticizer comprises oligomers of linear olefins having 5 to 18 carbon atoms (preferably 6 to 14 carbon atoms, more preferably 8 to 12 carbon atoms, more preferably 10 carbon atoms); a kinematic viscosity at 100° C. of 5 to 300 cSt (preferably 8 to 150 cSt, preferably 10 to 100 cSt); a viscosity index of 120 or more (more preferably 130 or more, more preferably 140 or more); and a pour point of −20° C. or less (more preferably −30° C. or less, more preferably −40° C. or less).

This invention also relates to plasticized polypropylene compositions comprising polypropylene homopolymer and a non-functionalized plasticizer, where the non-functionalized plasticizer comprises oligomers of $C_5$ to $C_{18}$ olefins having a viscosity index of 120 or more and a kinematic viscosity at 40° C. of 4 to 45 cSt, provided that the plasticized composition does not comprise 15 to 28 wt % of a linear low density polyethylene (LLDPE). This invention also relates to plasticized polypropylene compositions comprising polypropylene homopolymer and PAOs having a kinematic viscosity at 40° C. of 4 to 45 cSt, provided that when the plasticized composition comprises between 4 and 10 wt % of polyalphaolefin that is a hydrogenated, highly branched dimer of an alpha olefin having 8-12 carbon atoms, the composition does not also comprise between 18 and 25 wt % of a linear low density polyethylene having a density of 0.912 to 0.935 g/cc.

This invention also relates to plasticized polyolefin compositions comprising a chlorine-free polyolefin and less than 9 wt % of a non-functionalized plasticizer, where the non-functionalized plasticizer consists of oligomers of $C_5$ to $C_{12}$ alpha-olefins having a viscosity index of 120 or more and a kinematic viscosity at 100° C. of less than 10 cSt, provided that the chlorine-free polyolefin does not comprise polypropylene. This invention also relates to plasticized polypropylene compositions comprising a polypropylene blend and less than 9 wt % of a non-functionalized plasticizer, where the non-functionalized plasticizer consists of oligomers of $C_5$ to $C_{12}$ alpha-olefins having a kinematic viscosity at 100° C. of less than 10 cSt, provided that the plasticized composition does not contain a polypropylene impact copolymer comprised of a polypropylene plastic matrix and an ethylene/alpha-olefin copolymer with a melt flow rate (ISO 1183, 230° C./2.16 kg) of less than 1 dg/min and a flexural modulus (ISO 178) of less than 380 MPa. This invention also relates to plasticized polypropylene compositions comprising polypropylene and less than 9 wt % of a non-functionalized plasticizer, where the non-functionalized plasticizer consists of oligomers of $C_5$ to $C_{12}$ alpha-olefins having a kinematic viscosity at 100° C. of less than 10 cSt, provided that the plasticized composition does not contain a polypropylene random copolymer with a melt flow rate (ISO 1133, 230° C./2.16 kg) of less than 2.5 dg/min and a melting temperature (DSC) of greater than 135° C.

In a particularly preferred embodiment the PAO has a kinematic viscosity at 100° C. of 10 cSt or more when the polypropylene comprises Borealis RB 501 F, or the polypropylene blend comprises Basell Hifax CA12A, or Basell Adflex Q 100F, as these polymers are described in WO 98/44041.

In another particularly preferred embodiment, the PAO has a kinematic viscosity at 100° C. of 10 cSt or more when the polypropylene composition comprises 5 to 60 wt % PAO and 20 to 95 wt % of one or more polyolefin elastomers (including vulcanized rubbers and thermoplastic elastomers such as EPDM, EPR, and SEBS), as these compositions are described in WO 02/18487, WO 02/31044, and WO 03/048252.

High Purity Hydrocarbon Fluids

In another embodiment, the nonfunctionalized plasticizer (NFP) is a high purity hydrocarbon fluid of lubricating viscosity comprising a mixture of $C_{20}$ to $C_{120}$ paraffins, 50 wt % or more being isoparaffinic hydrocarbons and less than 50 wt % being hydrocarbons that contain naphthenic and/or aromatic structures. Preferably, the mixture of paraffins comprises a wax isomerate lubricant base stock or oil, which includes:

1. hydroisomerized natural and refined waxes, such as slack waxes, deoiled waxes, normal alpha-olefin waxes, microcrystalline waxes, and waxy stocks derived from gas oils, fuels hydrocracker bottoms, hydrocarbon raffinates, hydrocracked hydrocarbons, lubricating oils, mineral oils, polyalphaolefins, or other linear or branched hydrocarbon compounds with carbon number of about 20 or more; and
2. hydroisomerized synthetic waxes, such as Fischer-Tropsch waxes (i.e., the high boiling point residues of Fischer-Tropsch synthesis, including waxy hydrocarbons);

or mixtures thereof. Most preferred are lubricant base stocks or oils derived from hydrocarbons synthesized in a Fischer-Tropsch process as part of an overall Gas-to-Liquids (GTL) process.

In one embodiment, the mixture of paraffins has:
1. a naphthenic content of less than 40 wt %, preferably less than 30 wt %, preferably less than 20 wt %, preferably less than 15 wt %, preferably less than 10 wt %, preferably less than 5 wt %, preferably less than 2 wt %, preferably less than 1 wt % (based on the total weight of the hydrocarbon mixture); and/or
2. a normal paraffins content of less than 5 wt %, preferably less than 4 wt %, preferably less than 3 wt %, preferably less than 1 wt % (based on the total weight of the hydrocarbon mixture); and/or
3. an aromatic content of 1 wt % or less, preferably 0.5 wt % or less; and/or
4. a saturates level of 90 wt % or higher, preferably 95 wt % or higher, preferably 98 wt % or higher, preferably 99 wt % or higher; and/or
5. the percentage of carbons in chain-type paraffinic structures ($C_P$) of 80% or more, preferably 90% or more, preferably 95% or more, preferably 98% or more; and/or
6. a branched paraffin:normal paraffin ratio greater than about 10:1, preferably greater than 20:1, preferably greater than 50:1, preferably greater than 100:1, preferably greater than 500:1, preferably greater than 1000:1; and/or
7. sidechains with 4 or more carbons making up less than 10% of all sidechains, preferably less than 5%, preferably less than 1%; and/or
8. sidechains with 1 or 2 carbons making up at least 50% of all sidechains, preferably at least 60%, preferably at least 70%, preferably at least 80%, preferably at least 90%, preferably at least 95%, preferably at least 98%; and/or
9. a sulfur content of 300 ppm or less, preferably 100 ppm or less, preferably 50 ppm or less, preferably 10 ppm or less (where ppm is on a weight basis); and/or
10. a nitrogen content of 300 ppm or less, preferably 100 ppm or less, preferably 50 ppm or less, preferably 10 ppm or less (where ppm is on a weight basis).

In another embodiment, the mixture of paraffins has:
1. a number-average molecular weight of 300 to 1800 g/mol, preferably 400 to 1500 g/mol, preferably 500 to 1200 g/mol, preferably 600 to 900 g/mol; and/or
2. a kinematic viscosity at 40° C. of 10 cSt or more, preferably 25 cSt or more, preferably between about 50 and 400 cSt; and/or
3. a kinematic viscosity at 100° C. ranging from 2 to 50 cSt, preferably 3 to 30 cSt, preferably 5 to 25 cSt, preferably 6 to 20 cSt, more preferably 8 to 16 cSt; and/or
4. a viscosity index (VI) of 80 or greater, preferably 100 or greater, preferably 120 or greater, preferably 130 or greater, preferably 140 or greater, preferably 150 or greater, preferably 160 or greater, preferably 180 or greater; and/or
5. a pour point of −5° C. or lower, preferably −10° C. or lower, preferably −15° C. or lower, preferably −20° C. or lower, preferably −25° C. or lower, preferably −30° C. or lower; and/or 6. a flash point of 200° C. or more, preferably 220° C. or more, preferably 240° C. or more, preferably 260° C. or more; and/or
7. a specific gravity (15.6° C./15.6° C.) of 0.86 or less, preferably 0.85 or less, preferably 0.84 or less; and/or
8. an aniline point of 120° C. or more; and/or
9. a bromine number of 1 or less.

In a preferred embodiment, the mixture of paraffins comprises a GTL base stock or oil. GTL base stocks and oils are fluids of lubricating viscosity that are generally derived from waxy synthesized hydrocarbons, that are themselves derived via one or more synthesis, combination, transformation, and/or rearrangement processes from gaseous carbon-containing compounds and hydrogen-containing compounds as feedstocks, such as: hydrogen, carbon dioxide, carbon monoxide, water, methane, ethane, ethylene, acetylene, propane, propylene, propyne, butane, butylenes, and butynes. Preferably, the feedstock is "syngas" (synthesis gas, essentially CO and $H_2$) derived from a suitable source, such as natural gas and/or coal. GTL base stocks and oils include wax isomerates, comprising, for example, hydroisomerized synthesized waxes, hydroisomerized Fischer-Tropsch (F-T) waxes (including waxy hydrocarbons and possible analogous oxygenates), or mixtures thereof. GTL base stocks and oils may further comprise other hydroisomerized base stocks and base oils. Particularly preferred GTL base stocks or oils are those comprising mostly hydroisomerized F-T waxes and/or other liquid hydrocarbons obtained by a F-T synthesis process.

The synthesis of hydrocarbons, including waxy hydrocarbons, by F-T may involve any suitable process known in the art, including those involving a slurry, a fixed-bed, or a fluidized-bed of catalyst particles in a hydrocarbon liquid. The catalyst may be an amorphous catalyst, for example based on a Group VIII metal such as Fe, Ni, Co, Ru, and Re on a suitable inorganic support material, or a crystalline catalyst, for example a zeolitic catalyst. The process of making a lubricant base stock or oil from a waxy stock is characterized as a hydrodewaxing process. A hydrotreating step, while typically not required for F-T waxes, can be performed prior to hydrodewaxing if desired. Some F-T waxes may benefit from removal of oxygenates while others may benefit from oxygenates treatment prior to hydrodewaxing. The hydrodewaxing process is typically conducted over a catalyst or combination of catalysts at high temperatures and pressures in the presence of hydrogen. The catalyst may be an amorphous catalyst, for example based on Co, Mo, W, etc. on a suitable oxide support material, or a crystalline catalyst, for example a zeolitic catalyst such as ZSM-23 and ZSM-48 and others disclosed in U.S. Pat. No. 4,906,350, often used in conjunction with a Group VIII metal such as Pd or Pt. This process may be followed by a solvent and/or catalytic dewaxing step to lower the pour point of the hydroisomerate. Solvent dewaxing involves the physical fractionation of waxy components from the hydroisomerate. Catalytic dewaxing converts a portion of the hydroisomerate to lower boiling hydrocarbons; it often involves a shape-selective molecular sieve, such as a zeolite or silicoaluminophosphate material, in combination with a catalytic metal component, such as Pt, in a fixed-bed, fluidized-bed, or slurry type process at high temperatures and pressures in the presence of hydrogen.

Useful catalysts, processes, and compositions for GTL base stocks and oils, Fischer-Tropsch hydrocarbon derived base stocks and oils, and wax isomerate hydroisomerized base stocks and oils are described in, for example, U.S. Pat. Nos. 2,817,693; 4,542,122; 5,545,674; 4,568,663; 4,621,072; 4,663,305; 4,897,178; 4,900,407; 4,921,594; 4,923,588; 4,937,399; 4,975,177; 5,059,299; 5,158,671; 5,182,248; 5,200,382; 5,290,426; 5,516,740; 5,580,442; 5,885,438; 5,935,416; 5,935,417; 5,965,475; 5,976,351; 5,977,425; 6,025,305; 6,080,301; 6,090,989; 6,096,940; 6,103,099; 6,165,949; 6,190,532; 6,332,974; 6,375,830; 6,383,366; 6,475,960; 6,620,312; and 6,676,827; European Patents EP 324528, EP 532116, EP 532118, EP 537815, EP 583836, EP 666894, EP 668342, EP 776959; WPO patent applications WO 97/31693, WO 99/20720, WO 99/45085, WO 02/64710, WO 02/64711, WO 02/70627, WO 02/70629, WO 03/33320; and British Patents 1,350,257; 1,390,359; 1,429,494; and 1,440,230. Particularly favorable processes are described in European Patent Applications EP 464546 and EP 464547. Processes using Fischer-Tropsch wax feeds are described in U.S. Pat. Nos. 4,594,172; 4,943,672; 6,046,940; 6,103,099; 6,332,974; 6,375,830; and 6,475,960.

This invention also relates to plasticized polyolefin compositions comprising one or more polyolefins and one or more non-functionalized plasticizers, where one or more NFP is a high purity hydrocarbon fluid derived from a GTL process comprising a mixture of paraffins of carbon number ranging from about $C_{20}$ to $C_{100}$, a molar ratio of isoparaffins: n-paraffins greater than about 50:1, the percentage of carbons in paraffinic structures ($C_P$) of 98% or more, a pour point ranging from about −20 to −60° C., and a kinematic viscosity at 100° C. ranging from about 6 to 20 cSt.

As used herein, the following terms have the indicated meanings: "naphthenic" describes cyclic (mono-ring and/or multi-ring) saturated hydrocarbons (i.e., cycloparaffins) and branched cyclic saturated hydrocarbons; "aromatic" describes cyclic (mono-ring and/or multi-ring) unsaturated hydrocarbons and branched cyclic unsaturated hydrocarbons; "hydroisomerized" describes a catalytic process in which normal paraffins and/or slightly branched isoparaffins are converted by rearrangement into more branched isoparaffins (also known as "isodewaxing"); "wax" is a hydrocarbonaceous material existing as a solid at or near room temperature, with a melting point of 0° C. or above, and consisting predominantly of paraffinic molecules, most of which are normal paraffins; "slack wax" is the wax recovered from petroleum oils such as by solvent dewaxing, and may be further hydrotreated to remove heteroatoms.

Group III Basestocks or Mineral Oils

In another embodiment, the NFP comprises a Group III hydrocarbon oil (also called a Group III lubricant basestock or Group III mineral oil). Preferably the NFP has a saturates levels of 90% or more (preferably 92% or more, preferably 94% or more, preferably 95% or more, preferably 98% or more); and a sulfur content less than 0.03% (preferably between 0.001 and 0.01%); and a VI of 120 or more (preferably 130 or more). Preferably the Group III hydrocarbon oil has a kinematic viscosity at 100° C. of 3 to 50, preferably 4 to 40 cSt, preferably 6 to 30 cSt, preferably 8 to 20; and/or a number average molecular weight of 300 to 5,000 g/mol, preferably 400 to 2,000 g/mol, more preferably 500 to 1,000 g/mol. Preferably the Group III hydrocarbon oil has a pour point of −10° C. or less, a flash point of 200° C. or more, and a specific gravity (15.6° C./15.6° C.) of 0.86 or less.

Desirable Group III basestocks are commercially available from a number of sources and include those described in Table F. The percentage of carbons in chain-type paraffinic structures ($C_P$) in such liquids is greater than 80%.

TABLE F

Commercially available Group III Basestocks

| | KV @ 100° C., cSt | VI | Pour Point, ° C. | Specific gravity | Flash Point, ° C. |
|---|---|---|---|---|---|
| UCBO 4R[1] | 4.1 | 127 | −18 | 0.826 | 216 |
| UCBO 7R[1] | 7.0 | 135 | −18 | 0.839 | 250 |
| Nexbase 3043[2] | 4.3 | 124 | −18 | 0.831 | 224 |
| Nexbase 3050[2] | 5.1 | 126 | −15 | 0.835 | 240 |
| Nexbase 3060[2] | 6.0 | 128 | −15 | 0.838 | 240 |
| Nexbase 3080[2] | 8.0 | 128 | −15 | 0.843 | 260 |
| Yubase YU-4[3] | 4.2 | 122 | −15 | 0.843 | 230 |
| Yubase YU-6[3] | 6.5 | 131 | −15 | 0.842 | 240 |
| Yubase YU-8[3] | 7.6 | 128 | −12 | 0.850 | 260 |
| Ultra-S 4[4] | 4.3 | 123 | −20 | 0.836 | 220 |
| Ultra-S 6[4] | 5.6 | 128 | −20 | 0.839 | 234 |
| Ultra-S 8[4] | 7.2 | 127 | −15 | 0.847 | 256 |
| VHVI 4[5] | 4.6 | 128 | −21 | 0.826 | |
| VHVI 8[5] | 8.0 | 127 | −12 | 0.850 | 248 |
| Visom 4[6] | 4.0 | | | | 210 |
| Visom 6[6] | 6.6 | 148 | −18 | 0.836 | 250 |

[1]Available from ChevronTexaco (USA).
[2]Available from Neste Oil (Finland).
[3]Available from SK Corp (South Korea).
[4]Available from ConocoPhillips (USA)/S-Oil (South Korea).
[5]Available from PetroCanada (Canada).
[6]Available from ExxonMobil (USA).

General Characteristics of Useful NFPs

In preferred embodiments, the NFP has a kinematic viscosity at 100° C. ($KV_{100}$) of 4 cSt or more, preferably 5 cSt or more, preferably 6 to 5000 cSt, preferably 8 to 3000 cSt, preferably 10 to 1000 cSt, preferably 12 to 500 cSt, preferably 15 to 350 cSt, preferably 35 to 300 cSt, preferably 40 to 200 cSt, preferably 8 to 300 cSt, preferably 6 to 150 cSt, preferably 10 to 100 cSt, preferably less than 50 cSt, wherein a desirable range may be any combination of any lower $KV_{100}$ limit with any upper $KV_{100}$ limit described herein. In other embodiments, the NFP has a kinematic viscosity at 100° C. of less than 2 cSt.

In preferred embodiments, the NFP has a pour point of −10° C. or less, preferably −20° C. or less, preferably −30° C. or less, preferably −40° C. or less, preferably −45° C. or less, preferably −50° C. or less, preferably −10 to −100° C., preferably −15 to −80° C., preferably −15 to −75° C., preferably −20 to −70° C., preferably −25 to −65° C., preferably greater than −120° C., wherein a desirable range may be any combination of any lower pour point limit with any upper pour point limit described herein. In another embodiment, the NFP has a pour point of less than −30° C. when the kinematic viscosity at 40° C. is from 0.5 to 200 cSt. Most mineral oils, which typically include aromatic moieties and other functional groups, have a pour point of from 10 to −20° C. in the same kinematic viscosity range.

In a preferred embodiment, the NFP has a glass transition temperature ($T_g$) of −40° C. or less (preferably −50° C. or less, preferably −60° C. or less, preferably −70° C. or less, preferably −80° C. or less, preferably −45 to −120° C., preferably −65 to −90° C., wherein a desirable range may be any combination of any lower $T_g$ limit with any upper $T_g$ limit described herein.

In preferred embodiments, the NFP has a Viscosity Index (VI) of 90 or more, preferably 100 or more, preferably 110 or more, preferably 120 or more, preferably 130 or more, preferably 115 to 350, preferably 135 to 300, preferably 140 to 250, preferably 150 to 200, preferably 125 to 180, wherein a desirable range may be any combination of any lower VI limit with any upper VI limit described herein.

In preferred embodiments, the NFP has a flash point of 200° C. or greater, preferably 210° or greater, preferably 230° C. or greater, preferably 200 to 350° C., preferably 210 to 300° C., preferably 215 to 290° C., preferably 220 to 280° C., preferably 240 to 280° C., wherein a desirable range may be any combination of any lower flash point limit with any upper flash point limit described herein.

In preferred embodiments, the NFP has a specific gravity of 0.86 or less, preferably 0.855 or less, preferably 0.84 or less, preferably 0.78 to 0.86, preferably 0.79 to 0.855, preferably 0.80 to 0.85, preferably 0.81 to 0.845, preferably 0.82 to 0.84, wherein a desirable range may be any combination of any lower specific gravity limit with any upper specific gravity limit described herein.

In preferred embodiments, the NFP has a number-average molecular weight ($M_n$) of 250 g/mol or more, preferably 300 g/mol or more, preferably 500 g/mol or more, preferably 300 to 21,000 g/mol, preferably 300 to 10,000 g/mol, preferably 400 to 5,000 g/mol, preferably 500 to 3,000 g/mol, preferably 10 kg/mol or less, preferably 5 kg/mol or less, preferably 3 kg/mol or less, preferably 2 kg/mol or less, preferably 1 kg/mol or less, wherein a desirable range may be any combination of any lower $M_n$ limit with any upper $M_n$ limit described herein.

In preferred embodiments, the NFP has a low degree of color, such as typically identified as "water white", "prime white", "standard white", or "bright and clear," preferably an APHA color of 100 or less, preferably 80 or less, preferably 60 or less, preferably 40 or less, preferably 20 or less, as determined by ASTM D1209.

In other embodiments, any NFP may have an initial boiling point (ASTM D1160) of from 300 to 600° C. in one embodiment, and from 350 to 500° C. in another embodiment, and greater than 400° C. in yet another embodiment.

Any of the NFP's for use in the present invention may be described by any embodiment described herein, or any combination of the embodiments described herein. For example, in one embodiment, the NFP is a $C_6$ to $C_{200}$ paraffin having a pour point of less than −25° C. Alternately, the NFP comprises an aliphatic hydrocarbon having a kinematic viscosity of from 0.1 to 1000 cSt at 100° C. Alternately, the NFP is selected from isoparaffins and PAOs and blends thereof having from 8 to 25 carbon atoms.

In another embodiment, the NFP of the present invention comprises $C_{25}$ to $C_{1500}$ paraffins, and $C_{30}$ to $C_{500}$ paraffins in another embodiment, and has a flash point of 200° C. or more and a pour point of −10° C. or less and a viscosity index of 120 or more. Alternately the NFP comprises $C_{25}$ to $C_{1500}$ paraffins, preferably $C_{30}$ to $C_{500}$ paraffins, and has a flash point of 200° C. or more and a pour point of −20° C. or less. Alternately the NFP comprises $C_{25}$ to $C_{1500}$ paraffins, preferably $C_{30}$ to $C_{500}$ paraffins, and has a flash point of 200° C. or more and a kinematic viscosity at 100° C. of 35 cSt or more. In another embodiment, the NFP consists essentially of $C_{35}$ to $C_{300}$ paraffins, preferably the NFP consists essentially of $C_{40}$ to $C_{250}$ paraffins, and has a flash point of 200° C. or more and a pour point of −10° C. or less and a viscosity index of 120 or more. Alternately the NFP consists essentially of $C_{35}$ to $C_{300}$ paraffins, preferably $C_{40}$ to $C_{250}$ paraffins, and has a flash point of 200° C. or more and a pour point of −20° C. or less. Alternately the NFP consists essentially of $C_{35}$ to $C_{300}$ paraffins, preferably $C_{40}$ to $C_{250}$ paraffins, and has a flash point of 200° C. or more and a kinematic viscosity at 100° C. of 35 cSt or more. Alternately the NFP has a flash point of 200° C. or more and a pour point of −20° C. or less. Alternately the NFP has a flash point of 200° C. or more and a kinematic viscosity at 100° C. of 35 cSt or more.

In a preferred embodiment, any NFP described herein has a flash point of 200° C. or more (preferably 210° C. or more) and a pour point of −20° C. or less (preferably −25° C. or less, more preferably −30° C. or less, more preferably −35° C. or less, more preferably −45° C. or less, more preferably −50° C. or less).

In another preferred embodiment, the NFP has a flash point of 220° C. or more (preferably 230° C. or more) and a pour point of −10° C. or less (preferably −25° C. or less, more preferably −30° C. or less, more preferably −35° C. or less, more preferably −45° C. or less, more preferably −50° C. or less).

In another preferred embodiment, the NFP has a kinematic viscosity at 100° C. of 35 cSt or more (preferably 40 cSt or more, preferably 50 cSt or more, preferably 60 cSt or more) and a specific gravity (15.6/15.6° C.) of 0.87 or less (preferably 0.865 or less, preferably 0.86 or less, preferably 0.855 or less) and a flash point of 200° C. or more (preferably 230° C. or more).

In another preferred embodiment, the NFP has a) a flash point of 200° C. or more, b) a specific gravity of 0.86 or less, and c1) a pour point of −10° C. or less and a viscosity index of 120 or more, or c2) a pour point of −20° C. or less, or c3) a kinematic viscosity at 100° C. of 35 cSt or more.

In another preferred embodiment, the NFP has a specific gravity (15.6/15.6° C.) of 0.85 or less (preferably between 0.80 and 0.85) and a kinematic viscosity at 100° C. of 3 cSt or more (preferably 4 or more, preferably 5 cSt or more, preferably 8 cSt or more, preferably 10 cSt or more, preferably 15 cSt or more, preferably 20 cSt or more) and/or a number-average molecular weight ($M_n$) of at least 280 g/mol.

In another preferred embodiment, the NFP has a specific gravity (15.6/15.6° C.) of 0.86 or less (preferably between 0.81 and 0.855, preferably between 0.82 and 0.85) and a kinematic viscosity at 100° C. of 5 cSt or more (preferably 6 or more, preferably 8 cSt or more, preferably 10 cSt or more, preferably 12 cSt or more, preferably 15 cSt or more, preferably 20 cSt or more) and/or a number-average molecular weight ($M_n$) of at least 420 g/mol.

In another preferred embodiment, the NFP has a specific gravity (15.6/15.6° C.) of 0.87 or less (preferably between 0.82 and 0.87) and a kinematic viscosity at 100° C. of 10 cSt or more (preferably 12 cSt or more, preferably 14 cSt or more, preferably 16 cSt or more, preferably 20 cSt or more, preferably 30 cSt or more, preferably 40 cSt or more) and/or a number-average molecular weight ($M_n$) of at least 700 g/mol.

In another preferred embodiment, the NFP has a specific gravity (15.6/15.6° C.) of 0.88 or less (preferably 0.87 or less, preferably between 0.82 and 0.87) and a kinematic viscosity at 100° C. of 15 cSt or more (preferably 20 cSt or more, preferably 25 cSt or more, preferably 30 cSt or more, preferably 40 cSt or more) and/or a number-average molecular weight ($M_n$) of at least 840 g/mol.

In another preferred embodiment the NFP has a kinematic viscosity at 100° C. of 3 to 3000 cSt, preferably 6 to 300 cSt, more preferably 8 to 100 cSt; and a number average molecular weight ($M_n$) of 300 to 21,000 g/mol, preferably 500 to 5,000 g/mol, more preferably 600 to 3,000 g/mol.

In another preferred embodiment the NFP has a kinematic viscosity at 100° C. of 3 to 500 cSt, preferably 6 to 200 cSt, more preferably 8 to 100 cSt, more preferably 3 to 25 cSt; and a number average molecular weight ($M_n$) of 300 to 10,000 g/mol, preferably 400 to 5,000 g/mol, more preferably 500 to 2,500 g/mol, more preferably 300 to 1,200 g/mol.

In another preferred embodiment the NFP has a kinematic viscosity at 100° C. of 3 to 100 cSt, preferably 4 to 50 cSt, more preferably 6 to 25 cSt, more preferably 3 to 15 cSt; and a number average molecular weight ($M_n$) of 300 to 3,000 g/mol, preferably 350 to 2,000 g/mol, more preferably 400 to 1,000 g/mol, more preferably 300 to 800 g/mol.

In another preferred embodiment, the NFP has a pour point of −25° C. or less, preferably between −30° C. and −90° C., and a kinematic viscosity in the range of from 20 to 5000 cSt at 40° C. In another preferred embodiment, the NFP has a pour point of −25° C. or less and a Mn of 400 g/mol or greater. Most mineral oils, which typically include functional groups, have a pour point of from 10° C. to −25° C. at the same viscosity and molecular weight ranges.

In another preferred embodiment the NFP has kinematic viscosity at 100° C. of 3 cSt or greater, preferably 6 cSt or greater, more preferably 8 cSt or greater, and one or more of the following properties:

1. a pour point of −10° C. or less, preferably −20° C. or less, preferably −30° C. or less, preferably −40° C. or less; and/or,
2. a Viscosity Index of 120 or greater; and/or,
3. a low degree of color, such as typically identified as "water white", "prime white", "standard white", or "bright and clear," preferably an APHA color of 100 or less, preferably 80 or less, preferably 60 or less, preferably 40 or less, preferably 20 or less, preferably 15 or less as determined by ASTM D1209; and/or
4. a flash point of 200° C. or more, preferably 220° C. or more, preferably 240° C. or more; and/or
5. a specific gravity (15.6° C.) of less than 0.86.

Most mineral oils at the same viscosity range have a pour point greater than −20° C. or an APHA color of greater than 20 or a specific gravity (15.6° C.) of 0.86 or more.

In another preferred embodiment, the NFP has a Viscosity Index of 120 or more and one or more of the following properties:

1. a pour point of −10° C. or less, preferably −20° C. or less, preferably −30° C. or less, preferably −40° C. or less; and/or,
2. a kinematic viscosity at 100° C. of 3 cSt or greater, preferably 6 cSt or greater, preferably 8 cSt or greater, preferably 10 cSt or greater; and/or,
3. a low degree of color, such as typically identified as "water white", "prime white", "standard white", or "bright and clear," preferably an APHA color of 100 or less, preferably 80 or less, preferably 60 or less, preferably 40 or less, preferably 20 or less, preferably 15 or less, as determined by ASTM D1209; and/or
4. a flash point of 200° C. or more, preferably 220° C. or more, preferably 240° C. or more; and/or
5. a specific gravity (15.6° C.) of less than 0.86.

Most mineral oils have a Viscosity Index of less than 120.

In another preferred embodiment, the NFP has a pour point of −20° C. or less, preferably −30° C. or less, and one or more of the following properties:

1. a kinematic viscosity at 100° C. of 3 cSt or greater, preferably 6 cSt or greater, preferably 8 cSt or greater, preferably 10 cSt or more; and/or,
2. a Viscosity Index of 120 or greater, preferably 130 or greater; and/or,
3. a low degree of color, such as typically identified as "water white", "prime white", "standard white", or "bright and clear," preferably APHA color of 100 or less, preferably 80 or less, preferably 60 or less, preferably 40 or less, preferably 20 or less, preferably 15 or less as determined by ASTM D 1209
4. a flash point of 200° C. or more, preferably 220° C. or more, preferably 240° C. or more; and/or
5. a specific gravity (15.6° C.) of less than 0.86.

Most mineral oils have a kinematic viscosity at 100° C. of less than 6 cSt, or an APHA color of greater than 20, or a flash point less than 200° C. when their pour point is less than −20° C.

In another preferred embodiment the NFP has a glass transition temperature ($T_g$) that cannot be determined by ASTM E 1356 or, if it can be determined, then the $T_g$ according to ASTM E 1356 is less than 0° C., preferably less than −10° C., more preferably less than −20° C., more preferably less than −30° C., more preferably less than −40° C., and, preferably, also has one or more of the following properties:
1. an initial boiling point as determined by ASTM D 1160 greater than 300° C., preferably greater than 350° C., preferably greater than 400° C.; and/or
2. a pour point of −10° C. or less, preferably −15° C. or less, preferably −25° C. or less, preferably −35° C. or less, preferably −45° C. or less; and/or
3. a specific gravity (ASTM D 4052, 15.6/15.6° C.) of less than 0.88, preferably less than 0.86, preferably less than 0.84, preferably from 0.80 to 0.88, preferably from 0.82 to 0.86; and/or
4. a final boiling point as determined by ASTM D1160 of from 300° C. to 800° C., preferably from 400° C. to 700° C., preferably greater than 500° C.; and/or
5. a weight average molecular weight ($M_w$) between 30,000 and 400 g/mol preferably between 15,000 and 500 g/mol, more preferably between 5,000 and 600 g/mol; and/or
6. a number average molecular weight ($M_n$) between 10,000 and 400 g/mol, preferably between 5,000 and 500 g/mol, more preferably between 2,000 and 600 g/mol; and/or
7. a flash point as measured by ASTM D 92 of 200° C. or greater, and/or In certain particularly preferred embodiments, the NFP has a specific gravity of 0.86 or less (preferably 0.855 or less, preferably 0.85 or less), and one or more of the following:
a) a VI of 120 or more (preferably 135 or more, preferably 140 or more), and/or
b) a flash point of 200° C. or more (preferably 220° C. or more, preferably 240° C. or more).

In certain particularly preferred embodiments, the NFP has a pour point of −10° C. or less (preferably −15° C. or less, preferably −20° C. or less, preferably −25° C. or less), a VI of 120 or more (preferably 135 or more, preferably 140 or more), and optionally a flash point of 200° C. or more (preferably 220° C. or more, preferably 240° C. or more).

In certain particularly preferred embodiments, the NFP has a pour point of −20° C. or less (preferably −25° C. or less, preferably −30° C. or less, preferably −40° C. or less) and one or more of the following:
a) a flash point of 200° C. or more (preferably 220° C. or more, preferably 240° C. or more), and/or
b) a VI of 120 or more (preferably 135 or more, preferably 140 or more), and/or
c) a KV100 of 4 cSt or more (preferably 6 cSt or more, preferably 8 cSt or more, preferably 10 cSt or more), and/or
d) a specific gravity of 0.86 or less (preferably 0.855 or less, preferably 0.85 or less).

In certain particularly preferred embodiments, the NFP has a KV100 of 4 cSt or more (preferably 5 cSt or more, preferably 6 cSt or more, preferably 8 cSt or more, preferably 10 cSt or more), a specific gravity of 0.86 or less (preferably 0.855 or less, preferably 0.85 cSt or less), and a flash point of 200° C. or more (preferably 220° C. or more, preferably 240° C. or more).

In a preferred embodiment, the NFP has a flash point of 200° C. or more (preferably 220° C. or more, preferably 240° C. or more), a pour point of −10° C. or less (preferably −15° C. or less, preferably −20° C. or less, preferably −25° C. or less), a specific gravity of 0.86 or less (preferably 0.855 or less, preferably 0.85 or less), a KV100 of 4 cSt or more (preferably 5 cSt or more, preferably 6 cSt or more, preferably 8 cSt or more, preferably 10 cSt or more), and optionally a VI of 100 or more (preferably 120 or more, preferably 135 or more).

In a preferred embodiment, the NFP has a KV100 of 35 cSt or more (preferably 40 or more) and a specific gravity of 0.86 or less (preferably 0.855 or less), and optionally one or more of the following:
a) a flash point of 200° C. or more (preferably 220° C. or more, preferably 240° C. or more), and/or
b) a pour point of −10° C. or less (preferably −15° C. or less, preferably −20° C. or less, preferably −25° C. or less).

In a preferred embodiment, the NFP has a flash point of 200° C. or more (preferably 210° C. or more, preferably 220° C. or more), a pour point of −10° C. or less (preferably −20° C. or less, preferably −30° C. or less), and a KV100 of 6 cSt or more (preferably 8 cSt or more, preferably 10 cSt or more, preferably 15 cSt or more).

In a preferred embodiment, the NFP has a pour point of −40° C. or less (preferably −50° C. or less) and a specific gravity of 0.84 or less (preferably 0.83 or less).

In a preferred embodiment, the percentage of carbons in chain-type paraffins ($C_P$) for any NFP is at least 80% (preferably at least 85%, more preferably at least 90%, even more preferably at least 95%, even more preferably at least 98%, most preferably at least 99%).

Preferred compositions of the present invention can be characterized in that the glass transition temperature ($T_g$) of the composition decreases by at least 1° C. (preferably at least 2° C., preferably at least 3° C., preferably at least 4° C., preferably at least 5° C., preferably at least 6° C., preferably at least 7° C., preferably at least 8° C., preferably at least 9° C. preferably at least 10° C.) for every 1 wt % of NFP present in the composition, while the peak melting and crystallization temperatures of the polyolefin remain within 5° C. (preferably within 4° C., preferably within 3° C., preferably within 2° C.) of their values for the unplasticized polyolefin.

Preferred compositions of the present invention can be characterized in that the glass transition temperature ($T_g$) of the plasticized composition is at least 2° C. (preferably at least 4° C., preferably at least 6° C., preferably at least 8° C., preferably at least 10° C., preferably at least 12° C., preferably at least 15° C., preferably at least 20° C., preferably at least 25° C., preferably at least 30° C.) lower than that of the unplasticized polyolefin, while the peak melting and crystallization temperatures of the polyolefin remain within 5° C. (preferably within 4° C., preferably within 3° C., preferably within 2° C.) of their values for the unplasticized polyolefin.

Preferred compositions of the present invention can be characterized in that the glass transition temperature ($T_g$) of at least one propylene polymer in the composition decreases by at least 1° C. (preferably at least 2° C., preferably at least 3° C., preferably at least 4° C., preferably at least 5° C., preferably at least 6° C., preferably at least 7° C., preferably at least 8° C., preferably at least 9° C., preferably at least 10° C.) for every 1 wt % of NFP present in the composition, while the peak melting and crystallization temperatures of the polyolefin remain within 5° C. (preferably within 4° C., preferably within 3° C., preferably within 2° C.) of their values for the unplasticized polyolefin.

Preferred compositions of the present invention can be characterized in that the glass transition temperature ($T_g$) of at least one propylene polymer in the plasticized composition is at least 2° C. (preferably at least 4° C., preferably at least 6° C., preferably at least 8° C., preferably at least 10° C., preferably at least 12° C., preferably at least 15° C., preferably at least 20° C., preferably at least 25° C., preferably at least 30° C.) lower than that of the unplasticized polyolefin, while the peak melting and crystallization temperatures of the polyolefin remain within 5° C. (preferably within 4° C., preferably within 3° C., preferably within 2° C.) of their values for the unplasticized polyolefin.

Preferred compositions of the present invention can be characterized in that the plasticized composition decreases less than 3% (preferably less than 2%, preferably less than 1%) in weight when permanence of the NFP is determined by ASTM D1203 (0.25 mm thick sheet, 300 hours in dry 70° C. oven). Weight loss here refers to the reduction in weight in excess of that measured for the unplasticized composition under the same test conditions.

Preferred NFP's of this invention are characterized in that, when blended with the polyolefin to form a plasticized composition, the NFP is miscible with the polyolefin as indicated by no change in the number of tan-delta peaks in the Dynamic Mechanical Thermal Analysis (DMTA) trace as compared to the unplasticized polyolefin DMTA trace (the "trace" is the plot of tan-delta vs temperature). Lack of miscibility is indicated by an increase in the number of tan-delta peaks in DMTA trace over those in the unplasticized polyolefin Polyolefin The NFP's and nucleating agents described herein are blended with at least one polyolefin to prepare the plasticized compositions of this invention. Preferred polyolefins include propylene polymers and blends, ethylene polymers and blends, and butene polymers and blends.

Preferred olefin homopolymers and copolymers useful as polyolefins in this invention typically have one or more of:
1. an $M_w$ of 30,000 to 2,000,000 g/mol preferably 50,000 to 1,000,000, more preferably 90,000 to 500,000, as measured by GPC; and/or
2. an $M_w/M_n$ of 1 to 40, preferably 1.6 to 20, more preferably 1.8 to 10, more preferably 1.8 to 3 as measured by GPC; and/or
3. a $T_m$ (second melt) of 30 to 200° C., preferably 30 to 185° C., preferably 50 to 175, more preferably 60 to 170 as measured by DSC; and/or
4. a crystallinity of 5 to 80%, preferably 10 to 70%, preferably 20 to 60%, preferably at least 30%, preferably at least 40%, preferably at least 50%, as determined by DSC; and/or
5. a glass transition temperature ($T_g$) of −40° C. to 20° C., preferably −20° C. to 10° C., more preferably −10° C. to 5° C. as measured by DMTA; and or
6. a heat of fusion ($H_f$) of 180 J/g or less, preferably 20 to 150 J/g, more preferably 40 to 120 J/g as measured by the DSC method described below in the test methods; and or
7. a crystallization temperature ($T_c$) of 15 to 120° C., preferably 20 to 115° C., more preferably 25 to 110° C., preferably 60 to 145° C., as measured by DSC; and or
8. a heat deflection temperature of 45 to 140° C., preferably 60 to 135° C., more preferably 75 to 125° C.; and or
9. A Rockwell hardness (R scale) of 25 or more, preferably 40 or more, preferably 60 or more, preferably 80 or more, preferably 100 or more, preferably from 25 to 125; and or
10. A branching index (g') of 0.2 to 2.0, preferably 0.5 to 1.5, preferably 0.7 to 1.1, as measured by SEC-3D.

Propylene Polymers and Blends

In one aspect of the invention, the polyolefin is selected from polypropylene (propylene homopolymer and copolymers) and blends thereof. The homopolymer may be atactic polypropylene, isotactic polypropylene, syndiotactic polypropylene and blends thereof. The copolymer can be a random copolymer, a statistical copolymer, a block copolymer, and blends thereof. In particular, the inventive polymer blends described herein include impact copolymers, elastomers and plastomers, any of which may be physical blends or in situ blends with the polypropylene. The method of making the polypropylene is not critical, as it can be made by slurry, solution, gas phase or other suitable processes, and by using catalyst systems appropriate for the polymerization of polyolefins, such as Ziegler-Natta-type catalysts, metallocene-type catalysts, other appropriate catalyst systems or combinations thereof. In a preferred embodiment the propylene polymers are made by the catalysts, activators and processes described in U.S. Pat. Nos. 6,342,566, 6,384,142, WO 03/040201, WO 97/19991 and U.S. Pat. No. 5,741,563. Likewise the impact copolymers may be prepared by the process described in U.S. Pat. Nos. 6,342,566, 6,384,142. Such catalysts are well known in the art, and are described in, for example, ZIEGLER CATALYSTS (Gerhard Fink, Rolf Mülhaupt and Hans H. Brintzinger, eds., Springer-Verlag 1995); Resconi et al., *Selectivity in Propene Polymerization with Metallocene Catalysts,* 100 CHEM. REV. 1253-1345 (2000); and I, II METALLOCENE-BASED POLYOLEFINS (Wiley & Sons 2000).

The polyolefin may be a propylene homopolymer or copolymer. In one embodiment the propylene homopolymer or copolymer has a molecular weight distribution ($M_w/M_n$) of up to 40, preferably ranging from 1.5 to 10, and from 1.8 to 7 in another embodiment, and from 1.9 to 5 in yet another embodiment, and from 2.0 to 4 in yet another embodiment. In another embodiment the polyolefin (preferably a propylene homopolymer or copolymer) has a Gardner impact strength, tested on 0.125 inch disk at 23° C., that may range from 20 in-lb to 1000 in-lb in one embodiment, and from 30 in-lb to 500 in-lb in another embodiment, and from 40 in-lb to 400 in-lb in yet another embodiment. In yet another embodiment, the 1% secant flexural modulus may range from 100 MPa to 2300 MPa, and from 200 MPa to 2100 MPa in another embodiment, and from 300 MPa to 2000 MPa in yet another embodiment, wherein the polyolefin (preferably a propylene homopolymer or copolymer) may exhibit any combination of any upper flexural modulus limit with any lower flexural modulus limit. The melt flow rate (MFR) (ASTM D 1238, 230° C., 2.16 kg) of preferred propylene polymers range from 0.1 dg/min to 2500 dg/min in one embodiment, and from 0.3 to 500 dg/min in another embodiment.

The propylene homopolymer or propylene copolymer useful in the present invention may have some level of isotacticity. Thus, in one embodiment, a polyolefin comprising isotactic polypropylene is a useful polymer in the invention of this patent, and similarly, highly isotactic polypropylene is useful in another embodiment. As used herein, "isotactic" is defined as having at least 10% isotactic pentads according to analysis by $^{13}$C-NMR. As used herein, "highly isotactic" is defined as having at least 60% isotactic pentads according to analysis by $^{13}$C-NMR. In a desirable embodiment, a polypropylene homopolymer having at least 85% isotacticity is the polyolefin, and at least 90% isotacticity in yet another embodiment.

In another desirable embodiment, a propylene polymer (preferably a propylene homopolymer) having at least 85% syndiotacticity is the polyolefin, and at least 90% syndiotacticity in yet another embodiment. As used herein, "syndiotactic" is defined as having at least 10% syndiotactic pentads according to analysis by $^{13}$C-NMR. As used herein, "highly syndiotactic" is defined as having at least 60% syndiotactic pentads according to analysis by $^{13}$C-NMR.

In another embodiment the propylene polymer (preferably propylene homopolymer) may be isotactic, highly isotactic, syndiotactic, highly syndiotactic or atactic. Atactic polypropylene is defined to be less than 10% isotactic or syndiotactic pentads. Preferred atactic polypropylenes typically have an Mw of 20,000 up to 1,000,000.

Preferred propylene polymers that are useful in this invention include those sold under the tradenames ACHIEVE™ and ESCORENE™ by ExxonMobil Chemical Company in Houston Tex.

In another embodiment of the invention, the polyolefin is a propylene copolymer, either random, or block, of propylene derived units and units selected from ethylene and $C_4$ to $C_{20}$ α-olefin derived units, typically from ethylene and $C_4$ to $C_{10}$ α-olefin derived units in another embodiment. The ethylene or $C_4$ to $C_{20}$ α-olefin derived units are present from 0.1 wt % to 50 wt % of the copolymer in one embodiment, and from 0.5 to 30 wt % in another embodiment, and from 1 to 15 wt % in yet another embodiment, and from 0.1 to 5 wt % in yet another embodiment, wherein a desirable copolymer comprises ethylene and $C_4$ to $C_{20}$ α-olefin derived units in any combination of any upper wt % limit with any lower wt % limit described herein. The propylene copolymer will have a weight average molecular weight of from greater than 8,000 g/mol in one embodiment, and greater than 10,000 g/mol in another embodiment, and greater than 12,000 g/mol in yet another embodiment, and greater than 20,000 g/mol in yet another embodiment, and less than 1,000,000 g/mol in yet another embodiment, and less than 800,000 in yet another embodiment, wherein a desirable copolymer may comprise any upper molecular weight limit with any lower molecular weight limit described herein.

Particularly desirable propylene copolymers have a molecular weight distribution ($M_w/M_n$) ranging from 1.5 to 10, and from 1.6 to 7 in another embodiment, and from 1.7 to 5 in yet another embodiment, and from 1.8 to 4 in yet another embodiment. The Gardner impact strength, tested on 0.125 inch disk at 23° C., of the propylene copolymer may range from 20 in-lb to 1000 in-lb in one embodiment, and from 30 in-lb to 500 in-lb in another embodiment, and from 40 in-lb to 400 in-lb in yet another embodiment. In yet another embodiment, the 1% secant flexural modulus of the propylene copolymer ranges from 100 MPa to 2300 MPa, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) of propylene copolymer ranges from 0.1 dg/min to 2500 dg/min in one embodiment, and from 0.3 to 500 dg/min in another embodiment.

In another embodiment the polyolefin may be a propylene copolymer comprising propylene and one or more other comonomers selected from the group consisting of ethylene and $C_4$ to $C_{20}$ linear, branched or cyclic monomers. In a preferred embodiment, the comonomer is selected from ethylene, 1-butene, 1-pentene, 1-hexene, 1-heptene, 1-octene, 1-nonene, 1-decene, 1-dodecene, 4-methyl-1-pentene, 3-methyl-1-pentene, and 3,5,5-trimethyl-1-hexene, and 5-ethyl-1-nonene. In a particularly preferred embodiment, the comonomer is selected from ethylene, 1-butene, 1-hexene, and 1-octene. Comonomers may be present at up to 50 wt %, preferably from 0 to 40 wt %, more preferably from 0.5 to 30 wt %, more preferably from 2 to 30 wt %, more preferably from 5 to 20 wt %.

Preferred aromatic-group-containing comonomers for any polyolefin copolymer useful in the present invention contain up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, alkyl benzene, and indene, especially styrene, paramethyl styrene, 4-phenyl-1-butene and alkyl benzene.

Preferred non-aromatic cyclic group containing comonomers for any polyolefin copolymer useful in the present invention can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Preferred diolefin comonomers for any polyolefin copolymer useful in the present invention include any $C_4$ to $C_{30}$ hydrocarbon having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes ($M_w$ less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions. In a preferred embodiment one or more dienes are present in the polyolefin at up to 10 wt %, preferably at 0.00001 to 1.0 wt %, preferably 0.002 to 0.5 wt %, even more preferably 0.003 to 0.2 wt %, based upon the total weight of the polyolefin.

In another embodiment the propylene copolymer is a random copolymer, also known as an "RCP," comprising propylene and up to 20 mole % of ethylene or a $C_4$ to $C_{20}$ olefin, preferably up to 20 mole % ethylene or a $C_4$ to $C_{20}$ olefin, preferably from 1 to 10 mole % ethylene or a $C_4$ to $C_{20}$ olefin.

In another embodiment, the polyolefin may be an impact copolymer (ICP) or block copolymer. Preferably, the impact copolymer is a polypropylene blend, as defined for the purposes of this invention. Propylene impact copolymers are commonly used in a variety of applications where strength and impact resistance are desired such as molded and extruded automobile parts, household appliances, luggage and furniture.

A typical propylene impact copolymer contains at least two phases or components, e.g., a thermoplastic (such as a propylene homopolymer) component and an elastomeric (such as a ethylene and/or propylene copolymer) component. The impact copolymer may also comprise three phases such as a PP/EP/PE combination with the PP continuous and a dispersed phase with EP outside and PE inside the dispersed phase particles. These components are usually produced in a sequential polymerization process wherein the thermoplastic (such as a propylene homopolymer) component produced in a first reactor is transferred to a second reactor where the elastomeric (such as a ethylene and/or propylene copolymer) component is produced and incorporated within the matrix of the thermoplastic component. The elastomeric component has rubbery characteristics and provides the desired impact resistance, whereas the thermoplastic component provides overall stiffness.

Another important feature of ICP's is the amount of amorphous polypropylene they contain. The ICP's of this invention are characterized as having low amorphous polypropylene, preferably less than 3% by weight, more preferably less than 2% by weight, even more preferably less than 1% by weight and most preferably there is no measurable amorphous polypropylene.

Preferred impact copolymers may be a reactor blend (in situ blend) or a post reactor (ex-situ) blend. In one embodiment, a suitable impact copolymer comprises from 40% to 95% by weight Component A (the thermoplastic component) and from 5% to 60% by weight Component B (the elastomeris component) based on the total weight of the impact copolymer; wherein Component A comprises propylene homopolymer or copolymer, the copolymer comprising 10% or less by weight ethylene, butene, hexene or octene comonomer; and wherein Component B comprises EP Rubber or propylene copolymer, wherein the copolymer comprises from 5% to 70% by weight ethylene, butene, hexene and/or octene comonomer, and from about 95% to about 30% by weight propylene. In one embodiment of the impact copolymer, Component B consists essentially of propylene and from about 30% to about 65% by weight ethylene. In another embodiment, Component B comprises ethylene-propylene copolymers, ethylene-propylene-diene terpolymers, ethylene-acrylate copolymers, ethylene-vinyl acetate, styrene-butadiene copolymers, ethylene-acrylic ester copolymers, polybutadiene, polyisoprene, natural rubber, isobutylene, hydrocarbon resin (the hydrocarbon resin being characterized by a molecular weight less than 5000, a $T_g$ of about 50 to 100° C. and a softening point, Ring and Ball, as measured by ASTM E 28, of less than about 140° C.), rosin ester, and mixtures thereof. In another embodiment, Component B has a molecular weight distribution of less than 3.5. In yet another embodiment, Component B has a weight average molecular weight of at least 20,000. A useful impact copolymer is disclosed in, for example, U.S. Pat. Nos. 6,342,566 and 6,384, 142. In another embodiment, Component B is a polyolefin having a heat of fusion of 70 J/g or less, preferably 50 J/g or less, alternately 40 J/g or less.

Component B is most preferably a copolymer consisting essentially of propylene and ethylene although other propylene copolymers, ethylene copolymers or terpolymers may be suitable depending on the particular product properties desired. For example, propylene/butene, hexene or octene copolymers, and ethylene/butene, hexene or octene copolymers may be used, and propylene/ethylene/hexene-1 terpolymers may be used. In a preferred embodiment though, Component B is a copolymer comprising at least 40% by weight propylene, more preferably from about 80% by weight to about 30% by weight propylene, even more preferably from about 70% by weight to about 35% by weight propylene. The comonomer content of Component B is preferably in the range of from about 20% to about 70% by weight comonomer, more preferably from about 30% to about 65% by weight comonomer, even more preferably from about 35% to about 60% by weight comonomer. Most preferably Component B consists essentially of propylene and from about 20% to about 70% ethylene, more preferably from about 30% to about 65% ethylene, and most preferably from about 35% to about 60% ethylene.

For other Component B copolymers, the comonomer contents will need to be adjusted depending on the specific properties desired. For example, for ethylene/hexene copolymers, Component B should contain at least 17% by weight hexene and at least 83% by weight ethylene.

Component B, preferably has a narrow molecular weight distribution Mw/Mn ("MWD"), i.e., lower than 5.0, preferably lower than 4.0, more preferably lower than 3.5, even more preferably lower than 3.0 and most preferably 2.5 or lower. These molecular weight distributions should be obtained in the absence of visbreaking or peroxide or other post reactor treatment molecular weight tailoring. Component B preferably has a weight average molecular weight (Mw as determined by GPC) of at least 100,000, preferably at least 150,000, and most preferably at least 200,000.

Component B preferably has an intrinsic viscosity greater than 1.00 dl/g, more preferably greater than 1.50 dl/g and most preferably greater than 2.00 dl/g. The term "intrinsic viscosity" or "IV" is used conventionally herein to mean the viscosity of a solution of polymer such as Component B in a given solvent at a given temperature, when the polymer composition is at infinite dilution. According to the ASTM standard test method D 1601-78, IV measurement involves a standard capillary viscosity measuring device, in which the viscosity of a series of concentrations of the polymer in the solvent at the given temperature are determined. For Component B, decalin is a suitable solvent and a typical temperature is 135° C. From the values of the viscosity of solutions of varying concentrations, the "value" at infinite dilution can be determined by extrapolation.

Component B preferably has a composition distribution breadth index (CDBI) of greater than 60%, more preferably greater than 65%, even more preferably greater than 70%, even more preferably greater than 75%, still more preferably greater than 80%, and most preferably greater than 85%. CDBI characterizes the compositional variation among polymer chains in terms of ethylene (or other comonomer) content of the copolymer as a whole. The CDBI is defined in U.S. Pat. No. 5,382,630, which is hereby incorporate by reference, as the weight percent of the copolymer molecules having a comonomer content within 50% of the median total molar comonomer content. The CDBI of a copolymer is readily determined utilizing well known techniques for isolating individual fractions of a sample of the copolymer. One such technique is Temperature Rising Elution Fraction (TREF), as described in Wild, et al., *J. Poly. Sci., Poly. Phys. Ed.*, vol. 20, p. 441 (1982) and U.S. Pat. No. 5,008,204, which are incorporated herein by reference.

Component B of the ICP's preferably has low crystallinity, preferably less than 10% by weight of a crystalline portion, more preferably less than 5% by weight of a crystalline portion. Where there is a crystalline portion of Component B, its composition is preferably the same as or at least similar to (within 15% by weight) the remainder of Component B in terms of overall comonomer weight percent.

The preferred melt flow rate ("MFR") of these ICP's depends on the desired end use but is typically in the range of from about 0.2 dg/min to about 200 dg/min, more preferably from about 5 dg/min to about 100 dg/min. Significantly, high MFRs, i.e., higher than 50 dg/min are obtainable. The ICP preferably has a peak melting point (Tm) of at least 145° C., preferably at least 150° C., more preferably at least 152° C., and most preferably at least 155° C.

The ICP's typically comprise from about 40% to about 95% by weight Component A and from about 5% to about 60% by weight Component B, preferably from about 50% to about 95% by weight Component A and from about 5% to about 50% Component B, even more preferably from about 60% to about 90% by weight Component A and from about 10% to about 40% by weight Component B. In the most preferred embodiment, the ICP consists essentially of Components A and B. The overall comonomer (preferably ethylene) content of the total ICP is preferably in the range of from about 2% to about 30% by weight, preferably from about 5% to about 25% by weight, even more preferably from about 5% to about 20% by weight, still more preferably from about 5% to about 15% by weight comonomer.

In another embodiment a preferred impact copolymer composition is prepared by selecting Component A and Component B such that their refractive indices (as measured by ASTM D 542-00) are within 20% of each other, preferably within 15%, preferably 10, even more preferably within 5% of each other. This selection produces impact copolymers with outstanding clarity. In another embodiment a preferred impact copolymer composition is prepared by selecting a blend of Component A and an NFP and a blend of Component B and an NFP such that refractive indices of the blends (as measured by ASTM D 542-00) are within 20% of each other, preferably within 15%, preferably 10, even more preferably within 5% of each other.

In yet another embodiment, the Gardner impact strength, tested on 0.125 inch disk at −29° C., of the propylene impact copolymer ranges from 20 in-lb to 1000 in-lb, and from 30 in-lb to 500 in-lb in another embodiment, and from 40 in-lb to 400 in-lb in yet another embodiment. Further, the 1% secant flexural modulus of the propylene impact copolymer may range from 100 MPa to 2300 MPa in one embodiment, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) of desirable propylene impact copolymers range from 0.1 dg/min to 2500 dg/min in one embodiment, and from 0.3 to 500 dg/min in another embodiment.

In yet another embodiment, the 1% secant flexural modulus of the polyolefin (ASTM D790A) is preferably 5 MPa or more, preferably 10 MPa or more, preferably 20 MPa or more, preferably 50 MPa or more, preferably 75 MPa or more, preferably 100 MPa or more, preferably 25 to 2500 MPa, preferably 100 to 2000 MPa, preferably 100 to 1800 MPa, preferably 200 to 1600 MPa, preferably 300 to 1400 MPa, preferably 400 to 1200 MPa, preferably 500 to 1000 MPa, wherein a desirable range may be any combination of any upper flexural modulus limit with any lower flexural modulus limit described herein.

In yet another embodiment, the 1% secant flexural modulus of the plasticized composition (ASTM D790A) is preferably 5 MPa or more, preferably 10 MPa or more, preferably 20 MPa or more, preferably 50 MPa or more, preferably 75 MPa or more, preferably 100 MPa or more, preferably 25 to 2500 MPa, preferably 100 to 2000 MPa, preferably 100 to 1800 MPa, preferably 200 to 1600 MPa, preferably 300 to 1400 MPa, preferably 400 to 1200 MPa, preferably 500 to 1000 MPa, wherein a desirable range may be any combination of any upper MPa limit with any lower MPa limit described herein.

Another suitable polyolefin comprises a blend of a polypropylene with a plastomer. The plastomers that are useful in the present invention may be described as polyolefin copolymers having a density of from 0.85 to 0.91 g/cm$^3$ (ASTM D1505) and a melt index (MI) between 0.10 and 30 dg/min (ASTM D 1238; 190° C., 2.16 kg). In one embodiment, the useful plastomer is a copolymer of ethylene derived units and at least one of $C_3$ to $C_{10}$ α-olefin derived units. The amount of comonomer ($C_3$ to $C_{10}$ α-olefin derived units) present in the plastomer ranges from 2 wt % to 35 wt % in one embodiment, and from 5 wt % to 30 wt % in another embodiment, and from 15 wt % to 25 wt % in yet another embodiment, and from 20 wt % to 30 wt % in yet another embodiment.

Plastomers useful in the invention typically have a weight-average molecular weight of 20 to 800 kg/mol in one embodiment, and from 30 to 700 kg/mol in another embodiment. The molecular weight distribution (Mw/Mn) of desirable plastomers ranges from 1.5 to 5. The 1% secant flexural modulus (ASTM D 790) of useful plastomers ranges from 10 to 150 MPa in one embodiment, and from 20 to 100 MPa in another embodiment. Further, the plastomer that is useful in compositions of the present invention has a melting temperature ($T_m$) of from 30 to 80° C. (first melt peak) and from 50 to 125° C. (second melt peak) in one embodiment, and from 40 to 70° C. (first melt peak) and from 50 to 100° C. (second melt peak) in another embodiment. Preferred plastomers are metallocene catalyzed copolymers of ethylene and higher α-olefins such as propylene, 1-butene, 1-hexene and 1-octene, such as those commercially available under the EXACT™ tradename from ExxonMobil Chemical Company (Houston, Tex.).

In another embodiment polyolefins that are useful in this invention include homopolymers and random copolymers of propylene having a heat of fusion as determined by Differential Scanning Calorimetry (DSC) of less than 50 J/g, and contains stereoregular propylene crystallinity preferably isotactic stereoregular propylene crystallinity. In another embodiment the polymer is a random copolymer of propylene and at least one comonomer selected from ethylene, $C_4$-$C_{12}$ α-olefins, and combinations thereof. Preferably the random copolymers of propylene comprises from 2 wt % to 25 wt % polymerized ethylene units, based on the total weight of the polymer; has a narrow composition distribution; has a melting point ($T_m$) of from 25° C. to 120° C., or from 35° C. to 80° C.; has a heat of fusion within the range having an upper limit of 50 J/g or 25 J/g and a lower limit of 1 J/g or 3 J/g; has a molecular weight distribution Mw/Mn of from 1.8 to 4.5; and has a melt index (MI) of less than 20 dg/min, or less than 15 dg/min. The intermolecular composition distribution of the copolymer is determined by thermal fractionation in a solvent. A typical solvent is a saturated hydrocarbon such as hexane or heptane. The thermal fractionation procedure is described below. Typically, approximately 75% by weight, preferably 85% by weight, of the copolymer is isolated as one or two adjacent, soluble fractions with the balance of the copolymer in immediately preceding or succeeding fractions. Each of these fractions has a composition (wt % comonomer such as ethylene or other α-olefin) with a difference of no greater than 20% (relative), preferably 10% (relative), of the average wt % comonomer of the copolymer. The copolymer has a narrow composition distribution if it meets the fractionation test described above.

A particularly preferred polymer useful in the present invention is an elastic polymer with a moderate level of crystallinity due to stereoregular propylene sequences. The polymer can be: (A) a propylene homopolymer in which the stereoregularity is disrupted in some manner such as by regio-inversions; (B) a random propylene copolymer in which the propylene stereoregularity is disrupted at least in part by comonomers; or (C) a combination of (A) and (B).

In one embodiment, the polymer further includes a non-conjugated diene monomer to aid in vulcanization and other chemical modification of the blend composition. The amount of diene present in the polymer is preferably less than 10% by weight, and more preferably less than 5% by weight. The diene may be any non-conjugated diene which is commonly used for the vulcanization of ethylene propylene rubbers including, but not limited to, ethylidene norbornene, vinyl norbornene, and dicyclopentadiene.

In one embodiment, the polymer is a random copolymer of propylene and at least one comonomer selected from ethylene, $C_4$-$C_{12}$ α-olefins, and combinations thereof. In a particular aspect of this embodiment, the copolymer includes ethylene-derived units in an amount ranging from a lower limit of 2%, 5%, 6%, 8%, or 10% by weight to an upper limit of 20%, 25%, or 28% by weight. This embodiment will also include propylene-derived units present in the copolymer in an amount ranging from a lower limit of 72%, 75%, or 80% by weight to an upper limit of 98%, 95%, 94%, 92%, or 90% by weight. These percentages by weight are based on the total weight of the propylene and ethylene-derived units; i.e., based on the sum of weight percent propylene-derived units and weight percent ethylene-derived units being 100%.

Comonomer content of discrete molecular weight ranges can be measured by Fourier Transform Infrared Spectroscopy (FTIR) in conjunction with samples collected by GPC. One such method is described in Wheeler and Willis, Applied Spectroscopy, 1993, vol. 47, pp. 1128-1130.

The crystallinity of the polymers may be expressed in terms of heat of fusion. Embodiments of the present invention include polyolefins having a heat of fusion, as determined by DSC, ranging from 1 to 50 J/g, preferably 3 to 30 J/g, more preferably 5 to 20 J/g. The crystallinity of the polymer may also be expressed in terms of crystallinity percent. The thermal energy for the highest order of polypropylene is estimated at 207 J/g. That is, 100% crystallinity is equal to 207 J/g. Preferably, the polymer has a polypropylene crystallinity within the range having an upper limit of 65%, 40%, 30%, 25%, or 20%, and a lower limit of 1%, 3%, 5%, 7%, or 8%.

The level of crystallinity is also reflected in the melting point. The term "melting point," as used herein, is the highest peak. "Highest" meaning the largest amount of polymer being reflected as opposed to the peak occurring at the highest temperature among principal and secondary melting peaks as determined by DSC, discussed above. In one embodiment of the present invention, the polymer has a single melting point. Typically, a sample of propylene copolymer will show secondary melting peaks adjacent to the principal peak, which are considered together as a single melting point. The highest of these peaks is considered the melting point. The polymer preferably has a melting point by DSC ranging from an upper limit of 110° C., 105° C., 90° C., 80° C., or 70° C., to a lower limit of 0° C., 20° C., 25° C., 30° C., 35° C., 40° C., or 45° C.

Preferred propylene polymers used in the invention have a weight average molecular weight ($M_w$) within the range having an upper limit of 5,000,000 g/mol, 1,000,000 g/mol, or 500,000 g/mol, and a lower limit of 10,000 g/mol, 20,000 g/mol, or 80,000 g/mol, and a molecular weight distribution $M_w/M_n$ (MWD), sometimes referred to as a "polydispersity index" (PDI), ranging from a lower limit of 1.5, 1.8, or 2.0 to an upper limit of 40, 20, 10, 5, or 4.5. In one embodiment, the polymer has a Mooney viscosity, ML(1+4) @ 125° C., of 100 or less, 75 or less, 60 or less, or 30 or less. Mooney viscosity, as used herein, can be measured as ML(1+4) @ 125° C. according to ASTM D1646, unless otherwise specified.

Preferred random propylene polymers used in embodiments of the present invention have a ratio of m to r (m/r) of more than 1. The propylene tacticity index, expressed herein as "m/r", is determined by 13C nuclear magnetic resonance (NMR). The propylene tacticity index m/r is calculated as defined in H. N. Cheng, *Macromolecules*, 17, 1950 (1984). The designation "m" or "r" describes the stereochemistry of pairs of contiguous propylene groups, "m" referring to meso and "r" to racemic. An m/r ratio of 0 to less than 1.0 generally describes a syndiotactic polymer, and an m/r ratio of 1.0 an atactic material, and an m/r ratio of greater than 1.0 an isotactic material. An isotactic material theoretically may have a ratio approaching infinity, and many by-product atactic polymers have sufficient isotactic content to result in ratios of greater than 50.

In a preferred embodiment, the preferred random propylene polymer have isotactic stereoregular propylene crystallinity. The term "stereoregular" as used herein means that the predominant number, i.e. greater than 80%, of the propylene residues in the polypropylene exclusive of any other monomer such as ethylene, has the same 1,2 insertion and the stereochemical orientation of the pendant methyl groups is the same, either meso or racemic.

Preferred random propylene polymer useful in this invention have an mm triad tacticity index of three propylene units, as measured by $^{13}C$ NMR, of 75% or greater, 80% or greater, 82% or greater, 85% or greater, or 90% or greater. The mm triad tacticity index of a polymer is the relative tacticity of a sequence of three adjacent propylene units, a chain consisting of head to tail bonds, expressed as a binary combination of m and r sequences. It is usually expressed for semi-amorphous copolymers of the present invention as the ratio of the number of units of the specified tacticity to all of the propylene triads in the copolymer. The mm triad tacticity index (mm fraction) of a propylene copolymer can be determined from a $^{13}C$ NMR spectrum of the propylene copolymer and the following formula:

$$\text{mm Fraction} = \frac{PPP(mm)}{PPP(mm) + PPP(mr) + PPP(rr)}$$

where PPP(mm), PPP(mr) and PPP(rr) denote peak areas derived from the methyl groups of the second units in the following three propylene unit chains consisting of head-to-tail bonds:

PPP(mm):

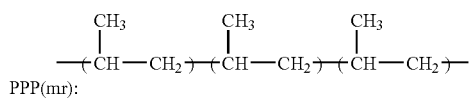

PPP(mr):

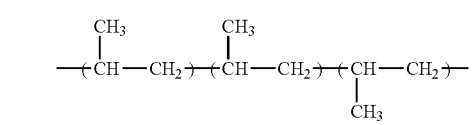

PPP(rr):

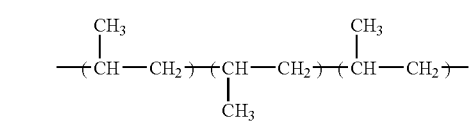

The $^{13}$C NMR spectrum of the propylene copolymer is measured as described in U.S. Pat. Nos. 5,504,172 and 6,642,316 (column 6, line 38 to column 9, line 18). The spectrum relating to the methyl carbon region (19-23 parts per million (ppm)) can be divided into a first region (21.2-21.9 ppm), a second region (20.3-21.0 ppm) and a third region (19.5-20.3 ppm). Each peak in the spectrum was assigned with reference to an article in the journal *Polymer*, Volume 30 (1989), page 1350 or an article in the journal *Macromolecules*, 17, (1984), 1950 (In the event of a conflict between the Polymer article and the Macromolecules article, the Polymer article shall control). In the first region, the methyl group of the second unit in the three propylene unit chain represented by PPP (mm) resonates. In the second region, the methyl group of the second unit in the three propylene unit chain represented by PPP (mr) resonates, and the methyl group (PPE-methyl group) of a propylene unit whose adjacent units are a propylene unit and an ethylene unit resonates (in the vicinity of 20.7 ppm). In the third region, the methyl group of the second unit in the three propylene unit chain represented by PPP (rr) resonates, and the methyl group (EPE-methyl group) of a propylene unit whose adjacent units are ethylene units resonates (in the vicinity of 19.8 ppm). The calculation of the triad tacticity is outlined in the techniques shown in U.S. Pat. No. 5,504,172. Subtraction of the peak areas for the error in propylene insertions (both 2,1 and 1,3) from peak areas from the total peak areas of the second region and the third region, the peak areas based on the 3 propylene units-chains (PPP (mr) and PPP(rr)) consisting of head-to-tail bonds can be obtained. Thus, the peak areas of PPP(mm), PPP(mr) and PPP(rr) can be evaluated, and hence the mm triad tacticity of the propylene unit chain consisting of head-to-tail bonds can be determined.

For further information on how the mm triad tacticity can be determined from a $^{13}$C-NMR spectrum of the polymer, as described by J. A. Ewen, "Catalytic Polymerization of Olefins", (the Ewen method); and Eds. T. Keii, K. Soga; Kodanska Elsevier Pub.; Tokyo, 1986, P 271, and as described in detail in U.S. Patent Application US2004/054086 filed Mar. 18, 2004 on page 8, in numbered paragraphs [0046] to [0054], all of which are incorporated by reference herein.

In another embodiment polymers that are useful in this invention as random propylene polymers include homopolymers and random copolymers of propylene having a heat of fusion as determined by Differential Scanning Calorimetry (DSC) of less than 70 J/g, an MFR of 50 dg/min or less, and contain stereoregular propylene crystallinity preferably isotactic stereoregular propylene crystallinity. In another embodiment the polymer is a random copolymer of propylene and at least one comonomer selected from ethylene, $C_4$-$C_{12}$ α-olefins, and combinations thereof. Preferably the random copolymers of propylene comprises from 10 wt % to 25 wt % polymerized ethylene units, based on the total weight of the polymer; has a narrow intermolecular composition distribution (e.g. 75% or more); has a melting point (Tm) of from 25° C. to 120° C., or from 35° C. to 80° C.; has a heat of fusion within the range having an upper limit of 70 J/g or 25 J/g and a lower limit of 1 J/g or 3 J/g; has a molecular weight distribution Mw/Mn of from 1.8 to 4.5; and has a melt flow rate of less than 40 dg/min, or less than 20 dg/min (as measured at 230° C., and 2.16 kg, ASTM D-1238).

In embodiments of the present invention, a preferred propylene polymer has a melt index (MI) of 20 dg/min or less, 7 dg/min or less, 5 dg/min or less, or 2 dg/min or less, or less than 2 dg/min. The determination of the MI of the polymer is according to ASTM D1238 (190° C., 2.16 kg). In this version of the method a portion of the sample extruded during the test was collected and weighed. This is commonly referred to as the modification 1 of the experimental procedure. The sample analysis is conducted at 190° C. with a 1 minute preheat on the sample to provide a steady temperature for the duration of the experiment.

In one embodiment, the polymer used in the present invention is described in detail as the "Second Polymer Component (SPC)" in WO 00/69963, WO 00/01766, WO 99/07788, WO 02/083753, and described in further detail as the "Propylene Olefin Copolymer" in WO 00/01745, all of which are fully incorporated by reference herein for purposes of U.S. patent practice.

In a preferred embodiment, the polypropylene and polypropylene blends useful in this invention have a peak melting point of at least 140° C. (preferably at least 145° C., preferably at least 150° C., preferably at least 155° C., preferably at least 160° C., preferably at least 165° C.) and a heat of fusion of at least 70 J/g (preferably at least 75 J/g, preferably at least 80 J/g, preferably at least 85 J/g, preferably at least 90 J/g, preferably at least 95 J/g, preferably at least 100 J/g), as determined by Differential Scanning Calorimetry (DSC) preferably on the second melt scan.

In another embodiment, the polymers described in WO 03/040201, WO 03/040095, WO 03/040202, WO 03/040233 and WO 03/040442, can be used as the polyolefin herein.

Ethylene Polymer and Blends

In another aspect of the invention, the polyolefin is selected from polyethylene (ethylene homopolymer and copolymers) and blends thereof. Useful copolymers comprise one or more comonomers in addition to ethylene and can be a random copolymer, a statistical copolymer, a block copolymer, and/or blends thereof. In particular, the ethylene polymer blends described herein may be physical blends or in situ blends of more than one type of ethylene polymer or blends of ethylene polymers with polymers other than ethylene polymers where the ethylene polymer component is the majority component (e.g. greater than 50 wt %). The method of making the polyethylene is not critical, as it can be made by slurry, solution, gas phase, high pressure or other suitable processes, and by using catalyst systems appropriate for the polymerization of polyethylenes, such as Ziegler-Natta-type catalysts, chromium catalysts, metallocene-type catalysts, other appropriate catalyst systems or combinations thereof, or by free-radical polymerization. In a preferred embodiment the ethylene polymers are made by the catalysts, activators and processes described in U.S. Pat. Nos. 6,342,566, 6,384,142, WO 03/040201, WO 97/19991 and U.S. Pat. No. 5,741,563. Such catalysts are well known in the art, and are described in, for example, ZIEGLER CATALYSTS (Gerhard Fink, Rolf Mülhaupt and Hans H. Brintzinger, eds., Springer-Verlag 1995); Resconi et al.; and I, II METALLOCENE-BASED POLYOLEFINS (Wiley & Sons 2000).

Preferred ethylene polymers and copolymers that are useful in this invention include those sold by ExxonMobil Chemical Company in Houston Tex., including those sold as ExxonMobil HDPE, ExxonMobil LLDPE, and ExxonMobil LDPE; and those sold under the EXACT™, EXCEED™, ESCORENE™, ESCOR™, ENABLE™, NTX™, PAXON™, and OPTEMA™ tradenames.

The polyethylene may be an ethylene homopolymer, such as HDPE. In another embodiment the ethylene homopolymer has a molecular weight distribution ($M_w/M_n$) of up to 40, preferably ranging from 1.5 to 20, and from 1.8 to 10 in another embodiment, and from 1.9 to 5 in yet another embodiment, and from 2.0 to 4 in yet another embodiment. In another embodiment, the 1% secant flexural modulus falls in a range of 200 to 1000 MPa, and from 300 to 800 MPa in another embodiment, and from 400 to 750 MPa in yet another embodiment, wherein a desirable polymer may exhibit any combination of any upper flexural modulus limit with any lower flexural modulus limit. The melt index (MI) of preferred ethylene homopolymers range from 0.05 to 800 dg/min in one embodiment, and from 0.1 to 100 dg/min in another embodiment, as measured according to ASTM D1238 (190° C., 2.16 kg).

In another embodiment of the invention, the ethylene polymer is an ethylene copolymer, either random, or block, of ethylene and one or more comonomers selected from $C_3$ to $C_{20}$ α-olefins, typically from $C_3$ to $C_{10}$ α-olefins in another embodiment. Preferably the comonomers are present from 0.1 wt % to 50 wt % of the copolymer in one embodiment, and from 0.5 to 30 wt % in another embodiment, and from 1 to 15 wt % in yet another embodiment, and from 0.1 to 5 wt % in yet another embodiment, wherein a desirable copolymer comprises ethylene and $C_3$ to $C_{20}$ α-olefin derived units in any combination of any upper wt % limit with any lower wt % limit described herein. Preferably the ethylene copolymer will have a weight average molecular weight of from greater than 8,000 g/mole in one embodiment, and greater than 10,000 g/mole in another embodiment, and greater than 12,000 g/mole in yet another embodiment, and greater than 20,000 g/mole in yet another embodiment, and less than 1,000,000 g/mole in yet another embodiment, and less than 800,000 g/mole in yet another embodiment, wherein a desirable copolymer may comprise any upper molecular weight limit with any lower molecular weight limit described herein.

In another embodiment the ethylene copolymer comprises ethylene and one or more other comonomers selected from the group consisting of $C_3$ to $C_{20}$ linear, branched or cyclic monomers; preferably $C_3$ to $C_{12}$ linear or branched alpha-olefins; preferably propylene, 1-butene, 1-pentene, 1-hexene, 1-heptene, 1-octene, 1-nonene, 1-decene, 1-dodecene, 4-methyl-1-pentene, 3-methyl-1-pentene, 3,5,5-trimethyl-1-hexene, and 5-ethyl-1-nonene. In a preferred embodiment, the comonomer is selected from propylene, 1-butene, 1-hexene, and 1-octene. Comonomers may be present at up to 50 wt %, preferably from 0 to 40 wt %, more preferably from 0.5 to 30 wt %, more preferably from 2 to 30 wt %, more preferably from 5 to 20 wt %.

In a particularly desirable embodiment, the ethylene polymer used herein is a plastomer having a density of 0.91 g/cm³ or less, as determined by ASTM D1505, and a melt index (MI) between 0.1 and 50 dg/min, as determined by ASTM D1238 (190° C., 2.16 kg). In one embodiment, the useful plastomer is a copolymer of ethylene and at least one $C_3$ to $C_{12}$ α-olefin, preferably $C_4$ to $C_8$ α-olefins. The amount of $C_3$ to $C_{12}$ α-olefin present in the plastomer ranges from 2 wt % to 35 wt % in one embodiment, and from 5 wt % to 30 wt % in another embodiment, and from 15 wt % to 25 wt % in yet another embodiment, and from 20 wt % to 30 wt % in yet another embodiment.

Preferred plastomers useful in the invention have a melt index of between 0.1 and 40 dg/min in one embodiment, and from 0.2 to 20 dg/min in another embodiment, and from 0.5 to 10 dg/min in yet another embodiment. The average molecular weight of preferred plastomers ranges from 10,000 to 800,000 g/mole in one embodiment, and from 20,000 to 700,000 g/mole in another embodiment. The 1% secant flexural modulus (ASTM D790) of preferred plastomers ranges from 5 to 100 MPa in one embodiment, and from 10 MPa to 50 MPa in another embodiment. Further, preferred plastomers that are useful in compositions of the present invention have a melting temperature ($T_m$, first melt peak) of from 30 to 100° C. in one embodiment, and from 40 to 80° C. in another embodiment. The degree of crystallinity of preferred plastomers is between 3 and 30%.

Particularly preferred plastomers useful in the present invention are synthesized using a single-site catalyst, such as a metallocene catalyst, and comprise copolymers of ethylene and higher α-olefins such as propylene, 1-butene, 1-hexene and 1-octene, and which contain enough of one or more of these comonomer units to yield a density between 0.86 and 0.91 g/cm³ in one embodiment. The molecular weight distribution ($M_w/M_n$) of desirable plastomers ranges from 1.5 to 5 in one embodiment, and from 2.0 to 4 in another embodiment. Examples of a commercially available plastomers are EXACT™ 4150, a copolymer of ethylene and 1-hexene, the 1-hexene derived units making up from 18 to 22 wt % of the plastomer and having a density of 0.895 g/cm³ and MI of 3.5 dg/min (ExxonMobil Chemical Company, Houston, Tex.); and EXACT™ 8201, a copolymer of ethylene and 1-octene, the 1-octene derived units making up from 26 to 30 wt % of the plastomer, and having a density of 0.882 g/cm³ and MI of 1.0 dg/min (ExxonMobil Chemical Company, Houston, Tex.).

In a preferred embodiment of the present invention, the ethylene polymers have a weight average molecular weight ($M_w$) within the range having an upper limit of 5,000,000 g/mole, 1,000,000 g/mole, or 500,000 g/mole, and a lower limit of 10,000 g/mole, 20,000 g/mole, or 80,000 g/mole.

Preferred ethylene polymers for the present invention have a molecular weight distribution ($M_w/M_n$) ranging from 1.5 to 20, and from 1.6 to 15 in another embodiment, and from 1.7 to 10 in yet another embodiment, and from 1.8 to 5 in yet another embodiment, and from a lower limit of 1.5, 1.8, or 2.0 to an upper limit of 40, 20, 10, 5, or 4.5 in yet another embodiment.

The melt index (MI) of preferred ethylene polymers, as measured according to ASTM D1238 (190° C., 2.16 kg), ranges from 0.02 dg/min to 800 dg/min in one embodiment, from 0.05 to 500 dg/min in another embodiment, and from 0.1 to 100 dg/min in another embodiment. In another embodiment of the present invention, the polyethylene has a MI of 20 dg/min or less, 7 dg/min or less, 5 dg/min or less, or 2 dg/min or less, or less than 2 dg/min. In yet another embodiment, the polymer has a Mooney viscosity, ML(1+4) @ 125° C. (measured according to ASTM D1646) of 100 or less, 75 or less, 60 or less, or 30 or less.

In yet another embodiment, the 1% secant flexural modulus of preferred ethylene polymers ranges from 5 to 1000

MPa, and from 10 to 800 MPa in another embodiment, and from 5 to 200 MPa in yet another embodiment, wherein a desirable polymer may exhibit any combination of any upper flexural modulus limit with any lower flexural modulus limit.

The crystallinity of preferred ethylene polymers useful herein may be expressed in terms of heat of fusion. Embodiments of the present invention include polymers having a heat of fusion, as determined by DSC, ranging from a lower limit of 0.1 J/g, or preferably 1.0 J/g, to an upper limit of 260 J/g, or preferably 240 J/g.

The crystallinity of the polymer may also be expressed in terms of crystallinity percent. The thermal energy for the highest order of polyethylene is estimated at 290 J/g. That is, 100% crystallinity is equal to 290 J/g. Preferably, the polymer has a crystallinity within the range having an upper limit of 80%, 60%, 40%, 30%, or 20%, and a lower limit of 1%, 3%, 5%, 8%, or 10%.

The level of crystallinity may be reflected in the melting point. In one embodiment of the present invention, the ethylene polymer has a single melting point. Typically, a sample of ethylene copolymer will show secondary melting peaks adjacent to the principal peak, which are considered together as a single melting point. The highest of these peaks is considered the melting point. The polymer preferably has a melting point by DSC ranging from an upper limit of 150° C., 130° C., 100° C., 80° C., or 60° C., to a lower limit of 0° C., 20° C., 25° C., 30° C., 35° C., 40° C., or 45° C.

Butene Polymers and Blends

In another aspect of the invention, the polyolefin is selected from polybutene (1-butene homopolymers and copolymers) and blends thereof. The homopolymer may be atactic, isotactic, or syndiotactic polybutene, and blends thereof. The copolymer can be a random copolymer, a statistical copolymer, a block copolymer, and blends thereof. In particular, the inventive polymer blends described herein include impact copolymers, elastomers and plastomers, any of which may be physical blends or in situ blends with the polybutene. The method of making the polybutene is not critical, as it can be made by slurry, solution, gas phase or other suitable processes, and by using catalyst systems appropriate for the polymerization of polyolefins, such as Ziegler-Natta-type catalysts, metallocene-type catalysts, other appropriate catalyst systems or combinations thereof. Preferred linear alpha-olefins useful as comonomers for the butene copolymers useful in this invention include ethylene and $C_3$ to $C_8$ alpha-olefins, more preferably ethylene, propylene, 1-hexene, and 1-octene. Preferred polybutene polymers are poly(1-butene) polymers and copolymers. Preferred poly(1-butene) polymers are made using a metallocene catalyst in a solution process. Preferred comonomers are ethylene and propylene. Poly(1-butene) homopolymers and 1-butene/ethylene copolymers are commercially available from Basell Polyolefins.

In one embodiment, the Gardner impact strength of the butene polymer ranges from 20 to 1000 in-lb (preferably 30 to 500 in-lb, preferably 40 to 400 in-lb) when tested on 0.125 inch disk at 23° C. Further, the butene polymer may possess a 1% secant flexural modulus ranging from 100 to 2300 MPa (preferably 200 to 2100 MPa, preferably 300 to 2000 MPa). The melt flow rate (MFR; 230° C., 2.16 kg) of desirable butene polymers ranges from 0.1 to 500 dg/min.

Nucleating Agent

The composition described herein comprising NFP and at least one polyolefin will also include the addition of at least one nucleating. Typically, nucleating agents increase the rate of crystallization (isothermal and/or non-isothermal) of the polyolefin. A special class of nucleating agents known as clarifying agents typically reduces the size of crystallites, thereby improving the transparency and clarity of articles made from the polyolefin.

Suitable nucleating agents for use herein are disclosed in *Plastics Additive Handbook*, $5^{th}$ *Ed*.; H. Zweifel, Ed.; Hanser-Gardner Publications, (2001); Chapter 18, p. 949-972. Suitable nucleating agents for use herein are also disclosed by H. N. Beck in *Heterogeneous Nucleating Agents for Polypropylene Crystallization*, J. APPLIED POLY. SCI. Vol. 11, p. 673-685 (1967) and in *Heterogeneous Nucleation Studies on Polypropylene*, J. POLY. SCI.: POLY. LETTERS, Vol. 21, p. 347-351 (1983). Nucleating agents have been shown to be useful in a variety of thermoplastic polyolefins, including for example, homopolypropylene (hPP), isotactic polypropylene (iPP), syndiotactitc polypropylene (sPP), random copolymer polypropylene (RCP), impact copolymer polypropylene (ICP), block or segmented polypropylene, blends of polypropylene with other synthetic polymers, polypropylene prepared by a Ziegler-Natta catalyst, and polypropylene prepared by a metallocene or other single-site catalyst.

Useful nucleating agents can be either homogeneous nucleating agents (i.e., melt-soluble, meaning dissolved into the polyolefin) and heterogeneous nucleating agents (i.e., melt-insoluble, meaning suspended or dispersed in the polyolefin). Typical nucleating agents promote at least one crystal polymorph for the polyolefin. For example, when the polyolefin is isotactic polypropylene (iPP), known crystal forms include the so-called alpha, beta, and gamma polymorphs; useful nucleating agents therefore include those that promote alpha crystals in iPP, those that promote beta crystals in iPP, and those that promote gamma crystals in iPP. Suitable nucleating agents also include those that promote crystallization in syndiotactic polypropylene (sPP). Suitable nucleating agents preferably improve one or more performance parameters of the polyolefin, such as increased clarity, reduced haze, increased stiffness, increased impact toughness, increased heat deflection temperature; and/or processing parameters, such as reduced cycle time or increased line speed. Suitable nucleating agents can be organic, inorganic, or polymeric, and may include combinations of one or more nucleating agent.

The following list is intended to be illustrative of suitable choices of nucleating agents for inclusion in the instant formulations. Suitable nucleating agents include fillers such as silica, kaolin, carbon black, and talc; metal salts including sodium salts, lithium salts, potassium salts, phosphonic acid salts, carboxylate salts, and aromatic carboxylic-acid salts (including norbornene carboxylic-acid salts); metal phosphates (including sodium phosphates), phosphate esters, and phosphate ester salts; metal salts of suberic acid (including the calcium salt); metal salts of hexahydrophthalic acid; salts of disproportionated rosin esters; sorbitol derivatives, including dibenzylidene sorbitol and derivatives, sorbitol acetal and derivatives, and sorbitol di-acetal and derivatives; quinacridone dyes; carboxamide derivatives, including naphthalene carboxamide derivatives; benzenetrisamide derivatives, including 1,3,5-benzenetrisamides described in Blomenhofer, et al, *Macromolecules* 2005, vol 38, p. 3688-3695; trimesic acid derivatives; and polymeric nucleating agents such as poly(3-methyl-1-butene), poly(dimethylstyrene), poly(ethylene terephthalate), polyamides (nylons), and polycarbonates.

Specific examples of suitable nucleating agents are sodium benzoate and sodium naphthenoate, sodium 2,2'-methylenebis(4,6-di-tert-butylphenyl)phosphate, aluminum 2,2'-methylenebis(4,6-di-tert-butylphenyl) phosphate, di(p- tolylidene)sorbitol, dibenzylidene sorbitol, di(p-methylbenzylidene)sorbitol, di(p-ethylbenzylidene)sorbitol, bis(3,4-dimethylbenzylidene)sorbitol, and N',N'-dicyclohexyl-2,6-naphthalenedicarboxamide. Other suitable nucleating agents are disclosed in U.S. Pat. Nos. 4,016,118; 4,371,645; 5,049,605; 6,235,823; US 2004/0132884; WO 02/046300; WO 03/102069; EP 776933.

Additional specific examples of suitable nucleating agents include: those available from Milliken Chemical under the "Millad" and "Hyperform" tradenames, including
- Millad 3905 [DBS, or 1,3:2,4-dibenzylidenesorbitol],
- Millad 3940 [MDBS, or 1,3:2,4-bis-(p-methylbenzylidene)sorbitol],
- Millad 3988 [DMDBS, or 1,3:2,4-bis(3,4-dimethylbenzylidene)sorbitol], and
- HPN-68 [2.2.1-heptane-bicyclodicarboxylic acid];

those available from Ciba Specialty Chemicals under the "Irgaclear" and "Irgastab" tradenames, including
- Irgaclear D [DBS, or 1,3:2,4-dibenzylidenesorbitol] and
- Irgaclear DM [MDBS, or 1,3:2,4-bis-(p-methylbenzylidene)sorbitol];

those available from Asahi Denka Kogyo and Amfine under the "ADKstab" and "NA" tradenames, including:
- NA-11 [2,2'-methylenebis(4,6-di-tertbutylphenol)phosphate salt] and
- NA-21 [2,2'-methylenebis(4,6-di-tertbutylphenol)phosphate aluminum complex];

those available from Mitsui Chemicals under the "NC" tradename, including
- NC-4 [EDBS, or 1,3:2,4-bis-(p-ethylbenzylidene)sorbitol];

those available from New Japan Chemical under the "NJSTAR", "NU", "Gel All", and "Geniset" tradenames, including
- NU100 [N,N'-dicyclohexyl-2,6-naphathalene dicarboxamide],
- NJSTAR [N,N'-dicyclohexyl-2,6-naphathalene diczroxamide],
- Gel All D [DBS, or 1,3:2,4-dibenzylidenesorbitol], and
- Gel All MD [MDBS, or 1,3:2,4-bis-(p-methylbenzylidene)sorbitol];

those available from EC Chemical (Japan) under the "EC" tradename, including
- EC-1 [(1,3:2,4)dimethyldibenylidene sorbitol] and
- EC-4 [a sorbitol].

Preferred nucleating agents include dibenzylidene sorbitol derivatives, phosphate ester derivatives, and benzenetrisamide derivatives. Particularly preferred nucleating agents include 1,3:2,4-bis(3,4-dimethylbenzylidene)sorbitol (available as Millad 3988 from Milliken Chemical; Spartanburg, S.C.), 2.2.1-heptane-bicyclodicarboxylic acid (available as HPN-68 from Milliken Chemical; Spartanburg, S.C.), 1,3:2,4-bis-(p-methylbenzylidene)sorbitol (available as Irgaclear DM from Ciba Specialty Chemicals; Basel, Switzerland), 2,2'-methylenebis(4,6-di-tertbutylphenol) phosphate salt (available as NA-11 from Amfine Chemical; Upper Saddle River, N.J.), and sodium benzoate (available from Ciba Specialty Chemicals; Basel, Switzerland).

The appearance and mechanical properties of thermoplastic polyolefin/NFP blends can be controlled by the type of nucleating agent and the NFP loading used. The nucleating agent(s) are typically present in the composition of this invention at 0.01 to 1 wt % (100 to 10,000 ppm), preferably 0.02 to 0.5 wt % (200 to 5,000 ppm), preferably 0.03 to 0.3 wt % (300 to 3,000 ppm), preferably 0.05 to 0.25 wt % (500 to 2,500 ppm), based upon the weight of the composition (where ppm is parts-per-million by weight).

Other Additives

The polyolefin compositions of the present invention may also include a slip agent. Preferred slip agents are preferably a fast bloom slip agent, and can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate. The slip agent(s) are typically present in the composition of this invention at 0.001 to 1 wt % (10 to 10,000 ppm), preferably 0.01 to 0.5 wt % (100 to 5,000 ppm), preferably 0.05 to 0.25 wt % (500 to 2,500 ppm), based upon the weight of the composition (where ppm is parts-per-million by weight).

In one embodiment the slip agent is an ionic compound. Ionic slip agents include salt derivatives of aromatic or aliphatic hydrocarbon oils, notably metal salts of fatty acids, including metal salts of carboxylic, sulfuric, and phosphoric aliphatic saturated or unsaturated acid having a chain length of 7 to 26 carbon atoms, preferably 10 to 22 carbon atoms. Examples of suitable fatty acids include the monocarboxylic acids lauric acid, stearic acid, succinic acid, stearyl lactic acid, lactic acid, phthalic acid, benzoic acid, hydroxystearic acid, ricinoleic acid, naphthenic acid, oleic acid, palmitic acid, erucic acid, and the like, and the corresponding sulfuric and phosphoric acids. Suitable metals include Li, Na, Mg, Ca, Sr, Ba, Zn, Cd, Al, Sn, Pb and so forth. Representative salts include, for example, magnesium stearate, calcium stearate, sodium stearate, zinc stearate, calcium oleate, zinc oleate, magnesium oleate and so on, and the corresponding metal higher alkyl sulfates and metal esters of higher alkyl phosphoric acids.

In another embodiment, the fatty acid metal salts are substantially absent from the polyolefin compositions of the present invention. By "substantially absent," it is meant that these compounds are not added deliberately to the compositions and, if present, are present at less than 1 wt %, more preferably less than 0.8 wt %, more preferably less than 0.5 wt %, more preferably less than 0.1 wt %, more preferably less than 0.05 wt %, more preferably less than 0.01 wt %, more preferably less than 0.001 wt %, based upon the weight of the polyolefin and the NFP.

In one embodiment the slip agent is a non-ionic functionalized compound. Suitable functionalized compounds include: (a) esters, amides, alcohols and acids of oils including aromatic or aliphatic hydrocarbon oils, for example, mineral oils, naphthenic oils, paraffinic oils; natural oils such as castor, corn, cottonseed, olive, rapeseed, soybean, sunflower, other vegetable and animal oils, and so on. Representative functionalized derivatives of these oils include, for example, polyol esters of monocarboxylic acids such as glycerol monostearate, pentaerythritol monooleate, and the like, saturated and unsaturated fatty acid amides or ethylenebis(amides), such as oleamide, erucamide, linoleamide, and mixtures thereof, glycols, polyether polyols like Carbowax, and adipic acid, sebacic acid, and the like; (b) waxes, such as carnauba wax, microcrystalline wax, polyolefin waxes, e.g. polyethylene waxes; (c) fluoro-containing polymers such as polytetrafluoroethylene, fluorine oils, fluorine waxes and so forth; and (d) silicon compounds such as silanes and silicone polymers, including silicone oils, polydimethylsiloxane, amino-modified polydimethylsiloxane, and so on.

The fatty amides useful as slip agents in the present invention are represented by the formula:

$$RC(O)NHR^1$$

where R is a saturated or unsaturated alkyl group having of from 7 to 26 carbon atoms, preferably 10 to 22 carbon atoms, and $R^1$ is independently hydrogen or a saturated or unsaturated alkyl group having from 7 to 26 carbon atoms, preferably 10 to 22 carbon atoms. Compounds according to this structure include for example, palmitamide, stearamide, arachidamide, behenamide, oleamide, erucamide, linoleamide, stearyl stearamide, palmityl palmitamide, stearyl arachidamide and mixtures thereof.

The ethylenebis(amides) useful as slip agents in the present invention are represented by the formula:

$$RC(O)NHCH_2CH_2NHC(O)R$$

where each R is independently is a saturated or unsaturated alkyl group having of from 7 to 26 carbon atoms, preferably 10 to 22 carbon atoms. Compounds according to this structure include for example, stearamidoethylstearamide, stearamidoethylpalmitamide, palmitamido-ethylstearamide, ethylenebisstearamide, ethylenebisoleamide, stearylerucamide, erucamidoethylerucamide, oleamidoethyloleamide, erucamidoethyloleamide, oleamidoethylerucamide, stearamidoethylerucamide, erucamidoethylpalmitamide, palmitamidoethyloleamide and mixtures thereof.

Commercially available examples of fatty amides useful as slip agents include Ampacet 10061 which comprises 5% of a 50:50 mixture of the primary amides of erucic and stearic acids in polyethylene; Elvax 3170 which comprises a similar blend of the amides of erucic and stearic acids in a blend of 18% vinyl acetate resin and 82% polyethylene. These slip agents are available from DuPont. Useful slip agents also are available from Croda Universal, Inc. (Houston, Tex.), including Crodamide OR (an oleamide), Crodamide SR (a stearamide), Crodamide ER (an erucamide), and Crodamide BR (a behenamide); and from Chemtura Corporation (Middlebury, Conn.), including Kemamide S (a stearamide), Kemamide B (a behenamide), Kemamide O (an oleamide), Kemamide E (an erucamide), and Kemamide (an N,N'-ethylenebisstearamide). Other commercially available slip agents include Erucamid ER (an erucamide).

Generally preferred concentrations of the slip agent are in the range of from about 0.001% to about 0.5% by weight of the composition, preferably of from about 0.01% to about 0.4% by weight and most preferably of from about 0.1 parts to about 0.3% by weight based on the weight of the composition. Generally preferred concentrations of the saturated fatty acid amide or ethylene-bis(amide) are in the range of from about 0.001 parts to about 0.5 parts by weight, preferably from about 0.025 parts to about 0.25 parts by weight, more preferably from about 0.05 parts to about 0.15 parts by weight based on the weight of the composition. Generally, preferred concentrations of the unsaturated fatty acid amide or ethylene-bis(amide) are in the range of from about 0.001 parts to about 1 part by weight, preferably from about 0.05 parts to about 0.75 parts by weight and most preferably of from about 0.1 parts to about 0.3 parts by weight based on the weight of the composition.

In another embodiment, functionalized oils other than the amide slip agent(s) are substantially absent from the polyolefin compositions of the present invention. Functionalized oils comprise carbon and hydrogen and also include functional groups to more than an appreciable extent, as defined below. By "substantially absent", it is meant that these compounds are not added deliberately to the compositions and, if present, are present at less than 1 wt %, more preferably less than 0.8 wt %, more preferably less than 0.5 wt %, more preferably less than 0.1 wt %, more preferably less than 0.05 wt %, more preferably less than 0.01 wt %, more preferably less than 0.001 wt %, based upon the weight of the composition.

The slip agent is preferably present at 0.001 to 1 wt %, alternately 0.01 to 0.75 wt %, alternately 0.05 to 0.5 wt %, alternately 0.05 to 0.3 wt %, alternately 0.1 to 0.25 wt %, based upon the weight of the composition. In one embodiment, the composition comprises 1 to 15 wt % NFP, 85 to 99 wt % polypropylene, 0.02 to 0.5 wt % nucleating agent, and 0.01 to 0.5 wt % slip agent, based on the weight of the composition.

Fillers

In one embodiment of the present invention, the composition and or the NFP or some portion of the NFP is blended with a filler, desirably a porous filler. The NFP and filler may be blended by, for example, a tumbler or other wet blending apparatus, for a time suitable to form a homogenous composition of NFP and filler, desirably from 1 minute to 5 hours. In another embodiment, a filler may be pre-contacted or pre-absorbed with the NFP or some portion of the NFP prior to contacting the filler with the polyolefin. In another embodiment, the filler, polyolefin, and NFP are contacted simultaneously (or in the same blending apparatus). In any case, the NFP may be present from 0.1 to 50 wt % of the composition in one embodiment, and from 0.2 to 40 wt % in another embodiment, and from 0.3 to 30 wt % in yet another embodiment, and from 0.5 to 25 wt % in yet another embodiment, and from 1 to 20 wt % in yet another embodiment.

Desirable fillers include but not limited to mineral aggregates, fibers, natural and synthetic clays including nanoclays and organoclays, sand, glass beads, and the like, and may include any other porous or nonporous fillers and supports known in the art. Preferred fillers include talc, wollastonite, carbon black, graphite, mica, wollastonite, titanium dioxide, silicon carbide, silica, silicon dioxide and other oxides of silica (precipitated or not), calcium silicate, calcium and barium sulfates, calcium and lead carbonates, magnesium oxysulfates, antimony oxide, zinc white, lithopone, zircon, corundum, spinel, apatite, Barytes powder, magnesiter, dolomite, hydrotalcite compounds of the ions Mg, Ca, or Zn with Al, Cr or Fe and $CO_3$ and/or $HPO_4$ (hydrated or not), quartz powder, hydrochloric magnesium carbonate, alumina, chrome, phosphorous and brominated flame retardants, antimony trioxide, silicone, other metal oxides, other metal carbonates, other metal hydroxides, and blends thereof.

Preferred fibers include glass fibers, carbon fibers, and natural and synthetic polymer fibers including PET fibers and rayon fibers.

Preferred clays include nanoclays or organoclays to produce a nanocomposite. These clays may comprise one or more of ammonium, primary alkylammonium, secondary alkylammonium, tertiary alkylammonium, quaternary alkylammonium, phosphonium derivatives of aliphatic, aromatic or arylaliphatic amines, phosphines or sulfides or sulfonium derivatives of aliphatic, aromatic or arylaliphatic amines, phosphines or sulfides. The organoclay may be selected from one or more of montmorillonite, sodium montmorillonite, calcium montmorillonite, magnesium montmorillonite, nontronite, beidellite, volkonskoite, laponite, hectorite, saponite, sauconite, magadite, kenyaite, sobockite, svindordite, stevensite, vermiculite, halloysite, aluminate oxides, hydrotalcite, illite, rectorite, tarosovite, ledikite, and/or florine mica. The organoclay is preferably present in the nanocomposite at from 0.1 to 50 wt %, based on the total weight of the nanocomposite.

Preparing the Polyolefin/NFP Blend

The polyolefin suitable for use in the present invention can be in any physical form when used to blend with the NFP and nucleating agent of the invention. In one embodiment, reactor granules, defined as the granules of polymer that are isolated from the polymerization reactor prior to any processing procedures, are used to blend with the NFP and nucleating agent of the invention. The reactor granules typically have an average diameter of from 50 μm to 10 mm in one embodiment, and from 10 μm to 5 mm in another embodiment. In another embodiment, the polyolefin is in the form of pellets, such as, for example, having an average diameter of from 1 mm to 10 mm that are formed from melt extrusion of the reactor granules.

One method of blending the NFP with the polyolefin is to contact the components in a tumbler, the polyolefin being in the form of reactor granules. This works particularly well with polypropylene and polypropylene blends. This can then be followed, if desired, by melt blending in an extruder. Another method of blending the components is to melt blend the polyolefin pellets with the NFP directly in an extruder or batch mixer, such as a Brabender mixer.

Thus, in the cases of injection molding of various articles, simple solid state blends of the pellets serve equally as well as pelletized melt state blends of raw polymer granules, of granules with pellets, or of pellets of the two components since the forming process includes a remelting and mixing of the raw material. In the process of compression molding of medical devices, however, little mixing of the melt components occurs, and a pelletized melt blend would be preferred over simple solid state blends of the constituent pellets and/or granules. Those skilled in the art will be able to determine the appropriate procedure for blending of the polymers to balance the need for intimate mixing of the component ingredients with the desire for process economy.

The polyolefin, nucleating agent and NFP can be blended by any suitable means, and are typically blended to obtain a homogeneous, single phase mixture. For example, they may be blended in a tumbler, static mixer, batch mixer, extruder, or a combination thereof. The mixing step may take place as part of a processing method used to fabricate articles, such as in the extruder on an injection molding machine or fiber line. Typically, the components of the present invention are blended by any suitable means (such as static mixer, batch mixer, extruder, or a combination thereof) that is sufficient to achieve an adequate dispersion of nucleating agent and/or plasticizer in the polymer. The mixing step may involve first dry blending using, for example, a tumble blender. It may also involve a "master batch" approach, where the final plasticizer and/or nucleating agent concentration is achieved by combining neat polymer with an appropriate amount of plasticized polymer that had been previously prepared at a higher plasticizer and/or nucleating agent concentration. Dispersion may take place as part of a processing method used to fabricate articles, such as in the extruder on an injection molding machine or fiber line. The plasticizer and a nucleating agent may be injected into the extruder barrel or introduced at the feed throat of the extruder to save the step of preblending. This is a preferred method when a larger percentage of plasticizer is to be used or large quantities of plasticized resin are desired.

More particularly, the components of the plasticized polyolefin composition of the present invention may be blended by any suitable means to form the plasticized polyolefin, which is then suitable for further processing into useful articles. In one aspect of the invention, the polyolefin, nucleating agent and NFP are blended, or melt blended, in an apparatus such as an extruder or batch mixer. The polyolefin may also be blended with the nucleating agent and the NFP using a tumbler, double-cone blender, ribbon blender, or other suitable blender. In yet another embodiment, the polyolefin, nucleating agent and NFP are blended by a combination of, for example, a tumbler, followed by melt blending in an extruder. Extrusion technology for polypropylene and polypropylene blends is described in more detail in, for example, PLASTICS EXTRUSION TECHNOLOGY 26-37 (Friedhelm Hensen, ed. Hanser Publishers 1988) and in POLYPROPYLENE HANDBOOK 304-348 (Edward P. Moore, Jr. ed., Hanser Publishers 1996).

More particularly, the components of the plasticized polyolefin composition of the present invention may be blended in solution by any suitable means to form the plasticized polyolefin composition, by using a solvent that dissolves all components to a significant extent. The blending may occur at any temperature or pressure where the NFP, the nucleating agent and the polyolefin remain in solution. Preferred conditions include blending at high temperatures, such as 20° C. or more, preferably 40° C. or more over the melting point of the polyolefin. For example iPP would typically be solution blended with the NFP and the nucleating agent at a temperature of 200° C. or more, preferably 220° C. or more. Such solution blending would be particularly useful in processes where the polyolefin is made by solution process and the NFP and nucleating agent are added directly to the finishing train, rather than added to the dry polymer in another blending step altogether. Such solution blending would also be particularly useful in processes where the polyolefin is made in a bulk or high pressure process where the polymer, nucleating agent and the NFP were soluble in the monomer. As with the solution process the NFP and the nucleating agent are added directly to the finishing train, rather than added to the dry polymer in another blending step altogether.

In one embodiment of compositions of the present invention, conventional plasticizers such as are commonly used for poly(vinyl chloride) are substantially absent. In particular, plasticizers such as phthalates, adipates, trimellitate esters, polyesters, and other functionalized plasticizers as disclosed in, for example, U.S. Pat. Nos. 3,318,835; 4,409,345; WO 02/31044 A1; and PLASTICS ADDITIVES 499-504 (Geoffrey Pritchard, ed., Chapman & Hall 1998) are substantially absent. By "substantially absent", it is meant that these compounds are not added deliberately to the compositions and if present at all, are present at less than 0.5 wt %.

Oils such as naphthenic and other aromatic containing oils are preferably present to less than 0.5 wt % of the compositions of the invention in a further embodiment. Also, aromatic moieties and carbon-carbon unsaturation are substantially absent from the non-functionalized plasticizers used in the present invention in yet another embodiment. Aromatic moieties include a compound whose molecules have the ring structure characteristic of benzene, naphthalene, phenanthrene, anthracene, etc. By "substantially absent", it is meant that these aromatic compounds or moieties are not added deliberately to the compositions, and if present, are present to less than 0.5 wt % of the composition.

In another embodiment of compositions of the present invention, conventional plasticizers, elastomers, or "compatibilizers" such as low molecular weight polyethylene are substantially absent. In particular, ethylene homopolymers and copolymers having a weight average molecular weight of from 500 to 10,000 are substantially absent. Such polyethylene compatibilizers are disclosed in, for example, WO 01/18109A1. By "substantially absent", it is meant that these compounds are not added deliberately to the compositions and, if present, are present at less than 5 wt %, more preferably less than 4 wt %, more preferably less than 3 wt %, more preferably less than 2 wt %, more preferably less than 1 wt %, more preferably less than 0.5 wt %, based upon the weight of the polyolefin, the ethylene polymer or copolymer, and the NFP.

The plasticized polyolefin compositions of the present invention may also contain other additives. Those additives include adjuvants, oils, block, antiblock, color masterbatches, processing aids, neutralizers, lubricants, waxes, antioxidants, acid scavengers, stabilizers, surfactants, anticorrosion agents, cavitating agents, blowing agents, other UV absorbers such as chain-breaking antioxidants, etc., quenchers, antistatic agents, pigments, dyes, fillers and cure agents such as peroxide. Typical additives used in polypropylene and polypropylene blends are described in N. Pasquini (Ed.): "Polypropylene Handbook" $2^{nd}$ Ed., Hanser Publishers, 2005. The additives may be present in the typically effective amounts well known in the art, such as 0.001 wt % to 10 wt %, preferably 0.01 to 1 wt %. Preferably, dyes and other colorants common in the industry may be present from 0.01 to 10 wt % in one embodiment, and from 0.1 to 6 wt % in another embodiment.

In particular, antioxidants and stabilizers such as organic phosphites, hindered amines, and phenolic antioxidants may be present in the plasticized polyolefin compositions of the invention from 0.001 to 2 wt % in one embodiment, and from 0.01 to 0.8 wt % in another embodiment, and from 0.02 to 0.5 wt % in yet another embodiment. Non-limiting examples of organic phosphites that are suitable are tris(2,4-di-tert-butylphenyl)phosphite (IRGAFOS 168) and di(2,4-di-tert-butylphenyl)pentaerithritol diphosphite (ULTRANOX 626). Non-limiting examples of hindered amines include poly[2-N,N'-di(2,2,6,6-tetramethyl-4-piperidinyl)-hexanediamine-4-(1-amino-1,1,3,3-tetramethylbutane)sym-triazine] (CHIMASORB 944); bis(1,2,2,6,6-pentamethyl-4-piperidyl) sebacate (TINUVIN 770). Non-limiting examples of phenolic antioxidants include pentaerythrityl tetrakis(3,5-di-tert-butyl-4-hydroxyphenyl)propionate (IRGANOX 1010); and 1,3,5-Tri(3,5-di-tert-butyl-4-hydroxybenzyl-isocyanurate (IRGANOX 3114). Preferred antioxidants include phenolic antioxidants, such as Irganox 1010, Irganox, 1076 both available from Ciba-Geigy.

Preferred oils include paraffinic or naphthenic oils such as Primol 352, or Primol 876 available from ExxonMobil Chemical France, S.A. in Paris, France. More preferred oils include aliphatic naphthenic oils, white oils or the like.

In some embodiments the plasticized polyolefin composition produced by this invention may be blended with one or more other polymers, including but not limited to, thermoplastic polymer(s) and/or elastomer(s).

Thermoplastic polymers typically include, but are not limited to, polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Preferred polyolefins include, but are not limited to, polymers comprising one or more linear, branched or cyclic $C_2$ to $C_{40}$ olefins, preferably polymers comprising propylene copolymerized with one or more $C_3$ to $C_{40}$ olefins, preferably a $C_3$ to $C_{20}$ alpha olefin, more preferably $C_3$ to $C_{10}$ alpha-olefins. More preferred polyolefins include, but are not limited to, polymers comprising ethylene including but not limited to ethylene copolymerized with a $C_3$ to $C_{40}$ olefin, preferably a $C_3$ to $C_{20}$ alpha olefin, more preferably propylene and or butene.

Examples of preferred elastomers include, but are not limited to, ethylene propylene rubber, ethylene propylene diene monomer rubber, styrenic block copolymer rubbers (including SI, SIS, SB, SBS, SIBS and the like, where S=styrene, I=isobutylene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In another embodiment, the plasticized polyolefin composition may further be combined with one or more of ethylene vinyl acetate, low density polyethylene (density 0.915 to less than 0.935 g/cm³) linear low density polyethylene, ultra low density polyethylene (density 0.86 to less than 0.90 g/cm³), very low density polyethylene (density 0.90 to less than 0.915 g/cm³), medium density polyethylene (density 0.935 to less than 0.945 g/cm³), high density polyethylene (density 0.945 to 0.98 g/cm³), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, crosslinked polyethylene, copolymers of ethylene and vinyl alcohol (EVOH), polymers of aromatic monomers such as polystyrene, poly-1 esters, polyacetal, polyvinylidine fluoride, polyethylene glycols and/or polyisobutylene. Preferred polymers include those available from Exxon Chemical Company in Baytown, Tex. under the tradenames EXCEED™ and EXACT™.

In another embodiment, tackifiers may be blended with the plasticized polyolefin composition of this invention. Examples of useful tackifiers include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, and hydrogenated rosin esters. In some embodiments the tackifier is hydrogenated. In other embodiments the tackifier is non-polar. (Non-polar meaning that the tackifier is substantially free of monomers having polar groups. Preferably the polar groups are not present, however if they are preferably they are not present at more that 5 wt %, preferably not more that 2 wt %, even more preferably no more than 0.5 wt %.) In some embodiments the tackifier has a softening point (Ring and Ball, as measured by ASTM E-28) of 80° C. to 140° C., preferably 100° C. to 130° C. The tackifier, if present, is typically present at about 1 wt % to about 50 wt %, based upon the weight of the blend, more preferably 10 wt % to 40 wt %, even more preferably 20 wt % to 40 wt %. Preferably however, tackifier is not present, or if present, is present at less than 10 wt %, preferably less than 5 wt %, more preferably at less than 1 wt %.

Applications

The resultant plasticized polyolefin compositions of the present invention may be processed by any suitable means such as by calendering, casting, coating, compounding, extrusion, foamed, laminated, blow molding, compression molding, injection molding, thermoforming, transfer molding, cast molding, rotational molding, casting such as for films, spun or melt bonded such as for fibers, or other forms of processing such as described in, for example, PLASTICS PROCESSING (Radian Corporation, Noyes Data Corp. 1986). More particularly, with respect to the physical process of producing the blend, sufficient mixing should take place to assure that a uniform blend will be produced prior to conversion into a finished product.

The compositions of this invention (and blends thereof as described above) may be used in any known thermoplastic application involving molding or extrusion. Examples include uses in films, tapes, sheets, tubing, hose, sheeting, wire and cable coating, shoesoles, bumpers, gaskets, bellows, films, fibers, elastic fibers, nonwovens, spunbonds, sealants, surgical gowns and medical devices. These articles and/or devices may be made or formed by any useful forming means for forming polyolefins. This will include, at least, molding including compression molding, injection molding, blow molding, and transfer molding; film blowing or casting; extrusion, and thermoforming; as well as by lamination, pultrusion, protrusion, draw reduction, rotational molding, spin-bonding, melt spinning, melt blowing; or combinations thereof. Use of at least thermoforming or film applications allows for the possibility of and derivation of benefits from uniaxial or biaxial orientation of the radiation tolerant material.

Non-limiting examples of desirable articles of manufacture made from compositions of the invention include films, sheets, fibers, tubes, pipes, automotive components, furniture, sporting equipment, food storage containers, transparent and semi-transparent articles, toys, tubing and pipes, medical devices, cookware and storage ware, sportswear, sterilizable medical devices, sterilization containers, nonwoven fibers and fabrics (such as drapes, gowns, filters, hygiene products, diapers), oriented films and other items where softness, high impact strength, and impact strength below freezing is important. Fabrication of the plasticized polyolefins of the invention to form these articles may be accomplished by injection molding, extrusion, thermoforming, blow molding, roto-molding, spunbonding, meltblowing, fiber spinning, blown film, stretching for oriented films, and other common processing methods.

In a preferred embodiment, the NFP is an isoparaffin comprising $C_6$ to $C_{25}$ isoparaffins and/or a polyalphaolefin comprising $C_{10}$ to $C_{100}$ n-paraffins, the polyolefin is preferably a polypropylene homopolymer, copolymer, impact copolymer, or blends thereof, and may include a plastomer and the composition is used to make one or more of films, sheets, fibers, woven and nonwoven fabrics, tubes, pipes, automotive components, furniture, sporting equipment, food storage containers, transparent and semi-transparent articles, toys, tubing and pipes, and medical devices.

Films

Polyolefin films are widely used; for example, in shopping bags, pressure sensitive tape, gift wrap, labels, food packaging, etc. Most of these applications require high tear (in machine and transverse directions) and impact strengths, puncture resistance, high gloss, low haze, and a dry feel.

The compositions described above and the blends thereof may be formed into monolayer or multilayer films appropriate for such applications. These films may be formed by any of the conventional techniques known in the art including extrusion, co-extrusion, extrusion coating, lamination, blowing and casting. The film may be obtained by the flat film or tubular process which may be followed by orientation in an uniaxial direction or in two mutually perpendicular directions in the plane of the film. One or more of the layers of the film may be oriented in the transverse and/or longitudinal directions to the same or different extents. This orientation may occur before or after the individual layers are brought together. For example a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15 preferably 7 to 9. However in another embodiment the film is oriented to the same extent in both the MD and TD directions.

In another embodiment the layer comprising the plasticized polyolefin composition of this invention (and/or blends thereof) may be combined with one or more other layers. The other layer(s) may be any layer typically included in multi-layer film structures. For example the other layer or layers may be:

1. Polyolefins

Preferred polyolefins include homopolymers or copolymers of $C_2$ to $C_{40}$ olefins, preferably $C_2$ to $C_{20}$ olefins, preferably a copolymer of an alpha-olefin and another olefin or alpha-olefin (ethylene is defined to be an alpha-olefin for purposes of this invention). Particularly preferred are homopolyethylene, homopolypropylene, propylene copolymerized with ethylene and or butene, ethylene copolymerized with one or more of propylene, butene or hexene, and optional dienes. Preferred examples include thermoplastic polymers such as ultra low density polyethylene, very low density polyethylene, linear low density polyethylene, low density polyethylene, medium density polyethylene, high density polyethylene, polypropylene, isotactic polypropylene, highly isotactic polypropylene, syndiotactic polypropylene, random copolymer of propylene and ethylene and/or butene and/or hexene, elastomers such as ethylene propylene rubber, ethylene propylene diene monomer rubber, neoprene, and blends of thermoplastic polymers and elastomers, such as for example, thermoplastic elastomers and rubber toughened plastics.

2. Polar Polymers

Preferred polar polymers include homopolymers and copolymers of esters, amides, actates, anhydrides, copolymers of a $C_2$ to $C_{20}$ olefin, such as ethylene and/or propylene and/or butene with one or more polar monomers such as acetates, anhydrides, esters, alcohol, and or acrylics. Preferred examples include polyesters, polyamides, ethylene vinyl acetate copolymers, and polyvinyl chloride.

3. Cationic Polymers

Preferred cationic polymers include polymers or copolymers of geminally disubstituted olefins, alpha-heteroatom olefins and/or styrenic monomers. Preferred geminally disubstituted olefins include isobutylene, isopentene, isoheptene, isohexene, isooctene, iso-decene, and isododecene. Preferred alpha-heteroatom olefins include vinyl ether and vinyl carbazole, preferred styrenic monomers include styrene, alkyl styrene, para-alkyl styrene, alpha-methyl styrene, chloro-styrene, and bromo-para-methyl styrene. Preferred examples of cationic polymers include butyl rubber, isobutylene copolymerized with para methyl styrene, polystyrene, and poly-alpha-methyl styrene.

4. Miscellaneous

Other preferred layers can be paper, wood, cardboard, metal, metal foils (such as aluminum foil and tin foil), metallized surfaces, glass (including silicon oxide (SiO.x) coatings applied by evaporating silicon oxide onto a film surface), fabric, spunbonded fibers, and non-wovens (particularly polypropylene spun bonded fibers or non-wovens), and substrates coated with inks, dyes, pigments, and the like.

The films may vary in thickness depending on the intended application, however films of a thickness from 1 to 250 μm are usually suitable. Films intended for packaging are usually from 10 to 60 microns thick. The thickness of the sealing layer is typically 0.2 to 50 μm. There may be a sealing layer on one or more of the inner, middle and outer surfaces of the film or the sealing layer may be present on only the inner or the outer surface.

Additives such as block, antiblock, antioxidants, pigments, fillers, processing aids, UV stabilizers, neutralizers, lubricants, surfactants and/or nucleating agents may also be present in one or more than one layer in the films. Preferred additives include silicon dioxide, titanium dioxide, polydimethylsiloxane, talc, dyes, wax, calcium stearate, carbon black, low molecular weight resins and glass beads.

In another embodiment one more layers may be modified by corona treatment, electron beam irradiation, gamma irradiation, or microwave irradiation. In a preferred embodiment one or both of the surface layers is modified by corona treatment.

The films described herein may also comprise from 5 to 60 wt %, based upon the weight of the polymer and the resin, of a hydrocarbon resin. The resin may be combined with the polymer of the seal layer(s) or may be combined with the polymer in the core layer(s). The resin preferably has a softening point above 100° C., even more preferably from 130 to 180° C. Preferred hydrocarbon resins include those described above. The films comprising a hydrocarbon resin may be oriented in uniaxial or biaxial directions to the same or different degrees.

Molded Products

The plasticized polyolefin composition described above may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

The compositions described herein may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. An embodiment of a thermoforming sequence is described, however this should not be construed as limiting the thermoforming methods useful with the compositions of this invention. First, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The forming tool can be either "male" or "female" type tools. The tool stays closed to cool the film and the tool is then opened. The shaped laminate is then removed from the tool.

Thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution. In one embodiment, an articulating rack lifts the heated laminate towards a male forming tool, assisted by the application of a vacuum from orifices in the male forming tool. Once the laminate is firmly formed about the male forming tool, the thermoformed shaped laminate is then cooled, typically by blowers. Plug-assisted forming is generally used for small, deep drawn parts. Plug material, design, and timing can be critical to optimization of the process. Plugs made from insulating foam avoid premature quenching of the plastic. The plug shape is usually similar to the mold cavity, but smaller and without part detail. A round plug bottom will usually promote even material distribution and uniform side-wall thickness. For a thermoplastic polymer such as polypropylene, fast plug speeds generally provide the best material distribution in the part.

The shaped laminate is then cooled in the mold. Sufficient cooling to maintain a mold temperature of 30° C. to 65° C. is desirable. The part is below 90° C. to 100° C. before ejection in one embodiment. For the good behavior in thermoforming, the lowest melt flow rate polymers are desirable. The shaped laminate is then trimmed of excess laminate material.

Blow molding is another suitable forming means, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley & Sons 1990).

In yet another embodiment of the formation and shaping process, profile co-extrusion can be used. The profile co-extrusion process parameters are as above for the blow molding process, except the die temperatures (dual zone top and bottom) range from 150 to 235° C., the feed blocks are from 90 to 250° C., and the water cooling tank temperatures are from 10 to 40° C.

One embodiment of an injection molding process is described as follows. The shaped laminate is placed into the injection molding tool. The mold is closed and the substrate material is injected into the mold. The substrate material has a melt temperature between 200 and 300° C. in one embodiment, and from 215 and 250° C. in another embodiment, and is injected into the mold at an injection speed of between 2 and 10 seconds. After injection, the material is packed or held at a predetermined time and pressure to make the part dimensionally and aesthetically correct. Typical time periods are from 5 to 25 seconds and pressures from 1,380 kPa to 10,400 kPa. The mold is cooled between 10 and 70° C. to cool the substrate. The temperature will depend on the desired gloss and appearance desired. Typical cooling time is from 10 to 30 seconds, depending on part on the thickness. Finally, the mold is opened and the shaped composite article ejected.

Likewise, molded articles may be fabricated by injecting molten polymer into a mold that shapes and solidifies the molten polymer into desirable geometry and thickness of molded articles. A sheet may be made either by extruding a substantially flat profile from a die, onto a chill roll, or alternatively by calendaring. The sheet will generally be considered to have a thickness of from 10 mils to 100 mils (254 µm to 2540 µm), although the sheet may be substantially thicker. Tubing or pipe may be obtained by profile extrusion for uses in medical, potable water, land drainage applications or the like. The profile extrusion process involves the extrusion of molten polymer through a die. The extruded tubing or pipe is then solidified by chill water or cooling air into a continuous extruded articles. The tubing will generally be in the range of from 0.31 cm to 2.54 cm in outside diameter, and have a wall thickness of in the range of from 254 µm to 0.5 cm. The pipe will generally be in the range of from 2.54 cm to 254 cm in outside diameter, and have a wall thickness of in the range of from 0.5 cm to 15 cm. Sheets made from the products of an embodiment of a version of the present invention may be used to form containers. Such containers may be formed by thermoforming, solid phase pressure forming, stamping and other shaping techniques. Sheets may also be formed to cover floors or walls or other surfaces.

In an embodiment of the thermoforming process, the oven temperature is between 160° C. and 195° C., the time in the oven between 10 and 20 seconds, and the die temperature, typically a male die, between 10° C. and 71° C. The final thickness of the cooled (room temperature), shaped laminate is from 10 µm to 6000 µm in one embodiment, from 200 µm to 6000 µm in another embodiment, and from 250 µm to 3000 µm in yet another embodiment, and from 500 µm to 1550 µm in yet another embodiment, a desirable range being any combination of any upper thickness limit with any lower thickness limit.

In an embodiment of the injection molding process, wherein a substrate material in injection molded into a tool including the shaped laminate, the melt temperature of the substrate material is between 230° C. and 255° C. in one embodiment, and between 235° C. and 250° C. in another embodiment, the fill time from 2 to 10 seconds in one embodiment, from 2 to 8 seconds in another embodiment, and a tool temperature of from 25° C. to 65° C. in one embodiment, and from 27° C. and 60° C. in another embodiment. In a desirable embodiment, the substrate material is at a temperature that is hot enough to melt any tie-layer material or backing layer to achieve adhesion between the layers.

In yet another embodiment of the invention, the compositions of this invention may be secured to a substrate material using a blow molding operation. Blow molding is particularly useful in such applications as for making closed articles such as fuel tanks and other fluid containers, playground equipment, outdoor furniture and small enclosed structures. In one embodiment of this process, Compositions of this invention are extruded through a multi-layer head, followed by placement of the uncooled laminate into a parison in the mold. The mold, with either male or female patterns inside, is then closed and air is blown into the mold to form the part.

It will be understood by those skilled in the art that the steps outlined above may be varied, depending upon the desired result. For example, the extruded sheet of the compositions of this invention may be directly thermoformed or blow molded without cooling, thus skipping a cooling step. Other parameters may be varied as well in order to achieve a finished composite article having desirable features.

Preferred articles made using the plasticized polyolefins of this Invention include cookware, storageware, toys, medical devices, sterilizable medical devices, sterilization containers, healthcare items, sheets, crates, containers, bottles, packaging, wire and cable jacketing, pipes, geomembranes, sporting equipment, chair mats, tubing, profiles, instrumentation sample holders and sample windows, outdoor furniture (e.g., garden furniture), playground equipment, automotive, boat and water craft components, and other such articles. In particular, the compositions are suitable for automotive components such as bumpers, grills, trim parts, dashboards and instrument panels, exterior door and hood components, spoiler, wind screen, hub caps, mirror housing, body panel, protective side molding, and other interior and external components associated with automobiles, trucks, boats, and other vehicles.

EXPERIMENTAL METHODS

Dynamic Mechanical Thermal Analysis (DMTA)

The glass transition temperature ($T_g$) is measured using dynamic mechanical thermal analysis (DMTA). This test provides information about the small-strain mechanical response (relaxation behavior) of a sample as a function of temperature over a temperature range that includes the glass transition region and the visco-elastic region prior to melting.

Typically, samples were tested using a three point bending configuration (TA Instruments DMA 2980). A solid rectangular compression molded bar was placed on two fixed supports; a movable clamp applied a periodic deformation to the sample midpoint at a frequency of 1 Hz and amplitude of 20 µm. The sample was initially cooled to −130° C. then heated to 60° C. at a heating rate of 3° C./min. In some cases, compression molded bars were tested using other deformation configurations, namely dual cantilever bending and tensile elongation (Rheometrics RSAII). The periodic deformation under these configurations was applied at a frequency of 1 Hz and strain amplitude of 0.05%. The sample was cooled to −130° C. and then heated to 60° C. at a rate of 2° C./min. The slightly difference in heating rate does not influence the glass transition temperature measurements significantly.

The output of these DMTA experiments is the storage modulus (E') and loss modulus (E"). The storage modulus measures the elastic response or the ability of the material to store energy, and the loss modulus measures the viscous response or the ability of the material to dissipate energy. Tan-delta is the ratio of E"/E' and gives a measure of the damping ability of the material. The beginning of the broad glass transition (β-relaxation) is identified as the extrapolated tangent to the tan-delta peak. In addition, the peak temperature and area under the peak are also measured to more fully characterize the transition from glassy to visco-elastic region. Thus the glass transition temperature is the peak temperature associated with the β-relaxation peak.

Differential Scanning Calorimetry (DSC)

Crystallization temperature ($T_c$) and melting temperature ($T_m$) are measured using Differential Scanning Calorimetry (DSC) using commercially available equipment such as a TA Instruments 2920 DSC. Typically, 6 to 10 mg of molded polymer or plasticized polymer is sealed in an aluminum pan and loaded into the instrument at room temperature. Melting data (first heat) is acquired by heating the sample to at least 30° C. above its melting temperature, typically 220° C. for polypropylene, at a heating rate of 10° C./min. The sample is held for at least 5 minutes at this temperature to destroy its thermal history. Crystallization data are acquired by cooling the sample from the melt to at least 50° C. below the crystallization temperature, typically −50° C. for polypropylene, at a cooling rate of 20° C./min. The sample is held at this temperature for at least 5 minutes, and finally heated at 10° C./min to acquire additional melting data (second heat). The endothermic melting transition (first and second heat) and exothermic crystallization transition are analyzed for onset of transition and peak temperature. The melting temperatures reported are the peak melting temperatures from the second heat unless otherwise specified. For polymers displaying multiple peaks, the melting point (or melting temperature) is defined to be the peak melting temperature (i.e., associated with the largest endothermic calorimetric response in that range of temperatures) from the DSC melting trace; likewise, the crystallization temperature is defined to be the peak crystallization temperature (i.e., associated with the largest exothermic calorimetric response in that range of temperatures) from the DSC crystallization trace.

Areas under the DSC curve are used to determine the heat of transition (heat of fusion, $H_f$, upon melting or heat of crystallization, $H_c$, upon crystallization), which can be used to calculate the degree of crystallinity (also called the percent crystallinity). The percent crystallinity (X %) is calculated using the formula: [area under the curve (in J/g)/H ° (in J/g)]*100, where H ° is the heat of fusion for the homopolymer of the major monomner component. These values for H ° are to be obtained from the *Polymer Handbook, Fourth Edition*, published by John Wiley and Sons, New York 1999, except that a value of 290 J/g is used as the equilibrium heat of fusion (H °) for 100% crystalline polyethylene, a value of 140 J/g is used as the equilibrium heat of fusion (H °) for 100% crystalline polybutene, and a value of 207 J/g (H °) is used as the heat of fusion for a 100% crystalline polypropylene.

Crystallization half time at 125° C. was measured on a Perkin Elmer Pyris I DSC. The sample was melted at 200° C. for 10 min; cooled to 160° C. at 150° C./min and then to 140° C. at 40° C./min; held at 140° C. for 45 min; heated again to 200° C. at 150° C./min and held there for 10 min; cooled to 145° C. at 150° C./min and then to 125° C. at 40° C./min; and held at 125° C. for 45 min to acquire crystallization data. The crystallization half-time is the time required for half of the final crystallinity to develop, as measured by ΔHc; that is, if the final $\Delta H_c$ after 45 min is X J/g, the crystallization half time is the time required for $\Delta H_c$ to reach X/2 J/g. Crystallization half time at 140° C. was measured identically except the final temperature was 140° C. instead of 125° C.

Size-Exclusion Chromatography of Polymers (SEC-3D)

Molecular weight (weight-average molecular weight, $M_w$, number-average molecular weight, $M_n$, and molecular weight distribution, $M_w/M_n$ or MWD) were determined using a High Temperature Size Exclusion Chromatograph (either from Waters Corporation or Polymer Laboratories), equipped with a differential refractive index detector (DRI), an online light scattering (LS) detector, and a viscometer. Experimental details not described below, including how the detectors were calibrated, are described in: T. Sun, P. Brant, R. R. Chance, and W. W. Graessley, Macromolecules, Volume 34, Number 19, 6812-6820, (2001).

Three Polymer Laboratories PLgel 10 mm Mixed-B columns were used. The nominal flow rate was 0.5 cm³/min, and the nominal injection volume was 300 μL. The various transfer lines, columns and differential refractometer (the DRI detector) were contained in an oven maintained at 135° C.

Solvent for the SEC experiment was prepared by dissolving 6 grams of butylated hydroxy toluene as an antioxidant in 4 liters of Aldrich reagent grade 1, 2, 4 trichlorobenzene (TCB). The TCB mixture was then filtered through a 0.7 μm glass pre-filter and subsequently through a 0.1 μm Teflon filter. The TCB was then degassed with an online degasser before entering the SEC. Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units are 1.463 g/ml at room temperature and 1.324 g/ml at 135° C. The injection concentration ranged from 1.0 to 2.0 mg/ml, with lower concentrations being used for higher molecular weight samples. Prior to running each sample the DRI detector and the injector were purged. Flow rate in the apparatus was then increased to 0.5 ml/minute, and the DRI was allowed to stabilize for 8-9 hours before injecting the first sample. The LS laser was turned on 1 to 1.5 hours before running samples.

The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the same as described below for the light scattering (LS) analysis. Units on parameters throughout this description of the SEC method are such that concentration is expressed in g/cm³, molecular weight is expressed in g/mole, and intrinsic viscosity is expressed in dL/g.

The light scattering detector used was a Wyatt Technology High Temperature mini-DAWN. The polymer molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c$$

Here, $\Delta R(\theta)$ is the measured excess Rayleigh scattering intensity at scattering angle θ, c is the polymer concentration determined from the DRI analysis, $A_2$ is the second virial coefficient [for purposes of this invention and the claims thereto, $A_2$=0.0006 for propylene polymers and 0.001 otherwise], P(θ) is the form factor for a monodisperse random coil (M. B. Huglin, LIGHT SCATTERING FROM POLYMER SOLUTIONS, Academic Press, 1971), and $K_o$ is the optical constant for the system:

$$K_o = \frac{4\pi^2 n^2 (dn/dc)^2}{\lambda^4 N_A}$$

in which $N_A$ is Avogadro's number, and (dn/dc) is the refractive index increment for the system. The refractive index, n=1.500 for TCB at 135° C. and λ=690 nm. For purposes of this invention and the claims thereto (dn/dc)=0.104 for propylene polymers and 0.1 otherwise.

A high temperature Viscotek Corporation viscometer, which has four capillaries arranged in a Wheatstone bridge configuration with two pressure transducers, was used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, $[\eta]$, at each point in the chromatogram is calculated from the following equation:

$$\eta_s = c[\eta] + 0.3(c[\eta])^2$$

where c is concentration and was determined from the DRI output.

The branching index (g') is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromotographic slices, i, between the integration limits. The branching index g' is defined as:

$$g' = \frac{[\eta]_{avg}}{kM_v^\alpha}$$

where, for purpose of this invention and claims thereto, $\alpha=0.695$ for ethylene, propylene, and butene polymers; and $k=0.000579$ for ethylene polymers, $k=0.000262$ for propylene polymers, and $k=0.000181$ for butene polymers. $M_v$ is the viscosity-average molecular weight based on molecular weights determined by LS analysis.

$^{13}$C-NMR Spectroscopy

Polymer microstructure was determined by $^{13}$C-NMR spectroscopy, including the concentration of isotactic and syndiotactic diads ([m] and [r]), triads ([mm] and [rr]), and pentads ([mmmm] and [rrrr]). Samples were dissolved in $d_2$-1,1,2,2-tetrachloroethane. Spectra were recorded at 125° C. using a NMR spectrometer of 75 or 100 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, $^{13}$C-NMR Method", Academic Press, New York, 1977. The percent of methylene sequences of two in length, % $(CH_2)_2$, were calculated as follows: the integral of the methyl carbons between 14-18 ppm (which are equivalent in concentration to the number of methylenes in sequences of two in length) divided by the sum of the integral of the methylene sequences of one in length between 45-49 ppm and the integral of the methyl carbons between 14-18 ppm, times 100. This is a minimum calculation for the amount of methylene groups contained in a sequence of two or more since methylene sequences of greater than two have been excluded. Assignments were based on H. N. Cheng and J. A. Ewen, Makromol. Chem. 1989, 190, 1931.

Mechanical Properties

Test specimens for mechanical property testing were injection-molded following ASTM D618 as closely as possible, and tested at room temperature (23±2° C.).

Tensile properties were determined according to ASTM D638, including Young's modulus, yield stress and yield strain, break stress (also called tensile strength) and break strain, and the stress at given strain values (also called, for example, the 10%, 50%, or 100% modulus for the strain at 10, 50, and 100% strain, respectively). Injection-molded tensile bars were of ASTM D638 Type IV geometry, tested at a speed of 2 inch/min. Break properties were reported only if a majority of test specimens broke before a strain of about 2000%, which is the maximum strain possible on the load frame used for testing. 1% secant modulus (also called flexural modulus herein) was determined according to ASTM D790A, using injection molded flexural bars on a 2-inch support span.

Heat deflection temperature was determined according to ASTM D 648, at 66 psi, on injection-molded specimens. VICAT softening temperature was determined according to ASTM D 1525, using a 200 g load.

Notched Izod impact strength was determined according to ASTM D256, at the specified temperature. A TMI Izod Impact Tester was used. Pairs of specimens were cut from injection-molded ASTM D790 flexural bars; the rectangular bar had a width of about 1.3 cm and a thickness of about 0.3 cm. The notch was oriented such that the impact occurred on the notched side of the specimen (following Procedure A of ASTM D256) in most cases; where specified, the notch orientation was reversed (following Procedure E of ASTM D256) and referred to as "Reverse Notched Izod" (RNI) or "Un-notched Izod" (UNI) impact. All specimens were assigned a thickness of 0.122 inch for calculation of the impact resistance. All breaks were complete, unless specified otherwise.

Optical Properties

The appearance of haze in injection-molded specimens was quantified using two optical methods: Whiteness and Transmission.

Whiteness was determined using a Color Quest XE calorimeter. Color values are relative to the absolute value of a perfect reflecting diffuser measured under the same geometric conditions (per ASTM E 308). Each test specimen was placed at the reflectance port with a white tile behind it. The reflectance/transmittance data, taken at intervals of 10 nm over a wavelength range of 400 to 700 nm, was integrated over the visible spectrum to arrive at the tristimulus X, Y, and Z values. These values simulate the color matching response functions of the human observer as defined by the 1964 CIE 10° Standard Observer. From these values, a Yellowness Index (YI) per ASTM E 313 for a D65 illuminant was calculated as follows: YI=100(1.3013X−1.1498Z)/Y. Since a hazy material appears whiter, or less yellow, than non-hazy material, the YI decreases with increasing haze.

Transmission was determined by measuring the relative intensity of light that passed through a specimen. A Class IIIb Helium-Neon laser beam (633 nm wavelength) was aligned to impinge on a photodiode detector in a dark room. Each test specimen was placed in the beam path, normal to the beam, using a sample holder, and the photodiode signal recorded in volts. This value is the light transmission (LT) of the sample for the given set of conditions (laser intensity, sample thickness, etc.).

Fluid Properties

Pour Point is measured by ASTM D 97. Kinematic Viscosity (KV) is measured by ASTM D 445. Specific gravity is typically determined by ASTM D 4052, at the temperature specified. Viscosity index (VI) is determined by ASTM D 2270. Color is determined on the APHA scale by ASTM D 1209. Note that an APHA color of 100 corresponds to a Saybolt color (ASTM D 156) of about +10; an APHA color of 20 corresponds to a Saybolt color of about +25; and an APHA color of 0 corresponds to a Saybolt color of about +30.

Carbon type composition is determined by ASTM D 2140, and gives the percentage of aromatic carbons ($C_A$), naphthenic carbons ($C_N$), and paraffinic carbons ($C_P$) in the fluid. Specifically, $C_A$ is the wt % of total carbon atoms in the fluid that are in aromatic ring-type structures; $C_N$ is the wt % of total carbon atoms in the fluid that are in saturated ring-type structures; and $C_P$ is the wt % of total carbon atoms in the fluid that are in paraffinic chain-type structures. ASTM D 2140 involves calculating a "Viscosity Gravity Constant" (VGC) and "Refractivity Intercept" (RI) for the fluid, and determining the carbon type composition from a correlation based on these two values. However, this method is known to fail for highly paraffinic oils, because the VGC and RI values fall outside the correlation range. Therefore, for purposes of this invention, the following protocol is used: If the calculated VGC (ASTM D 2140) for a fluid is 0.800 or greater, the carbon type composition including $C_P$ is determined by ASTM D 2140. If the calculated VGC (ASTM D 2140) is less than 0.800, the fluid is considered to have $C_P$ of at least 80%. If the calculated VGC (ASTM D 2140) is less than 0.800 but greater than 0.765, then ASTM D 3238 is used to determine the carbon type composition including $C_P$. If application of ASTM D 3238 yields unphysical quantities (e.g., a negative $C_A$ value), then $C_P$ is defined to be 100%. If the calculated VGC (ASTM D 2140) for a fluid is 0.765 or less, then $C_P$ is defined to be 100%.

The number-average molecular weight ($M_n$) is determined by one of two methods:

1. for samples having a kinematic viscosity at 100° C. of 10 cSt or less use Gas Chromatography (GC) with a mass spectrometer detector, as generally described in "Modern Practice of Gas Chromatography", R. L. Grob and E. F. Barry, Wiley-Interscience, 3rd Edition (July 1995); or 2. for samples having a kinematic viscosity at 100° C. of more than 10 cSt use Gel Permeation Chromatography (GPC) using polystyrene standards, as generally described in "Modern Size Exclusion Liquid Chromatographs", W. W. Yan, J. J. Kirkland, and D. D. Bly, J. Wiley & Sons (1979).

Permanence

Permanence of the NFP is determined by ASTM D1203, by measuring the weight loss from the plasticized composition in the form of a 0.25 mm thick sheet, after 300 hours in dry 70° C. oven. Permanence is 100% minus the Corrected % weight loss, where Corrected % weight loss=(% weight loss for the plasticized composition)−(% weight loss for the unplasticized composition under the same test conditions), % weight loss=100x(W−Wo)/Wo, W=weight after drying and Wo is the weight before drying. The unplasticized composition is the same composition as the plasticized composition but without NFP added.

Methods for Determining NFP Content in Blend

The preferred method to determine the NFP content (weight percent basis) in a blend is the Extraction method. Otherwise, the CRYSTAF method is used, unless the CRYSTAF soluble fraction for the unplasticized polyolefin is greater than 30% in which case the NMR method is used. In event of conflict between the Extraction method and the Crystaff method for the NMR method, the Extraction method shall control. All these methods are solution methods. The latter two involve constructing a model based on a calibration curve (or set of calibration curves) of measured parameter(s) as a function of modifier concentration. The calibration blends are prepared using the same polymer and modifier as the blend(s) under investigation but at known modifier concentrations. This set of calibrants must number at least five, and include the neat polymer as well as at least one modifier concentration above the maximum for the blend(s) under investigation but not greater than 50 weight percent modifier. The blend(s) under investigation are analyzed under the same conditions as the calibrants, and the modifier content determined by applying the model.

Extraction

This method involves Soxhlet extraction, wherein at least a majority of the NFP is extracted with refluxing n-heptane. Analysis of the base polymer is also required because it may contain low molecular weight and/or amorphous material that is soluble in refluxing n-heptane. The level of plasticizer in the blend is determined by correcting its extractables level, in weight percent, by the extractables level for the base polymer, as described below.

The Soxhlet extraction apparatus consists of a 400 ml Soxhlet extractor, with a widened overflow tube (to prevent siphoning and to provide constant flow extraction); a metal screen cage fitted inside the main Soxhlet chamber; a Soxhlet extraction thimble (Whatman, single thickness, cellulose) placed inside the screen cage; a condenser with cooling water and drain; and a one-neck 1000 ml round bottom flask with appropriately sized stir bar and heating mantle.

The procedure is as follows. Dry the soxhlet thimbles in a 95° C. oven for ~60 minutes. Weigh the dry thimble directly after removal from oven; record this weight as A: Thimble Weight Before, in g. Weigh out 15-20 grams of sample (either in pellet or ground pellet form) into the thimble; record as B: Polymer Weight, in g. Place the thimble containing the polymer in the Soxhlet apparatus. Pour about 300 ml of HPLC-grade n-heptane into the round bottom flask with stir bar and secure the flask on the heating mantle. Connect the round bottom flask, the soxhlet, and the condenser in series. Pour more n-heptane down through the center of the condenser into the Soxhlet main chamber until the solvent level is just below the top of the overflow tube. Turn on the cooling water to the condenser. Turn on the heating mantle and adjust the setting to generate a rolling boil in the round bottom flask and maintain a good reflux. Allow to reflux for 16 hours. Turn the heat off but leave the cooling system on. Allow the system to cool down to room temperature. Disassemble the apparatus. Remove the thimble and rinse with a small amount of fresh n-heptane. Allow to air dry in the laboratory hood, followed by oven drying at 95° C. for 90 minutes. Weigh the thimble containing the polymer directly after removal from oven; record as C: Polymer/Thimble Weight After, in g.

The quantity of extract is determined by calculating the weight loss from the sample, W=(A+B−C), in g. The extractables level, E, in weight percent, is then calculated by E=100 (W/B). The plasticizer content in the blend, P, in weight percent, is calculated by P=E(blend)−E(base polymer).

Crystallization Analysis Fractionation (CRYSTAF)

This method involves dissolving a sample in a solvent at high temperature, then cooling the solution slowly to cause fractionation of the sample based on solubility. For semi-crystalline samples, including blends, solubility depends primarily on crystallizability: portions of the sample that are more crystalline will precipitate out of solution at a higher temperature than portions of the sample that are less crystalline. The relative amount of sample in solution as a function of temperature is measured using an infrared (IR) detector to obtain the cumulative solubility distribution. The soluble fraction (SF) is defined as the IR signal at the lowest temperature divided by the IR signal when all the sample is dissolved at high temperature, and corresponds to the weight fraction of sample that has not crystallized.

In the case of a NFP in a thermoplastic polyolefin, the NFP is mostly or entirely amorphous and therefore contributes predominantly or exclusively to the SF. Thus, the SF will be larger for blends with higher NFP content. This relationship is exploited to determine the NFP content of a blend of known composition (polymer and NFP types) but unknown concentration. A calibration curve that describes the trend in SF as a function of NFP content is developed by making a series of blends of known concentration using the same polymer and NFP directly in the CRYSTAF vessels, and then running these blends under the same operating conditions as used for blends of unknown concentration. This series of a minimum of five calibrants must include the neat (unplasticized) polymer, and at least one NFP concentration above and one NFP concentration below the concentration of the unknown sample(s) in order to reliably apply the calibration curve to the unknown sample(s). Typically, a linear fit of the calibration points is found to provide a good representation of the SF as a function of NFP content (i.e., $R^2 > 0.9$); if necessary, a quadratic fit is used to improve the representation of the trend (i.e., $R^2 > 0.9$); if a quadratic fit is still insufficient then more calibrants are run to increase the density of points in the range of interest, and the fit is limited to a narrow enough range that a robust representation of the trend in the range of interest is achieved (i.e., $R^2 > 0.9$). This calibration curve is applied to the SF values measured for the blend(s) under investigation to calculate their respective fluid contents.

A typical CRYSTAF procedure is as follows. A commercial CRYSTAF 200 instrument (Polymer Char S.A., Valencia, Spain) with five stirred stainless steel vessels of 60 mL volume is used. Approximately 30 mg of sample are dissolved for 60 min at 160° C. in 30 mL of 1,2-dichlorobenzene stabilized with 2 g/4 L of butylated hydroxytoluene. The solution is equilibrated for 45 min at 100° C. The crystallization process is carried out by lowering the temperature of the vessels from 100° C. to 30° C. at a rate of 0.2° C./min. A dual wavelength infrared detector with a heated flow through cell maintained at 150° C. is used to measure the polymer concentration in solution at regular intervals during the crystallization cycle; the measuring wavelength is 3.5 μm and the reference wavelength is 3.6 μm.

If the soluble fraction for the unplasticized polyolefin is greater than 30% when analyzed in 1,2-dichlorobenzene as described above, then phenyl ether should be used as the solvent. In this case, the temperatures must be adjusted in the CRYSTAF protocol: the dissolution temperature is 160° C., the equilibration temperature is 160° C., the temperature scan is 160° C. to 80° C., and the detector is maintained at 180° C. Otherwise, the protocol is identical. If the soluble fraction of the unplasticized polyolefin is still greater than 30%, then the NMR method should be used.

Nuclear Magnetic Resonance (NMR)

The second method to determine the amount of NFP in a blend is high-temperature solution-phase $^{13}C$ nuclear magnetic resonance (HTS-CNMR). The composition is determined using the reference spectra of the neat polymer and neat NFP, as well as spectra for a set of calibration blends (i.e., prepared from the neat polymer and NFP at known wt % NFP). The spectra are analyzed to determine a set of one or more diagnostic resonances or clusters of resonances that increase or decrease in strength monotonically with increasing NFP content. The corresponding peaks are integrated and their fractional contribution to the total integral calculated as a function of NFP content (weight %) to generate a set of calibration curves. A chemometrics model is developed using these calibration curves to provide a method to calculate the NFP content. The number of diagnostic resonances is chosen to allow the model to predict NFP content with a precision of 1 wt % or better over the calibration range. For a general description of chemometrics and how to develop a chemometrics model, see *Chemometric Techniques for Quantitative Analysis* by Richard Kramer (Marcel Dekker, 1998). The blend(s) of unknown concentration are then run following the same HTS-CNMR procedure as used for the calibrants, and the results analyzed according to the model to determine the weight % NFP.

A typical HTS-CNMR procedure is as follows. Samples are prepared in 1,1,2,2-tetrachloroethane-$d_2$, with chromium acetylacetonate [Cr(acac)$_3$] added as a relaxation agent to accelerate data acquisition. The Cr(acac)$_3$ concentration in the stock solvent is approximately 15 mg/ml. Sample concentrations are between 10 and 15 weight %. Free induction decays of 15,000 transients are accumulated at a temperature of 120° C. on a Varian UnityPlus 500 using a 10 mm broadband probe. Spectra are acquired with a 90° carbon excitation pulse, and inverse-gated WALTZ-16 proton decoupling. An acquisition time of approximately 1 second and recycle delay of 3.5 seconds are used to allow quantitative integration. Solvent choice and sample concentration may be adjusted to accommodate different solubility and to minimize spectral interference based on the specific composition of the blend. See *Carbon-13 NMR Spectroscopy: High-Resolution Methods and Applications in Organic Chemistry and Biochemistry*, 3rd edition, Eberhard Breitmaier and Wolfgang Voelter (VCH, 1990) for a general description of CNMR techniques.

Processing Methods

Blending

Plasticized blends were prepared by mixing polymer pellets with the plasticizer in a heated C. W. Brabender Instruments Plasticorder to achieve a homogeneous melt at the desired plasticizer concentration. The Brabender was equipped with either a 50 or 200 cm$^3$ volume mixing head and roller blades. The operating temperature was above the melting point of the polymer, typically 190° C. Polymer was first melted in the Brabender for 1 minute at 60 rpm with 0.1 wt % Irganox 2215 added to minimize thermal degradation. The nucleating agent was then added for nucleated blends. Plasticizer was then added slowly to prevent pooling in the melted polymer, with the mixing speed slowed to 30-40 rpm. The blend was then mixed for 5 minutes at 60 rpm under a nitrogen purge. The Brabender was opened and the melt removed from the mixing head and blades as quickly as possible, and allowed to solidify. For those blends later subjected to injection molding, the pieces of material from the Brabender were cut into smaller pieces using a guillotine, then ground into even smaller pieces using a Wiley Mill. For those blends later subjected to compression molding, pieces of material from the Brabender were used directly.

Injection Molding

Tensile and flexure bars were molded using 20 ton injection molding equipment (Nissei NS 20) according to ASTM D 4101, except for the following provisions: the mold temperature was 40° C.; the inject time was 30 sec; the tensile and flex bars were of ASTM D 638 Type IV and ASTM D 790 geometries, respectively; and the melt temperature was, in some cases, 10° C. off from the value specified by ASTM D 4101, but always in the range of 190-200° C.

Compression Molding

Blends were compression molded into plaques about 2 mm thick and about 100 cm² area between sheets of Teflon-coated aluminum foil using a heated hydraulic press at 190° C., a molding time of 15 min, and a press force of 10,000 lb$_f$ (44.5 kN). Immediately thereafter, the foil/sample/foil sandwich was immersed in room temperature water for about 5 min. The plaque was removed from the foil and dried in air.

EXAMPLES

The present invention, while not meant to be limited by, may be better understood by reference to the following examples and tables. Blend components used to prepare the Example Blends are reported in Table 1a; compositions of the Example Blends are reported in Table 1b. All blending was performed as described in the Processing Methods section. Test specimens from Example Blends 1-18 were injection molded, while specimens from Example Blends 19-28 were compression molded; both molding methods were performed as described in the Processing Methods section. Optical and tactile properties of these specimens are reported in Table 2. Physical properties of these specimens are reported in Table 3. A comparison of the appearance of injection-molded specimens with 10 wt % NFP is provided in FIG. 1.

TABLE 1

Components used in Example blends

| Component | Product | Commercial Source |
|---|---|---|
| hPP | PP1024E1, homopolymer polypropylene; MFR ~13 dg/min, Mw/Mn ~2.9, and ~167° C. melting point | ExxonMobil Chemical Houston, TX |
| RCP | PP9524, propylene-ethylene copolymer; MFR ~12 dg/min, Mw/Mn ~3.0, and ~143° C. melting point | ExxonMobil Chemical Houston, TX |
| Nucleating Agent A (NA-A) | Millad 3988 [1,3:2,4-bis(3,4-dimethylbenzylidene)sorbitol] | Milliken Chemical Spartanburg, SC |
| Nucleating Agent B (NA-B) | NA-11 [CAS# 85209-91-2] | Amfine Chemical Corp. Upper Saddle River, NJ |
| Nucleating Agent C (NA-C) | HPN-68 [2.2.1-heptane-bicyclodicarboxylic acid] | Milliken Chemical Spartanburg, SC |
| Nucleating Agent D (NA-D) | Sodium Benzoate | Ciba Specialty Chemicals Basel, Switzerland |
| PAO | SpectraSyn 10 | ExxonMobil Chemical Houston, TX |

TABLE 1b

Example Blend compositions (ppm on weight basis)

| Example | PP + NA | ppm NA | wt % PAO | Example | PP/NA | ppm NA | wt % PAO |
|---|---|---|---|---|---|---|---|
| 1 | hPP | 0 | 0 | 15 | hPP + NA-D | 1500 | 0 |
| 2 | hPP | 0 | 10 | 16 | hPP + NA-D | 1500 | 10 |
| 3 | hPP + NA-A | 2500 | 0 | 17 | hPP + NA-D | 1500 | 15 |
| 4 | hPP + NA-A | 2500 | 10 | 18 | hPP + NA-D | 1500 | 20 |
| 5 | hPP + NA-A | 2500 | 15 | 19 | RCP | 0 | 0 |
| 6 | hPP + NA-A | 2500 | 20 | 20 | RCP | 0 | 5 |
| 7 | hPP + NA-B | 1500 | 0 | 21 | RCP | 0 | 10 |
| 8 | hPP + NA-B | 1500 | 10 | 22 | RCP | 0 | 15 |
| 9 | hPP + NA-B | 1500 | 15 | 23 | RCP | 0 | 20 |
| 10 | hPP + NA-B | 1500 | 20 | 24 | RCP + NA-A | 2500 | 0 |
| 11 | hPP + NA-C | 800 | 0 | 25 | RCP + NA-A | 2500 | 5 |
| 12 | hPP + NA-C | 800 | 10 | 26 | RCP + NA-A | 2500 | 10 |
| 13 | hPP + NA-C | 800 | 15 | 27 | RCP + NA-A | 2500 | 15 |
| 14 | hPP + NA-C | 800 | 20 | 28 | RCP + NA-A | 2500 | 20 |

When sufficiently high loadings of NFP are added to some thermoplastic polyolefins, injection-molded specimens from such blends become hazy upon cooling after the molding process. This haze is characterized by regions in the interior of the specimens that become cloudy, or whitish, to the naked eye (typically the haziness is more prominent farther away from the injection molding gate). The basic phenomena is shown in FIG. 1a (Example 2). When nucleating agent is added to the blend, the NFP loading level associated with the onset of optical haziness is increased. The efficiency of this effect depends on the type and amount of nucleating agent employed. One consequence is that a plasticized thermoplastic polyolefin blend, with sufficient NFP content to cause haziness in injection molded specimens in the absence of nucleating agent, can be made to give homogeneous (no haze detectable by the naked eye) specimens by judicious choice of the type and amount of nucleating agent to add to the otherwise identical blend (i.e., without a meaningful change in the NFP content) and therefore extend the acceptable level of plasticization. A similar description holds for the effect of NA on the apparent exudation of oil to the surface of some compression-molded samples from NFP-plasticized thermoplastic polyolefins: addition of NA effectively increases the loading level of NFP required before the surface becomes oily to the touch, and therefore judicious combination of NFP and NA will allow for greater acceptable plasticization levels than without NA. The concentration of NFP required to cause haziness and/or oiliness in a thermoplastic polyolefin seems to depend on the degree of crystallinity and the morphology developed upon crystallization.

The visual appearance of injection-molded specimens for Example Blends 1-18 are recorded in Table 2a. Optically homogeneity was found to be long lasting, if not permanent, as demonstrated by annealing several specimens at 140° C. in air for 20 hr with no detectable change in appearance. These observations support a conclusion that addition of NA increases the level of NFP required for haze to occur in hPP/NFP blends.

The extent of haziness was quantified by measuring the optical properties of injection-molded dogbones for Example Blends 1-18, specifically the Yellowness Index (YI) and Light Transmission (LT). Often, in cases where haze was observed, the end of the dogbone close to the injection gate ("gate end") was homogeneous while the opposite end ("non-gate end") was hazy. Therefore, the optical properties for the non-gate end were evaluated. In samples that exhibit haziness, molded specimens appear whiter, or less yellow, to the Colorimeter. A value Δ(YI) was calculated for each blend of hPP+NFP by comparing its YI to the YI for nucleated but unplasticized hPP with the equivalent nucleating agent loading. A large negative value for Δ(YI) indicates that the sample with NFP is more hazy (less yellow, more white) than the one without NFP. Samples that exhibit haziness also allow less light to pass through, and so give lower light transmission. A relative LT (RLT) was calculated for each blend of hPP+NFP by taking the ratio of its LT to the LT for nucleated but unplasticized hPP with the equivalent nucleating agent loading. A small RLT indicates that the sample with NFP is more hazy (less light transmission) than the one without NFP. The Δ(YI) and RLT data, reported in Table 2a, further support the conclusion that addition of NA increases the level of NFP required for haze to occur in hPP/NFP blends.

TABLE 2a

Effect of nucleating agent on the appearance of hPP/NFP blends

| Example | PP/NA | wt % PAO | Visual appearance | Δ(YI) | RLT |
|---------|-------|----------|-------------------|-------|------|
| 1 | hPP | 0 | clear | | |
| 2 | hPP | 10 | hazy | −8 | 0.09 |
| 3 | hPP + NA-A | 0 | clear | | |
| 4 | hPP + NA-A | 10 | clear | −1 | 0.28 |
| 5 | hPP + NA-A | 15 | clear | −4 | 0.07 |
| 6 | hPP + NA-A | 20 | hazy | −15 | 0.02 |
| 7 | hPP + NA-B | 0 | clear | | |
| 8 | hPP + NA-B | 10 | clear | 0 | 0.13 |
| 9 | hPP + NA-B | 15 | clear | −2 | 0.06 |
| 10 | hPP + NA-B | 20 | hazy | −16 | 0.03 |
| 11 | hPP + NA-C | 0 | clear | | |
| 12 | hPP + NA-C | 10 | clear | +1 | 0.59 |
| 13 | hPP + NA-C | 15 | clear | +1 | 0.23 |
| 14 | hPP + NA-C | 20 | mixed | −10 | 0.16 |
| 15 | hPP + NA-D | 0 | clear | | |
| 16 | hPP + NA-D | 10 | clear | −2 | 0.35 |
| 17 | hPP + NA-D | 15 | hazy | −16 | 0.09 |
| 18 | hPP + NA-D | 20 | hazy | −14 | 0.21 |

The tactile properties of compression-molded specimens for Example Blends 19-28 are recorded in Table 2b. The specimens were allowed to age for 8-12 hours in air at room temperature (~23° C.), then the surfaces were examined by touch to gain a qualitative sense of surface dryness or oiliness. These observations support the conclusion that addition of NA increases the level of NFP required for exudation to occur in RCP/NFP blends.

TABLE 2b

Effect of nucleating agent on the oiliness of RCP/NFP blends

| Example | PP/NA | wt % PAO | Oily Surface |
|---------|-------|----------|--------------|
| 19 | RCP | 0 | no |
| 20 | RCP | 5 | no |
| 21 | RCP | 10 | no |
| 22 | RCP | 15 | yes |
| 23 | RCP | 20 | yes |
| 24 | RCP + NA-A | 0 | no |
| 25 | RCP + NA-A | 5 | no |
| 26 | RCP + NA-A | 10 | no |
| 27 | RCP + NA-A | 15 | no |
| 28 | RCP + NA-A | 20 | no |

Table 2c provides a summary of the data in Table 2a-b by reporting the NFP content associated with the onset of optical haziness or surface oiliness for the Example Blends. For a given nucleating agent, if the amount of NFP added to PP in a PP/NFP/NA blend is less than this level, the resulting specimens are optically homogeneous and dry.

TABLE 2b

Effect of nucleating agent on NFP loading in PP/NFP/NA blends where specimens start to exhibit internal haziness or surface oiliness

| PP | Nucleating Agent | ppm (wt) NA | PAO content Where Evidence of Internal Haziness or Surface Oiliness is Detected |
|----|------------------|-------------|-----|
| hPP | none | — | 10 |
| hPP | NA-A | 2500 | 20 |
| hPP | NA-B | 1500 | 20 |
| hPP | NA-C | 800 | ~20 |
| hPP | NA-D | 1500 | 15 |
| RCP | none | — | 15 |
| RCP | NA-A | 2500 | >20 |

Table 3a-c reports flow (MFR) and mechanical property (tensile, flexure, softening point, and impact) data for Example Blends 1-18. It can be concluded that optically homogeneous blends also exhibit a more desirable set of mechanical properties. Addition of nucleating agent has little effect on tensile strength or ductility, while addition of NFP decreases tensile strength and increases ductility. Stiffness, HDT, and impact strength of hPP/NFP blends are increased by nucleating agent.

TABLE 3a

Flow properties of Example Blends

| Example | PP/NA | wt % PAO | Visual | MFR dg/min |
|---------|-------|----------|--------|-------------|
| 1 | hPP | 0 | clear | 11 |
| 2 | hPP | 10 | hazy | 20 |
| 3 | hPP + NA-A | 0 | clear | 12 |
| 4 | hPP + NA-A | 10 | clear | 21 |
| 5 | hPP + NA-A | 15 | clear | 31 |
| 6 | hPP + NA-A | 20 | hazy | 47 |
| 7 | hPP + NA-B | 0 | clear | 12 |
| 8 | hPP + NA-B | 10 | clear | 21 |
| 9 | hPP + NA-B | 15 | clear | 34 |
| 10 | hPP + NA-B | 20 | hazy | 44 |
| 11 | hPP + NA-C | 0 | clear | 13 |
| 12 | hPP + NA-C | 10 | clear | 21 |
| 13 | hPP + NA-C | 15 | clear | 30 |
| 14 | hPP + NA-C | 20 | mixed | 44 |
| 15 | hPP + NA-D | 0 | clear | 11 |
| 16 | hPP + NA-D | 10 | clear | 20 |
| 17 | hPP + NA-D | 15 | hazy | 30 |
| 18 | hPP + NA-D | 20 | hazy | 44 |

TABLE 3b

Tensile properties of Example Blends

| Example | PP/NA | wt % PAO | Visual | Tensile Strength MPa | Break Strain % | Modulus at Strain of 10% MPa | 50% MPa | 100% MPa |
|---|---|---|---|---|---|---|---|---|
| 1 | hPP | 0 | clear | 28.9 | 23 | 37.9 | ** | ** |
| 2 | hPP | 10 | hazy | 20.2 | 80 | 26.8 | 24.7 | ** |
| 3 | hPP + NA-A | 0 | clear | 38.0 | 23 | 40.0 | ** | ** |
| 4 | hPP + NA-A | 10 | clear | 22.4 | 57 | 31.5 | 24.1 | ** |
| 5 | hPP + NA-A | 15 | clear | 17.8 | 96 | 25.0 | 24.6 | 16.7 |
| 6 | hPP + NA-A | 20 | hazy | 16.1 | 113 | 19.9 | 21.3 | 18.2 |
| 7 | hPP + NA-B | 0 | clear | 38.5 | 19 | 40.9 | ** | ** |
| 8 | hPP + NA-B | 10 | clear | 19.2 | 75 | 29.2 | 23.9 | ** |
| 9 | hPP + NA-B | 15 | clear | 17.0 | 149 | 23.4 | 24.3 | 19.7 |
| 10 | hPP + NA-B | 20 | hazy | 14.7 | 310 | 18.5 | 21.2 | 18.7 |
| 11 | hPP + NA-C | 0 | clear | 40.6 | 20 | 40.8 | ** | ** |
| 12 | hPP + NA-C | 10 | clear | 17.6 | 86 | 28.7 | 23.7 | ** |
| 13 | hPP + NA-C | 15 | clear | 17.1 | 137 | 22.9 | 24.0 | 19.2 |
| 14 | hPP + NA-C | 20 | mixed | 16.6 | 241 | 18.7 | 20.8 | 18.8 |
| 15 | hPP + NA-D | 0 | clear | 39.6 | 25 | 41.1 | ** | ** |
| 16 | hPP + NA-D | 10 | clear | 18.9 | 82 | 29.2 | 24.9 | ** |
| 17 | hPP + NA-D | 15 | hazy | 18.0 | 119 | 23.7 | 25.0 | 19.7 |
| 18 | hPP + NA-D | 20 | hazy | 19.0 | 103 | 19.4 | 21.7 | 19.3 |

** denotes that specimen broke before reaching the required elongation

TABLE 3c

Flexure modulus, softening temperatures, and impact strengths of Example Blends

| Example | PP/NA | wt % PAO | Visual | 1% Secant Flex Mod kpsi | Vicat °C. | HDT °C. | NI, 23° C. ft-lb/in | UNNI, −18° C. ft-lb/in |
|---|---|---|---|---|---|---|---|---|
| 1 | hPP | 0 | clear | 192 | 154 | 79 | 0.41 | 2.88 |
| 2 | hPP | 10 | hazy | 113 | 148 | 77 | 0.62 | 0.55 |
| 3 | hPP + NA-A | 0 | clear | 267 | 154 | 111 | 0.41 | 2.25 |
| 4 | hPP + NA-A | 10 | clear | 143 | 149 | 97 | 0.90 | 0.49 |
| 5 | hPP + NA-A | 15 | clear | 116 | 146 | 89 | 1.24 | 0.68 |
| 6 | hPP + NA-A | 20 | hazy | 92 | 142 | 79 | 1.49 | 0.67 |
| 7 | hPP + NA-B | 0 | clear | 251 | 154 | 107 | 0.51 | 2.82 |
| 8 | hPP + NA-B | 10 | clear | 133 | 149 | 88 | 0.92 | 15.3 |
| 9 | hPP + NA-B | 15 | clear | 100 | 146 | 79 | 1.07 | 16.8 |
| 10 | hPP + NA-B | 20 | hazy | 85 | 143 | 76 | 1.86 | 28.2 |
| 11 | hPP + NA-C | 0 | clear | 237 | 154 | 107 | 0.37 | 2.48 |
| 12 | hPP + NA-C | 10 | clear | 124 | 148 | 88 | 0.94 | 13.2 |
| 13 | hPP + NA-C | 15 | clear | 97 | 146 | 79 | 0.92 | 17.6 |
| 14 | hPP + NA-C | 20 | mixed | 75 | 142 | 72 | 1.40 | 29.2 |
| 15 | hPP + NA-D | 0 | clear | 237 | 155 | 103 | 0.43 | 0.17 |
| 16 | hPP + NA-D | 10 | clear | 128 | 149 | 86 | 0.71 | 0.40 |
| 17 | hPP + NA-D | 15 | hazy | 100 | 146 | 76 | 0.94 | 0.51 |
| 18 | hPP + NA-D | 20 | hazy | 78 | 143 | 70 | 0.71 | 0.58 |

HDT = Heat Deflection Temperature (ASTM D 648);
NI = Notched Izod (ASTM D 256A);
UNNI = Un-Noched Izod (ASTM D 256E);
ft-lb/in = 53.4 J/m Table 4a-b reports DSC data for Example Blends 1-18. Each crystallization and melting transition exhibited a single peak. Addition of a nucleating agent increases the crystallization temperature ($T_c$), heat of crystallization ($H_c$), and heat of fusion ($H_f$) of hPP and hPP/NFP blends. Normalized $H_c$ and $H_f$ values are also reported; these are values based on the weight of the polymer (instead of the weight of the blend); that is NormH$_f$ and NormH$_c$ are calculated using the weight of hPP only. The nucleating agent is found to have a minimal effect on the melting temperature ($T_m$) of hPP at a given NFP loading (c.f., Examples 2, 4, 8, 12, and 16 all have $T_m$~164° C.), while increasing concentration of NFP depresses $T_m$ slightly (by less than 5° C. for 20 wt % NFP). Addition of nucleating agent reduces the crystallization half time of hPP/NFP blends; the magnitude of this effect depends on the particular nucleating agent (e.g., NA-A has a larger effect than NaOBz).

TABLE 4a

DSC thermal transition data for Example Blends

| Example | PP/NA | wt % PAO | Visual | Crystallization | | | Melting | | |
|---|---|---|---|---|---|---|---|---|---|
| | | | | $T_c$ (° C.) | $H_c$ (J/g) | Norm $H_c$ (J/g) | $T_m$ (° C.) | $H_f$ (J/g) | Norm $H_f$ (J/g) |
| 1 | hPP | 0 | clear | 99 | 103 | 103 | 167 | 85 | 85 |
| 2 | hPP | 10 | hazy | 103 | 88 | 98 | 165 | 73 | 81 |
| 3 | hPP + NA-A | 0 | clear | 122 | 115 | 115 | 166 | 103 | 103 |
| 4 | hPP + NA-A | 10 | clear | 123 | 107 | 119 | 164 | 88 | 98 |
| 5 | hPP + NA-A | 15 | clear | 125 | 100 | 118 | 163 | 68 | 80 |
| 6 | hPP + NA-A | 20 | hazy | 122 | 103 | 129 | 161 | 80 | 100 |
| 7 | hPP + NA-B | 0 | clear | 119 | 117 | 117 | 165 | 104 | 104 |
| 8 | hPP + NA-B | 10 | clear | 116 | 109 | 121 | 163 | 90 | 100 |
| 9 | hPP + NA-B | 15 | clear | 114 | 103 | 121 | 162 | 89 | 105 |
| 10 | hPP + NA-B | 20 | hazy | 118 | 102 | 128 | 161 | 87 | 109 |
| 11 | hPP + NA-C | 0 | clear | 121 | 120 | 120 | 166 | 102 | 102 |
| 12 | hPP + NA-C | 10 | clear | 118 | 110 | 122 | 163 | 97 | 108 |
| 13 | hPP + NA-C | 15 | clear | 116 | 106 | 125 | 162 | 94 | 111 |
| 14 | hPP + NA-C | 20 | mixed | 118 | 104 | 130 | 161 | 88 | 110 |
| 15 | hPP + NA-D | 0 | clear | 110 | 103 | 103 | 166 | 81 | 81 |
| 16 | hPP + NA-D | 10 | clear | 109 | 104 | 116 | 163 | 75 | 83 |
| 17 | hPP + NA-D | 15 | hazy | 112 | 94 | 111 | 162 | 68 | 80 |
| 18 | hPP + NA-D | 20 | hazy | 111 | 96 | 120 | 161 | 76 | 95 |

TABLE 4b

DSC crystallization half time for Example Blends

| Example | PP/NA | wt % PAO | Visual | Crystallization Half Time, min | |
|---|---|---|---|---|---|
| | | | | 125° C. | 140° C. |
| 1 | hPP | 0 | clear | 4.3 | ** |
| 2 | hPP | 10 | hazy | 5.2 | ** |
| 3 | hPP + NA-A | 0 | clear | 0.13 | 3 |
| 4 | hPP + NA-A | 10 | clear | 0.21 | 6 |
| 5 | hPP + NA-A | 15 | clear | 0.25 | 6 |
| 6 | hPP + NA-A | 20 | hazy | 0.26 | 9 |
| 7 | hPP + NA-B | 0 | clear | 0.30 | 7 |
| 8 | hPP + NA-B | 10 | clear | 0.57 | 17 |
| 9 | hPP + NA-B | 15 | clear | 0.68 | ** |
| 10 | hPP + NA-B | 20 | hazy | 0.40 | 14 |
| 11 | hPP + NA-C | 0 | clear | 0.22 | 3 |
| 12 | hPP + NA-C | 10 | clear | 0.43 | 7 |
| 13 | hPP + NA-C | 15 | clear | 0.55 | 11 |
| 14 | hPP + NA-C | 20 | mixed | 0.38 | 7 |
| 15 | hPP + NA-D | 0 | clear | 1.9 | ** |
| 16 | hPP + NA-D | 10 | clear | 3.5 | ** |
| 17 | hPP + NA-D | 15 | hazy | 2.2 | ** |
| 18 | hPP + NA-D | 20 | hazy | 6.3 | ** |

** denotes the sample did not crystallize

Table 4c reports DSC data for Example Blends 19-28. Each crystallization and melting transition exhibited a single peak. Addition of a nucleating agent increases the crystallization temperature ($T_c$) and melting temperature ($T_m$) of RCP and RCP/NFP blends; addition of NFP depresses these values slightly (by a few ° C.) if at all.

TABLE 4c

DSC thermal transition data for Example Blends

| Example | PP/NA | wt % PAO | Feel | $T_c$ (° C.) | $T_m$ (° C.) |
|---|---|---|---|---|---|
| 19 | RCP | 0 | dry | 98 | 143 |
| 20 | RCP | 5 | dry | 100 | 144 |
| 21 | RCP | 10 | dry | 97 | 141 |
| 22 | RCP | 15 | oily | 98 | 143 |
| 23 | RCP | 20 | oily | 95 | 140 |
| 24 | RCP + NA-A | 0 | dry | 119 | 151 |
| 25 | RCP + NA-A | 5 | dry | 116 | 148 |
| 26 | RCP + NA-A | 10 | dry | 118 | 149 |
| 27 | RCP + NA-A | 15 | dry | 114 | 146 |
| 28 | RCP + NA-A | 20 | dry | 116 | 147 |

While the present invention has been described and illustrated by reference to particular embodiments, those of ordinary skill in the art will appreciate that the invention lends itself to many different variations not illustrated herein. For these reasons, then, reference should be made solely to the appended claims for purposes of determining the scope of the present invention. Further, certain features of the present invention are described in terms of a set of numerical upper limits and a set of numerical lower limits. It should be appreciated that ranges formed by any combination of these limits are within the scope of the invention unless otherwise indicated.

All priority documents are herein fully incorporated by reference for all jurisdictions in which such incorporation is permitted. Further, all documents cited herein, including testing procedures, are herein fully incorporated by reference for all jurisdictions in which such incorporation is permitted, to the extent such is not inconsistent with this specification.

We claim:

1. A composition comprising a plasticized polyolefin composition comprising one or more polyolefins, one or more non-functionalized plasticizers, and a nucleating agent; wherein at least one of the non-functionalized plasticizers has a specific gravity of 0.86 or less and a viscosity index of 120 or more, and a kinematic viscosity of from 10 cSt to 1000 cSt at 100° C., wherein the polyolefin consists essentially of a propylene homopolymer, a propylene copolymer, an in situ propylene impact copolymer, or mixtures thereof and is present at 50 to 99.99 weight percent, based upon the weight of the composition, wherein the 1% secant flexural modulus of the polyolefin is 5 MPa or more and the 1% secant flexural modulus of the plasticized composition is 5 MPa or more, wherein ethylene homopolymers and copolymers having a weight average molecular weight of from 500 to 10,000 are substantially absent from the composition.

2. The composition of claim 1 wherein the nucleating agent is selected from the group consisting of silica, kaolin, carbon black, talc, phosphonic acid salts, carboxylate salts, aromatic carboxylic-acid salts, metal phosphates, phosphate esters, phosphate ester salts; metal salts of suberic acid, metal salts of hexahydrophthalic acid, salts of disproportionated rosin esters, sorbitol, dibenzylidene sorbitol, sorbitol acetal, sorbitol di-acetal, quinacridone dyes, carboxamide, naphthalene carboxamide, benzenetrisamide, trimesic acid derivatives, poly(3-methyl-1-butene), poly(dimethylstyrene), poly(ethylene terephthalate), polyamides (nylons), and polycarbonates.

3. The composition of claim 1 wherein the nucleating agent is selected from the group consisting of sodium benzoate, sodium naphthenoate, sodium 2,2'-methylenebis(4,6-di-tert-butylphenyl)phosphate, aluminum 2,2'-methylenebis(4,6-di-tert-butylphenyl)phosphate, di(p-tolylidene)sorbitol, dibenzylidene sorbitol, di(p-methylbenzylidene)sorbitol, di(p-ethylbenzylidene)sorbitol, bis(3,4-dimethylbenzylidene) sorbitol, N,N'-dicyclohexyl-2,6-naphthalenedicarboxamide, 1,3:2,4-dibenzylidenesorbitol, [2.2.1]-heptane-bicyclodicarboxylic acid, N,N'-dicyclohexyl-2,6-naphathalene dicarboxamide, (1,3:2,4)dimethyldibenzylidene sorbitol, and 2,2'-methylenebis(4,6-di-tertbutylphenol)phosphate salt.

4. The composition of claim 1 wherein the nucleating agent is present at 0.01 to 1 wt %, based upon the weight of the composition.

5. The composition of claim 1 wherein at least one of the non-functionalized plasticizers comprises oligomers of $C_5$ to $C_{24}$ olefins.

6. The composition of claim 1 wherein at least one of the non-functionalized plasticizers comprises oligomers of a single alpha-olefin having 5 to 24 carbons.

7. The composition of claim 1 wherein at least one of the non-functionalized plasticizers comprises oligomers of two or more alpha-olefins having 3 to 24 carbons, provided that any alpha-olefins having only three or only four carbons atoms are present at 10 weight % or less.

8. The composition of claim 1 wherein the non-functionalized plasticizer comprises at least 50 weight % of $C_6$ to $C_{100}$ isoparaffins.

9. The composition of claim 1 wherein the non-functionalized plasticizer comprises an oligomer of 1-octene, 1-decene, and/or 1-dodecene having a number-average molecular weight of 500 to 5,000 g/mol.

10. The composition of claim 1 wherein the non-functionalized plasticizer comprises a mineral oil having a saturates levels of 90% or more, and sulfur contents of 0.03% or less.

11. The composition of claim 1 wherein the non-functionalized plasticizer has a paraffinic carbon content (Cp) of about 80% or more.

12. The composition of claim 1 wherein at least one of the non-functionalized plasticizers has a flash point of 200° C. or more.

13. The composition of claim 1 wherein the non-functionalized plasticizer has a pour point of −20° C. or less.

14. The composition of claim 1 wherein at least one of the non-functionalized plasticizers has a pour point of −40° C. or less and a specific gravity of 0.84 or less.

15. The composition of claim 1 wherein the non-functionalized plasticizer has a kinematic viscosity at 100° C. of 35 cSt or more.

16. The composition of claim 1 wherein the non-functionalized plasticizer has a pour point of −40° C. or less and a specific gravity of 0.84 or less.

17. The composition of claim 1 wherein the non-functionalized plasticizers has a kinematic viscosity at 100° C. of 35 cSt or more and a flash point of 200° C. or more.

18. The composition of claim 3 wherein the non-functionalized plasticizer has a pour point of −20° C. or less and a flash point of 200° C. or more.

19. The composition of claim 1 wherein the non-functionalized plasticizer has a number average molecular weight of 300 to 1800 g/mol.

20. The composition of claim 1 wherein the non-functionalized plasticizer has a number-average molecular weight of 500 to 1200 g/mol.

21. The composition of claim 1 wherein the composition comprises greater than 10 wt % non-functionalized plasticizer.

22. The composition of claim 1 wherein the composition comprises from about 2 to about 10 wt % non-functionalized plasticizer.

23. The composition of claim 1 wherein the polyolefin comprises an in situ polypropylene impact copolymer.

24. The composition of claim 1 wherein the polyolefin comprises isotactic polypropylene.

25. The composition of claim 1 wherein the polyolefin comprises syndiotactic polypropylene.

26. The composition of claim 1 wherein the polypropylene copolymer comprises a random copolymer of propylene and up to 5 wt % of ethylene.

27. The composition of claim 1 wherein the polyolefin has an Mw of 30,000 to 1,000,000 g/mol.

28. The composition of claim 1 wherein the polyolefin has an Mw/Mn of 1.6 to 10.

29. The composition of claim 1 wherein the polyolefin has a melting point (second melt) of 30 to 185° C.

30. The composition of claim 1 wherein the polyolefin has a crystallinity of 5 to 80%.

31. The composition of claim 1 wherein the polyolefin has a heat of fusion between 20 to 150 J/g.

32. The composition of claim 1 wherein the polyolefin is a propylene homopolymer or a propylene copolymer and has a Gardner impact strength, tested on 0.125 inch disk at 23° C. of 20 in-lb to 1000 in-lb.

33. The composition of claim 1 wherein the polyolefin has a 1% secant flexural modulus of from 100 MPa to 2300 MPa.

34. The composition of claim 1 wherein the polyolefin has a melt flow rate from 0.3 to 500 dg/min as determined according to ASTM D 1238 (230° C./2.16 kg).

35. The composition of claim 1 wherein the polyolefin comprises a copolymer of propylene and from 0.5 to 30 wt % of one or more comonomers selected from the group consisting of ethylene, butene, pentene, hexene, heptene, octene, nonene, decene, dodecene, 4-methyl-pentene-1,3-methyl pentene-1,5-ethyl-1-nonene, and 3,5,5-trimethyl-hexene-1.

36. The composition of claim 1 wherein the polyolefin comprises propylene, from 0 to 5 wt % of a diene, and from 2 wt % to 25 wt % ethylene, based on the total weight of the polymer and has a narrow compositional distribution; a melting point (Tm) of from 25° C. to 120° C.; a heat of fusion of from 50 J/g to 3 J/g; an Mw/Mn of from 1.5 to 5; and a melt index (MI) as determined according to ASTM D 1238 (190° C./2.16 kg) of less than 20 dg/min.

37. The composition of claim 1 wherein the polyolefin has a tacticity index of 4 to 12.

38. The composition of claim 1 wherein the polyolefin is a propylene random copolymer (RCP) or a propylene homopolymer, the non-functionalized plasticizer is polyalpha olefin, a GTL-derived base-stock or base-oil that has a kinematic viscosity at 100° C. of 10 to 500 cSt and/or a number average molecular weight ($M_n$) of 300 to 10,000 g/mol, or a hydrocarbon oil with a saturates level of 90% or more, a sulfur content of less than 0.03%; and the nucleating agent is sodium benzoate or 3,4-dimethylbenzylidene sorbitol.

39. The composition of claim 1 further comprising polyethylene or a polybutene.

40. The composition of claim 1 wherein the polyolefin further comprises a plastomer.

41. The composition of claim 1 wherein the plasticized composition has a single glass transition temperature that is below that of the polyolefin itself.

42. The composition of claim 1 wherein the $T_g$ of the plasticized composition is at least 10° C. lower than that of the unplasticized polyolefin.

43. The composition of claim 1 wherein the peak melting temperature of the unplasticized polyolefin is within 5° C. of the plasticized polyolefin.

44. The composition of claim 1 wherein the crystallization temperature of the unplasticized polyolefin is within 5° C. of the plasticized polyolefin.

45. The composition of claim 1 wherein a ⅛ inch thick injection molded specimen of the composition has a Δ(YI) of less than 6.5 and at least one of the YI values greater than 5, wherein YI is the yellowness index determined according to ASTM E 313.

46. An article comprising the composition of claim 1.

47. The article of claim 46, where the article is selected from the group consisting of cookware, storageware, toys, medical devices, sterilizable medical devices, sterilization containers, healthcare items, sheets, crates, containers, bottles, packaging, wire and cable jacketing, pipes, geomembranes, sporting equipment, chair mats, tubing, profiles, instrumentation sample holders and sample windows, outdoor furniture, playground equipment, automotive, boat components, water craft components, and automotive components.

48. The article of claim 46, where the article is selected from the group consisting of bumpers, grills, trim parts, dashboards, instrument panels, exterior door components, hood components, spoiler, wind screen, hub caps, mirror housing, body panel, and protective side molding.

49. The article of claim 46, where the article is selected from the group consisting of interior and external components associated with a vehicle.

50. A film comprising the composition of claim 1.

51. A molded article comprising the composition of claim 1.

52. A process to make an article comprising forming the composition of claim 1 into an article.

\* \* \* \* \*

UNITED STATES PATENT AND TRADEMARK OFFICE
CERTIFICATE OF CORRECTION

PATENT NO. : 7,652,092 B2
APPLICATION NO. : 11/406654
DATED : January 26, 2010
INVENTOR(S) : Tse et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 30 days.

Signed and Sealed this

Twenty-third Day of November, 2010

David J. Kappos
*Director of the United States Patent and Trademark Office*